US012790369B2

(12) United States Patent
Lim et al.

(10) Patent No.: US 12,790,369 B2
(45) Date of Patent: Nov. 10, 2026

(54) FUSION PEPTIDES CONTAINING DIMERIC ALPHA-HELICES, PEPTIDE-MOLECULAR CONJUGATES CONTAINING THE SAME AND NUCLEIC ACID DELIVERY COMPOSITIONS CONTAINING THE SAME

(71) Applicant: ARTPROBIO CO., LTD., Seoul (KR)

(72) Inventors: Yong-Beom Lim, Seoul (KR); Youjin Jung, Seoul (KR); Zhi Hao Zhang, Seoul (KR)

(73) Assignee: ARTPROBIO CO., LTD., Seoul (KR)

( * ) Notice: Subject to any disclaimer, the term of this patent is extended or adjusted under 35 U.S.C. 154(b) by 766 days.

(21) Appl. No.: 18/185,167

(22) Filed: Mar. 16, 2023

(65) Prior Publication Data

US 2024/0116986 A1 Apr. 11, 2024

(30) Foreign Application Priority Data

Mar. 21, 2022 (KR) ........................ 10-2022-0034890
Feb. 21, 2023 (KR) ........................ 10-2023-0023099

(51) Int. Cl.

| | |
|---|---|
| ***C07K 7/08*** | (2006.01) |
| ***A61K 31/13*** | (2006.01) |
| ***A61K 31/4706*** | (2006.01) |
| ***A61K 47/54*** | (2017.01) |
| ***A61K 47/60*** | (2017.01) |
| ***A61K 47/62*** | (2017.01) |
| ***A61K 47/69*** | (2017.01) |
| ***A61K 48/00*** | (2006.01) |

(52) U.S. Cl.

CPC ................ *C07K 7/08* (2013.01); *A61K 31/13* (2013.01); *A61K 31/4706* (2013.01); *A61K 47/549* (2017.08); *A61K 47/60* (2017.08); *A61K 47/62* (2017.08); *A61K 47/6929* (2017.08); *A61K 48/0041* (2013.01); *C07K 2319/00* (2013.01)

(58) Field of Classification Search

CPC .................. C07K 7/08; C07K 2319/00; A61K 47/6929; A61K 47/64; C12N 15/87

See application file for complete search history.

(56) References Cited

U.S. PATENT DOCUMENTS

2018/0264124 A1 9/2018 Fujii

FOREIGN PATENT DOCUMENTS

KR 1020170127380 11/2017

OTHER PUBLICATIONS

Biochemistry 2004, 43, 11560-11566 The Mechanism of â-Hairpin Formation† R. Brian Dyer,*,‡ Shelia J. Maness, § Eric S. Peterson, | Stefan Franzen, § R. Matthew Fesinmeyer,A and Niels H. Andersen (Year: 2004).*

Biomater. Sci., 2017, 5, 2188 Peptides, polypeptides and peptide-polymer hybrids as nucleic acid carriers Marya Ahmed (Year: 2017).*

Michigami M, Takahashi K, Yamashita H, Ye Z, Nakase I, Fujii I (2021) A "ligand-targeting" peptide-drug conjugate: Targeted intracellular drug delivery by VEGF-binding helix-loop-helix peptides (Year: 2021).*

Int. J. Mol. Sci. 2021, 22, 12122. The Importance of 6-Aminohexanoic Acid as a Hydrophobic, Flexible Structural Element Agnieszka Markowska 1,*, Adam Roman Markowski 2 and Iwona Jarocka-Karpowicz. (Year: 2021).*

PLoS One. Feb. 25, 2021;16(2):e0247045. doi: 10.1371/journal.pone.0247045. eCollection 2021. Supplementary S7 (Year: 2021).*

* cited by examiner

*Primary Examiner* — Melissa L Fisher
*Assistant Examiner* — Archana Varadaraj
(74) *Attorney, Agent, or Firm* — DUANE MORRIS LLP; Gregory M. Lefkowitz; Brandon A. Chan

(57) ABSTRACT

The present disclosure provides a fusion peptide, a peptide-molecule conjugate containing the same, and a composition for nucleic acid delivery containing the same. The fusion peptide and the peptide-molecule conjugate containing the same of the present disclosure are expected to be used as a carrier for gene therapy intended for gene editing or treatment of diseases by delivering nucleic acids to cells or organs because it can be used for effective and safe delivery of nucleic acid materials and can be stored for a long time of 13 weeks or longer without structural destruction of the nucleic acids under harsh conditions.

20 Claims, 73 Drawing Sheets

Specification includes a Sequence Listing.

*hydrophilic-a-b-c-hydrophilic*

Ac-(PEG8)-AELAALEAELAALE-GGG-K-GGG-KLAALKAKLAALKAG-(PEG8)-$NH_2$

Hydrophilic *a* *b* *c* Hydrophilic

Ac-(PEG8)-AELAALEAELAALE-(Ahx)$_2$-K-(Ahx)$_2$-KLAALKAKLAALKAG-(PEG8)-NH$_2$

Ac-(PEG8)-AELAALEAELAALE-Ado-K-Ado-KLAALKAKLAALKAG-(PEG8)-$NH_2$

Glucose-(PEG8)-AELAALEAELAALE-(Ahx)$_2$-K-(Ahx)$_2$-KLAALKAKLAALKAG-(PEG8)-NH$_2$ Glucose-(PEG8)-AELAALEAELAALE-(Ahx)$_2$-K-(Ahx)$_2$-KLAALKAKLAALKAG-(PEG8)-K($^N$Glucose)-NH$_2$ Glucose-GS-AELAALEAELAALE-$(Ahx)_2$-K-$(Ahx)_2$-KLAALKAKLAALKAG-K($^N$Glucose)-$NH_2$ Glucose-GS-AELAALEUEUELAALE-$(Ahx)_2$-K-$(Ahx)_2$-KLAALKUKUKLAALKAG-K($^{N}$Glucose)-$NH_2$ Glucose-GS-AELUALEAELAULE-$(Ahx)_2$-K-$(Ahx)_2$-KLUALKAKLAULKAG-K($^{N}$Glucose)-$NH_2$ Glucose-GS-AELUALEUELAULE-(Ahx)$_2$-K-(Ahx)$_2$-KLUALKUKLAULKAG-K($^N$Glucose)-$NH_2$ (+/− ratio = 1)

Nanotube diameter
17 nm

EMSA (12h incubation in DW, 25 °C)

ssDNA coating ssDNA (dT40) = 40 nt

| Lane | dT40 (pmol) | $(PEG8)_2$-AA-U0 (base ratio) | $(PEG8)_2$-AGlyA-U0 (base ratio) |
|---|---|---|---|
| 1 | - | - | - |
| 2 | 6.25 | - | - |
| 3 | 6.25 | (1:80) 10 nmol | |
| 4 | 6.25 | | (1:80) 10 nmol |
| 5 | 6.25 | (1:160) 20 nmol | |
| 6 | 6.25 | | (1:160) 20 nmol |
| 7 | 6.25 | (1:320) 40 nmol | |
| 8 | 6.25 | | (1:320) 40 nmol |
| 9 | 6.25 | (1:1280) 160 nmol | |
| 10 | 6.25 | | (1:1280) 160 nmol |

EMSA (12h incubation in DW, 25 °C)

ssDNA coating ssDNA (dT100) = 100 nt

| Lane | dT100 (pmol) | $(PEG8)_2$-AA-U0 (base ratio) | $Glc_2$-AA-U0 (base ratio) |
|---|---|---|---|
| 1 | | - | - |
| 2 | | (1:80) 25 nmol | - |
| 3 | | - | (1:80) 25 nmol |
| 4 | 6.25 | (1:120) 37.5 nmol | - |
| 5 | | - | (1:120) 37.5 nmol |
| 6 | | (1:140) 43.75nmol | - |
| 7 | | - | (1:140) 43.75 nmol |

EMSA (12h incubation in DW, 25 °C)

ssDNA coating ssDNA (dT100) ≈ 100 nt

| Lane | dT100 (pmol) | $Glc_1$-AA-U0 (base ratio) | $Glc_1$-TT-U0 (base ratio) | $Glc_1$-COOH-U0 (base ratio) |
|---|---|---|---|---|
| 1 | | - | - | - |
| 2 | | - | - | - |
| 3 | | (1:80) 25 nmol | - | - |
| 4 | 6.25 | - | (1:80) 25 nmol | - |
| 5 | | - | - | (1:80) 25 nmol |

EMSA (12h incubation in DW, 25 °C)

ssDNA coating ssDNA (dT100) = 100 nt

| Lane | dT100 (pmol) | $Glc_1$-AA-U0 (base ratio) | $Glc_2$-AA-U0 (base ratio) |
|---|---|---|---|
| 1 | - | - | - |
| 2 | 6.25 | - | - |
| 3 | | (1:10) 3.125 nmol | - |
| 4 | | - | (1:10) 3.125 nmol |
| 5 | | (1:20) 6.25 nmol | - |
| 6 | | - | (1:20) 6.25 nmol |
| 7 | | (1:30) 9.375 nmol | - |
| 8 | | - | (1:30) 9.375 nmol |
| 9 | | (1:40) 12.5 nmol | - |
| 10 | | - | (1:40) 12.5 nmol |

EMSA (12h incubation in DW, 25 °C)

| Lane | dT200 (pmol) | Glc2-AA-U2 (base ratio) |
|---|---|---|
| 1 | | - |
| 2 | | (1:40) 25 nmol |
| 3 | 6.25 | (1:50) 31.25 nmol |
| 4 | | (1:60) 37.5 nmol |
| 5 | | (1:70) 43.75 nmol |

| Lane | dT200 (pmol) | Glc2-AA-U4 (base ratio) |
|---|---|---|
| 6 | | - |
| 7 | | (1:30) 18.75 nmol |
| 8 | 6.25 | (1:40) 25 nmol |
| 9 | | (1:50) 31.25 nmol |
| 10 | | (1:60) 37.5 nmol |

| Lane | dT200 (pmol) | Glc2-AA-U6 (base ratio) |
|---|---|---|
| 11 | | - |
| 12 | | (1:20) 12.5 nmol |
| 13 | 6.25 | (1:30) 18.75 nmol |
| 14 | | (1:40) 25 nmol |
| 15 | | (1:50) 31.25 nmol |

EMSA (12h incubation in DW, 25 °C)

ssDNA coating ssDNA (dT200) = 200 nt

| Lane | dT200 (pmol) | R-AA-Glc-U8 (base ratio) | R-TT-Glc-U8 (base ratio) |
|---|---|---|---|
| 1 | 6.25 | (1:60) 37.5 nmol | - |
| 2 | 6.25 | - | (1:60) 37.5 nmol |

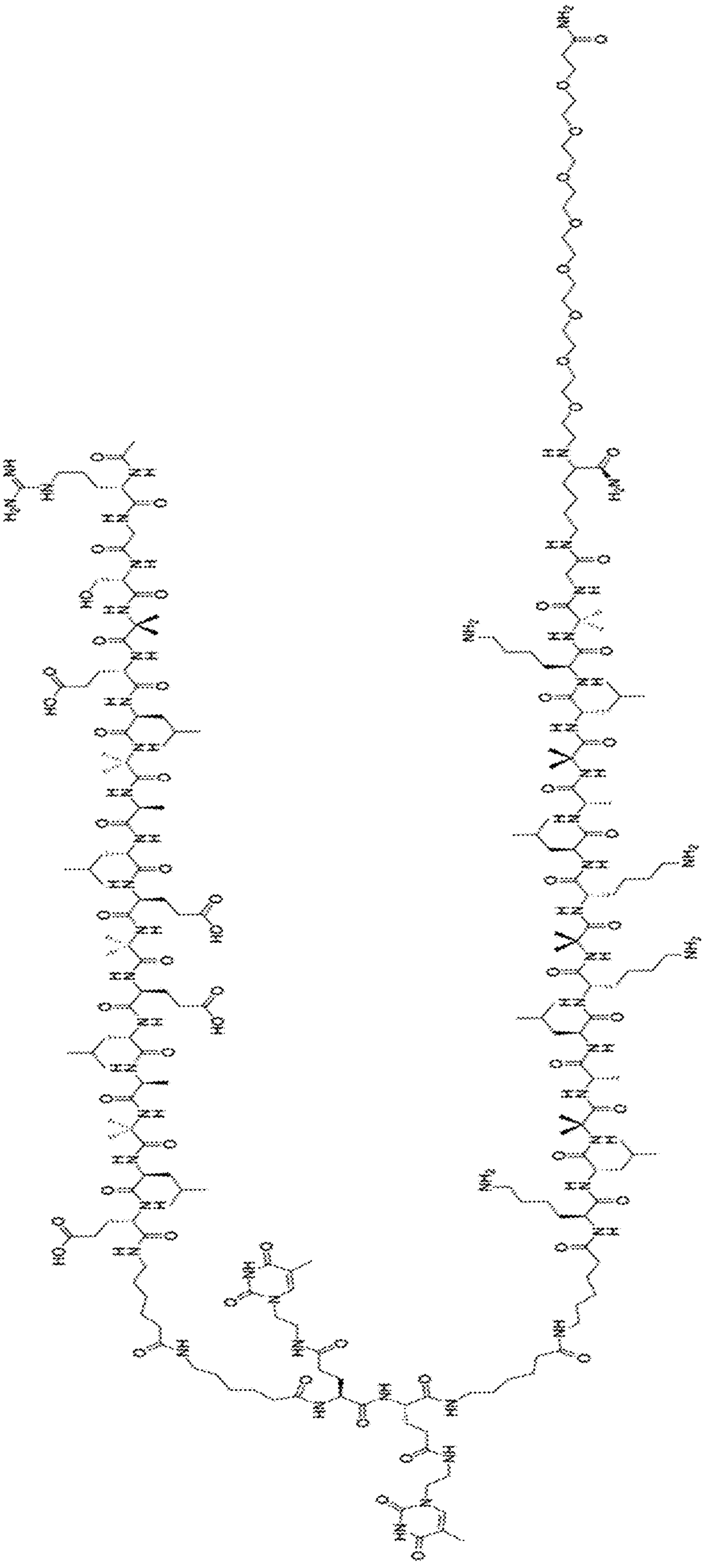
FOG. 41A

| Lane | dT200 (pmol) | R-TT-PEG8-U8 (base ratio) |
|---|---|---|
| 1 | 6.25 | - |
| 2 | | (1:40) 25 nmol |
| 3 | | (1:50) 31.25 nmol |
| 4 | | (1:60) 37.5 nmol |

| Lane | dT200 (pmol) | R-TT-(PEG8)$_2$-U8 (base ratio) |
|---|---|---|
| 5 | 6.25 | (1:40) 25 nmol |
| 6 | | (1:50) 31.25 nmol |
| 7 | | (1:60) 37.5 nmol |

| Lane | dT200 (pmol) | S-TT-PEG8-U8 (base ratio) |
|---|---|---|
| 8 | 6.25 | (1:30) 18.75 nmol |
| 9 | | (1:40) 25 nmol |
| 10 | | (1:50) 31.25 nmol |
| 11 | | (1:60) 37.5 nmol |
| 12 | | (1:100) 62.5 nmol |

ssDNA coating ssDNA (dT200) = 200 nt

EMSA (12h incubation in DW, 25 °C)

mRNA coating mRNA = 996 nt

| Lane | Total mole | Lane | Total mole |
|---|---|---|---|
| | TT47% CC21% GG26% AA6% | | TT47% CC21% GG26% AA6% |
| 1 | - | 9 | 8 |
| 2 | 1 | 10 | 9 |
| 3 | 2 | 11 | 10 |
| 4 | 3 | 12 | 11 |
| 5 | 4 | 13 | 12 |
| 6 | 5 | 14 | 13 |
| 7 | 6 | 15 | 14 |
| 8 | 7 | 16 | 15 |

EMSA (12h incubation in DW, 25 °C)

CD spectroscopy

*cyc*-R(AU)$A_5$-Ga 5 μM / 50 μM (in $H_2O$)

*lin*-R(AU)$A_5$-Ga 5 μM / 50 μM (in $H_2O$)

Sample preparation

-peptide solution in $H_2O$.
-vortex, cup-horn sonicate peptide at 30°C for 20 min.
-2mm light path quartz glass cell, 20 °C measurement.

| MRE ratio (α-helix) | *lin*-R(AU)$A_5$-Ga | | *cyc*-R(AU)$A_5$-Ga | |
|---|---|---|---|---|
| [θ] ($222_{nm}$/$208_{nm}$) | 5 μM | 50 μM | 5 μM | 50 μM |
| | 1.0188 | 1.0338 | 1.0281 | 1.0351 |

[θ] >1,
coiled coil (associated α-helix) conformation

FUSION PEPTIDES CONTAINING DIMERIC ALPHA-HELICES, PEPTIDE-MOLECULAR CONJUGATES CONTAINING THE SAME AND NUCLEIC ACID DELIVERY COMPOSITIONS CONTAINING THE SAME

CROSS-REFERENCE TO RELATED APPLICATION

This application claims priority to Korean Patent Application No. 10-2022-0034890, filed on Mar. 21, 2022, and Korean Patent Application No. 10-2023-0023099, filed on Feb. 21, 2023, and all the benefits accruing therefrom under 35 U.S.C. § 119, the contents of which in its entirety are herein incorporated by reference.

SEQUENCE LISTING

The instant application contains a Sequence Listing which has been submitted electronically in a computer readable Sequence Listing XML format and is hereby incorporated by reference in its entirety. Said computer readable Sequence Listing in XML format was created on Mar. 15, 2023, is named G1035-23901_SequenceListing.xml and is 22,669 bytes in size.

BACKGROUND

1. Field

The present disclosure relates to a fusion peptide, a peptide-molecule conjugate containing the same, and a composition for nucleic acid delivery containing the same. The present disclosure was completed by using an artificial peptide as a gene carrier that can be used for gene therapy, etc. and identifying that it can store and maintain a nucleic acid safely from harmful factors as a carrier of the nucleic acid and can enhance the effect of the nucleic acid by increasing the efficiency of intracellular delivery.

2. Description of the Related Art

Nucleic acids are used in various fields, including vaccination, gene therapy, protein replacement therapy, treatment of genetic diseases, etc. There are some prerequisites for successful therapy using genetic materials such as nucleic acids. First, gene delivery technology capable of safely and effectively introducing the gene necessary for therapy into the desired tissues or cells and expressing the gene should be ensured. In addition, high stability is necessary to ensure the maintenance of the efficiency of genetic materials against degradation of specific nucleic acid molecules including RNAs and to ensure stable storage and global distribution. Furthermore, the carrier for gene delivery should have no toxicity in the human body and should be degraded effectively at the target site for selective delivery of the genetic material to the target cell.

In general, drugs are distributed in dry forms. However, for nucleic acids used in gene therapy, which are anionic substances, the development of a new delivery technology is necessary because they are vulnerable to surrounding environments such as temperature, chemicals, etc. and are easily degraded by various enzymes in the body.

The delivery technologies developed thus far can be largely classified into viral vectors and non-viral vectors. Although viral vectors are known to have relatively higher intracellular delivery efficiency than non-viral vectors because they utilize the intrinsic intracellular penetration mechanism of viruses that infect human cells, the difficulty in long-term administration due to immune response and the possibility of viral replication cannot be ruled out completely.

A variety of gene delivery technologies utilizing various conjugates have been developed to make up for the disadvantages and risks of the viral vectors. For instance, a technology of synthesizing a cationic lipid and forming an ionic bonding complex for gene delivery has been developed. However, there are many problems such as the cytotoxicity of cationic lipids, the difficulty in large-scale production of cationic lipids, low stability during storage and distribution, low nucleic acid loading capacity, etc.

In this regard, a technology of utilizing chitosan, which is a naturally occurring cationic polymer, as a gene carrier is known. The technology is advantageous in terms of low toxicity and high stability because a gene is delivered into a cell by ionically binding the gene to chitosan. However, since the gene bound to the chitosan-gene complex can be detached easily at physiological pH of 7.4 due to weakened cationic charge, the complex may be degraded in vivo and the efficiency of intracellular gene delivery is very low.

Accordingly, in order to solve the above-described problems of carriers of genetic materials such as nucleic acids, it is necessary to find a method for improving the stability of the lipid nanoparticle (LNP) platform or develop a completely new type of nucleic acid delivery platform.

SUMMARY

The inventors of the present disclosure have designed a hairpin-structured peptide containing a dimeric α-helical peptide, which is prepared into a nanostructure such as a nanotube, etc. as, when mixed with a nucleic acid material, it forms a self-assembled monolayer that surrounds the surface of the nucleic acid material. They have identified that the nanostructure can be used as a carrier of a nucleic acid material, i.e., a vaccine carrier, because it protects the nucleic acid material from external environment and improves intracellular delivery rate, and have completed the present disclosure.

The present disclosure is directed to providing a fusion peptide having a hairpin structure.

The present disclosure is also directed to providing a fusion peptide-based peptide-molecule conjugate.

The present disclosure is also directed to providing a composition for nucleic acid delivery, which contains a peptide-molecule conjugate as an active ingredient.

However, the technical problems to be solved by the present disclosure are not described to those described above, and other problems not mentioned above will be clearly understood by those skilled in the art from the following description.

The present disclosure provides a fusion peptide consisting of: (a) a first peptide represented by any sequence selected from SEQ ID NO 1 and SEQ ID NOS 3-8; (b) a gene-binding region consisting of 1-4 residue peptides containing a lysine (K) residue, an arginine (R) residue or a glutamic acid (E) residue; (c) a second peptide represented by any sequence selected from SEQ ID NO 2 and SEQ ID NOS 3-8; (d) a first linker bound between the first peptide and the gene-binding region; and (e) a second linker bound between the gene-binding region and the second peptide.

The first peptide and the second peptide may have an α-helical secondary structure and may be arranged side by side with the gene-binding region at the center.

The first peptide and the second peptide may provide dynamic plasticity by forming sliding, scissoring or bending arrangement through non-covalent interaction.

Each of the first linker and the second linker may be independently any one selected from a group consisting of GG, GGG, Ahx (6-aminohexanoic acid), $Ahx_2$, Ado (12-aminododecanoic acid) and 8Ado (8-amino-3,6-dioxaoctanoic acid).

Electrostatic interaction may be formed between the glutamic acid (E) of the first peptide and the lysine (K) of the second peptide, and hydrophobic interaction may be formed between the leucine (L) of the first peptide and the second peptide.

One or more nucleobase selected from adenine, cytosine, guanine, thymine and uracil may be covalently bonded to a peptide side chain of the gene-binding region (b).

When the first peptide is a sequence represented by SEQ ID NO 1, the second peptide may be a sequence represented by SEQ ID NO 2, and the fusion peptide may have a hairpin structure.

When the first peptide is any sequence of SEQ ID NOS 3-8, the second peptide may be any sequence selected from SEQ ID NOS 3-8, and the fusion peptide may have a linear or cyclic structure.

The gene-binding region (b) may bind to a negatively charged target through interaction.

The present disclosure also provides a peptide-molecule conjugate containing: i) the fusion peptide described above; and ii) a hydrophilic molecule bound to at least one or both of the terminals of the first peptide and the second peptide of the fusion peptide.

The hydrophilic molecules bound to the first peptide and the second peptide may be identical or different from each other, the hydrophilic molecule may be a hydrophilic polymer or a hydrophilic targeting ligand, the hydrophilic polymer may be any one selected from a group consisting of polyethylene glycol, Pluronic, pullulan, hyaluronic acid, glycol chitosan, heparin, chondroitin sulfate, fucoidan, dextran and a derivative thereof, and the hydrophilic targeting ligand may be one or more selected from a group consisting of a carbohydrate, an aptamer, a vitamin, folic acid, a hexosamine and a peptide.

The peptide-molecule conjugate may have a helicity of 0.8-0.9.

The peptide-molecule conjugate may have a molecular length of 5-6 nm.

The peptide-molecule conjugate may form a self-assembled monolayer that surrounds a nucleic acid material through non-covalent bond with the nucleic acid material.

The present disclosure also provides a composition for nucleic acid delivery, which contains the peptide-molecule conjugate as an active ingredient.

The nucleic acid may be a DNA or an RNA.

The composition may further contain one or more selected from a group consisting of amantadine, ammonium chloride, polyethylenimine and chloroquine.

A mixing ratio of the peptide-molecule conjugate and the nucleic acid may be 0.1-10:1 based on charge (+/− ratio).

The peptide-molecule conjugate and the nucleic acid may form, through self-assembly, a nanostructure consisting of: a core containing the nucleic acid; and a self-assembled monolayer surrounding the core.

The nanostructure may be a nanotube.

The monolayer may have an average thickness of 5-7 nm.

The present disclosure relates to a peptide of a new structure for storage and delivery of a nucleic acid material. The inventors of the present disclosure have formed a nanostructure through self-assembly of the mRNA of the fluorescent protein gene GFP, and have confirmed the expression of the fluorescent protein in cells treated with the nanostructure. That is to say, it was confirmed that the nucleic acid material mRNA is delivered easily into cells and can be stored without the breakdown of the mRNA under the condition of high-concentration urea, long-term storage and RNase.

Accordingly, the fusion peptide and the peptide-molecule conjugate containing the same of the present disclosure are expected to be used as a carrier for gene therapy intended for gene editing or treatment of diseases by delivering nucleic acids to cells or organs because it can be used for effective and safe delivery of nucleic acid materials and can be stored for a long time of 13 weeks or longer without structural destruction of the nucleic acids under harsh conditions.

BRIEF DESCRIPTION OF THE DRAWINGS

FIG. 12A shows a result of analyzing the thermodynamic stability of nanostructures depending on type.

FIG. 12B shows the difference in stiffness and irregularity of a double-stranded nucleic acid (dsNA) and a single-stranded nucleic acid (ssNA), and FIG. 12C shows a result of analyzing a dimeric α-helical block (body domain) of the peptide-molecule conjugate, consisting of an α-helical coiled coil formed from the first and second peptides, using a helical wheel diagram. FIG. 12D schematically shows the principle of the dynamic plasticity of a peptide-molecule conjugate (SAB), and FIG. 12E shows the structure of a peptide-molecule conjugate (SAB) formed from coating of a nucleic acid (dsDNA or mRNA) and a surface of a nanoparticle (AuNP) through self-assembly.

FIG. 13A shows the structure of peptide-molecule conjugates (SAB1 to SAB3), and FIG. 13B shows the CD spectra of the peptide-molecule conjugates (SAB1 to SAB3) in an aqueous solution at 20° C. The numerical values in parentheses indicate helicities represented by $[\theta]_{222}/[\theta]_{208}$ ratios. FIG. 13C shows the negative-stain TEM image of a self-assembly nanostructure formed as a peptide-molecule conjugate of Example 3 (SAB3) surrounds the surface of a gold nanoparticle (AuNP). The insert image was obtained after adding peptide-molecule conjugates (SAB1 to SAB3) to a gold nanoparticle aqueous solution. FIG. 13D schematically shows the formation of a self-assembled monolayer (SAM) by a peptide-molecule conjugate of Example 3 (SAB3) on the surface of a gold nanoparticle (AuNP).

FIG. 20 also shows the CD spectra of the peptide-molecule conjugate of Example 6 (SAB-$g_3$) and the EGFP mRNA, denoted as 'SAB-$g_3$' and 'EGFP mRNA', respectively.

FIG. 22A is a TEM image showing the diameter and monolayer thickness of a nanostructure of SAB-$g_3$ and EGFP mRNA (+/−=0.25), FIG. 22B shows the structural model of the nanostructure of SAB-$g_3$ and EGFP mRNA (+/−=0.25), and FIG. 22C schematically shows the formation of the nanostructure of SAB-$g_3$ and EGFP mRNA (+/−=0.25).

In FIG. 33B, the lane 1 indicates a naked DNA, and the lane 2 indicates an ssDNA/peptide complex.

FIG. 41A shows the structure of a peptide-molecule conjugate of Example 22 (R-TT-PEG8-U8)

DETAILED DESCRIPTION

Figure 1:
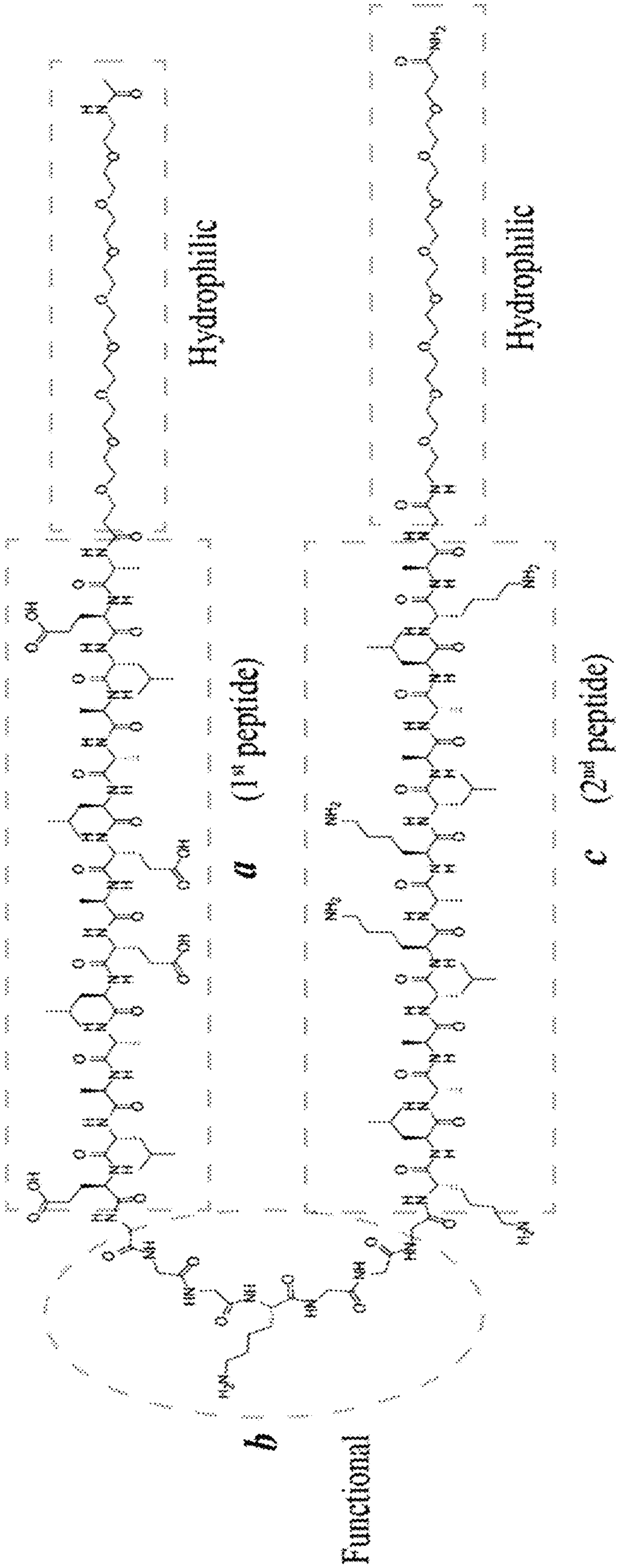
FIGS. 1-9 show the chemical structure of peptide-molecule conjugates prepared in Examples 1-9 (SAB1 to SAB3, SAB-$g_1$ to SAB-$g_6$).
Figure 2:
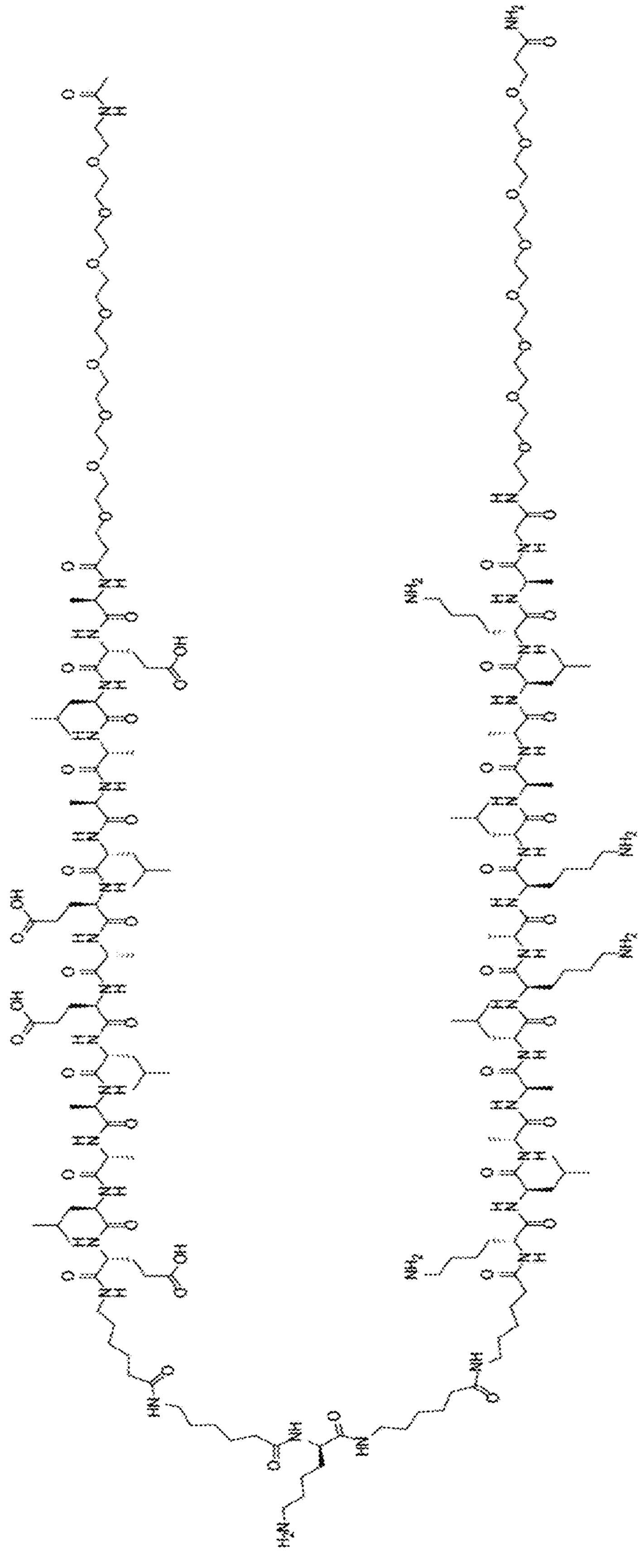
Figure 3:
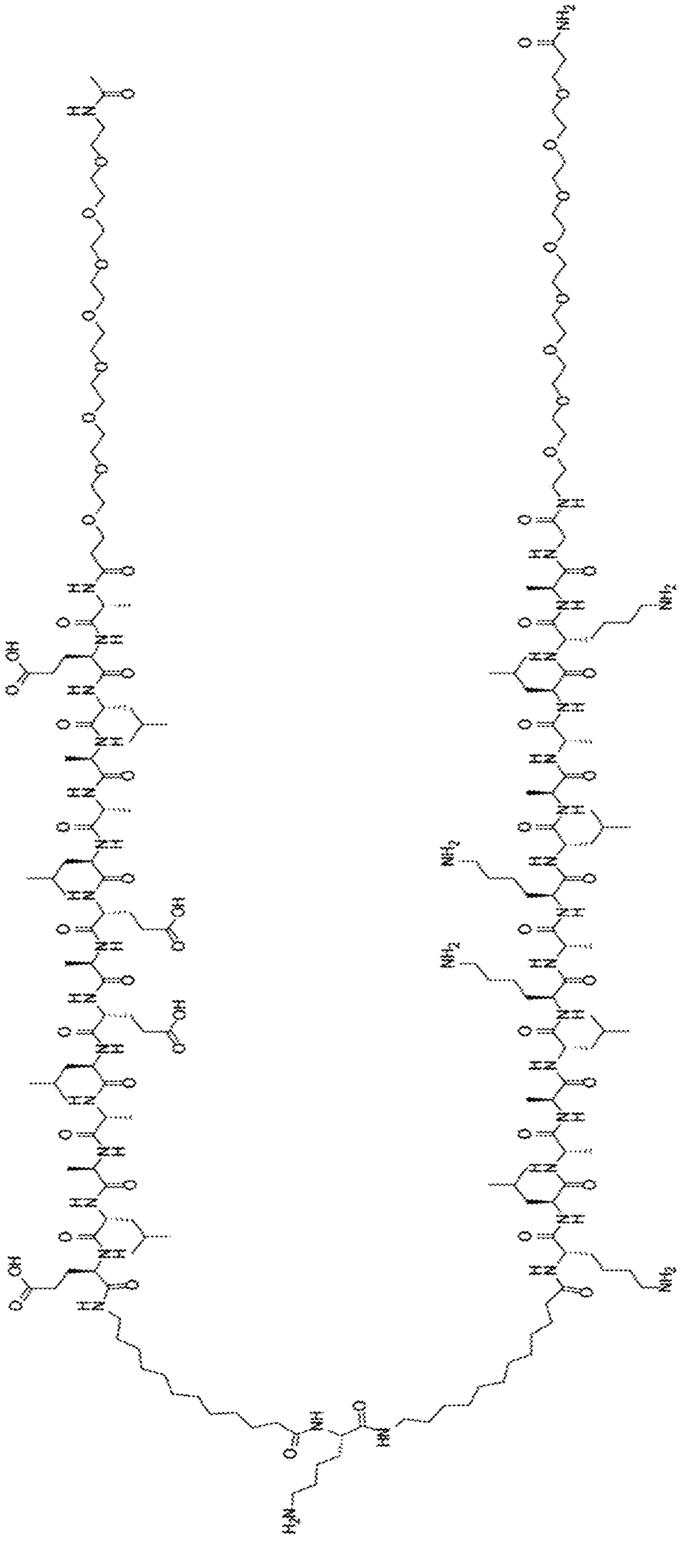
Figure 4:
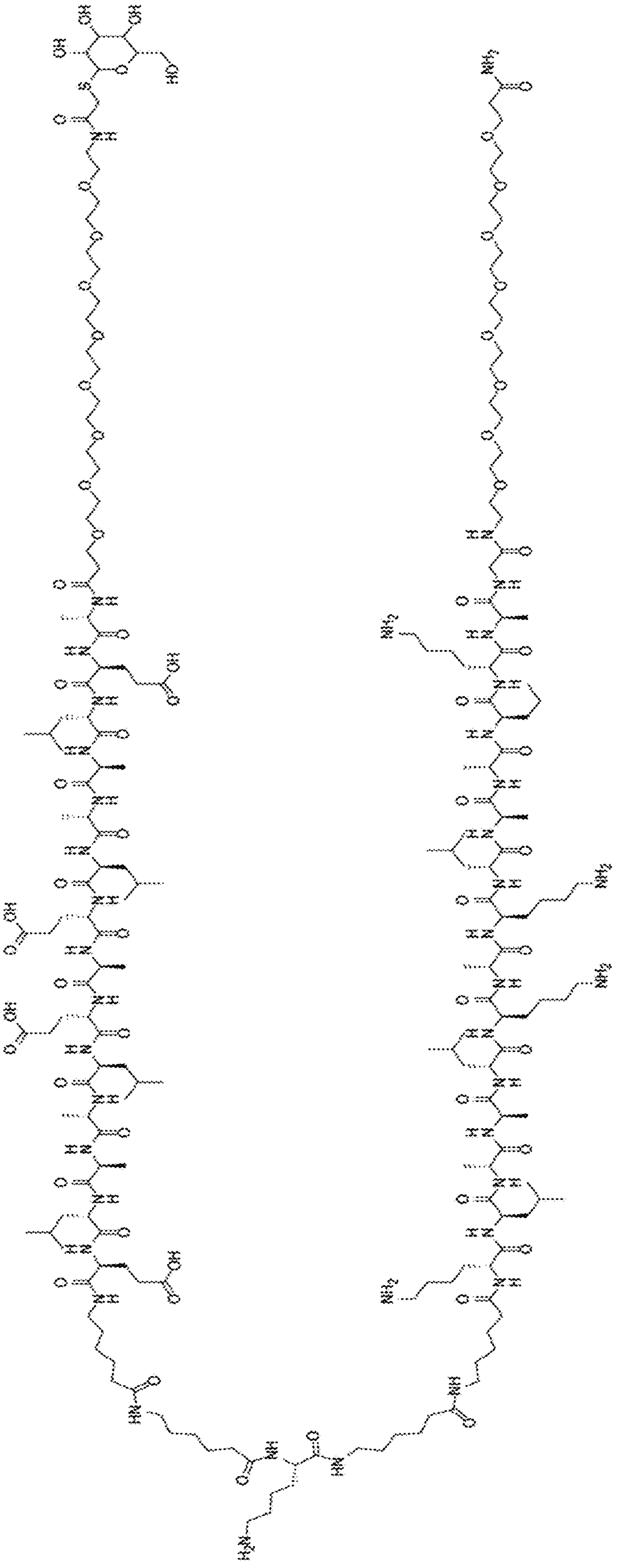
Figure 5:
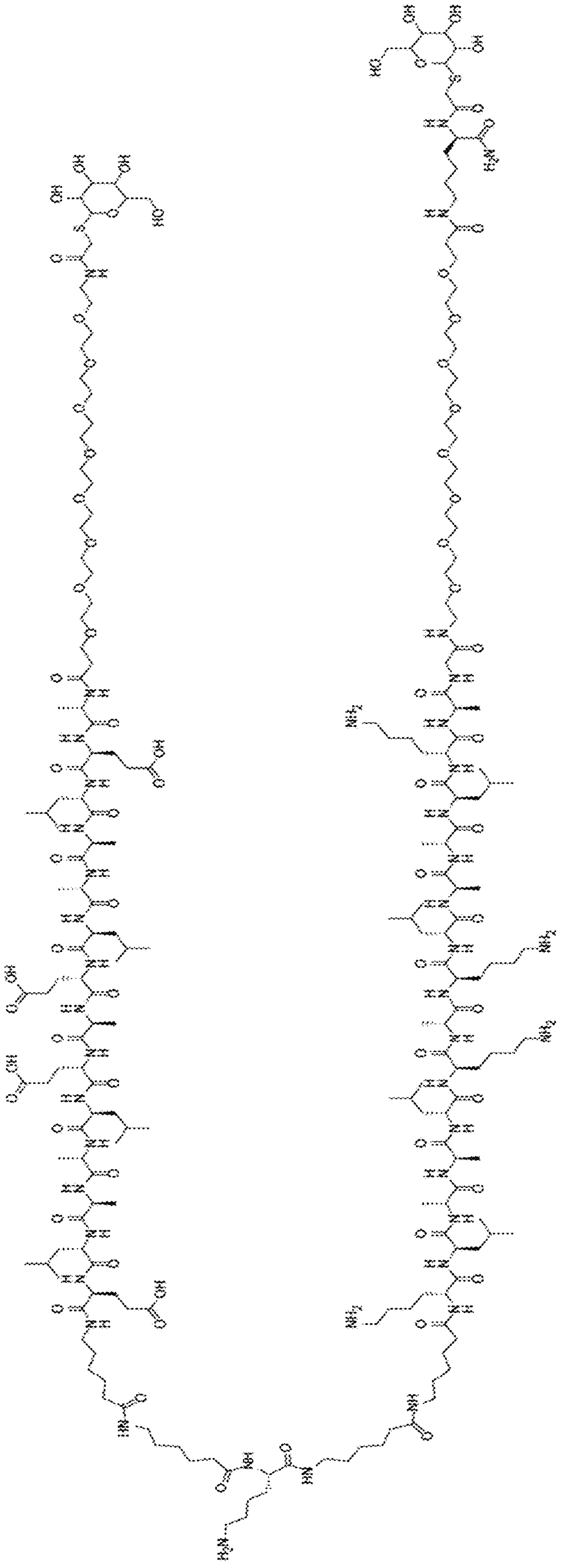
Figure 6:
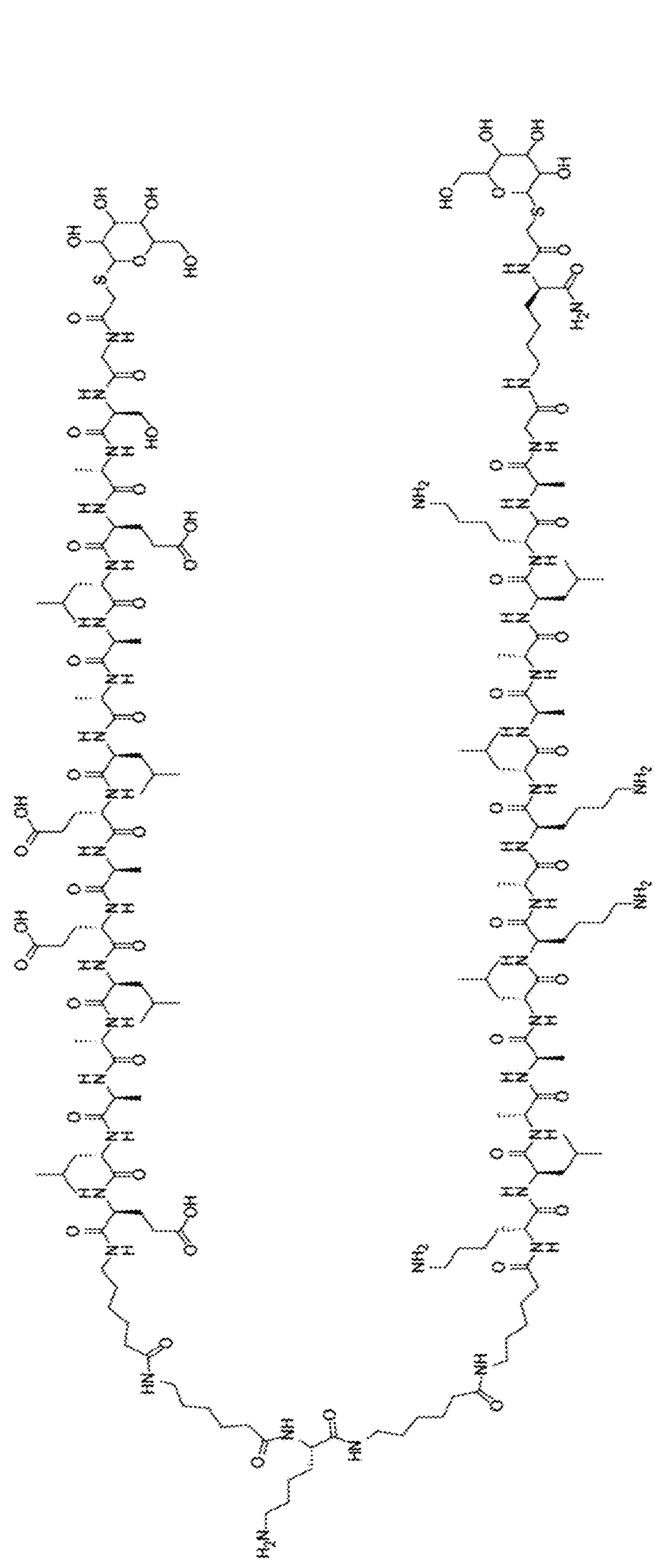
Figure 7:
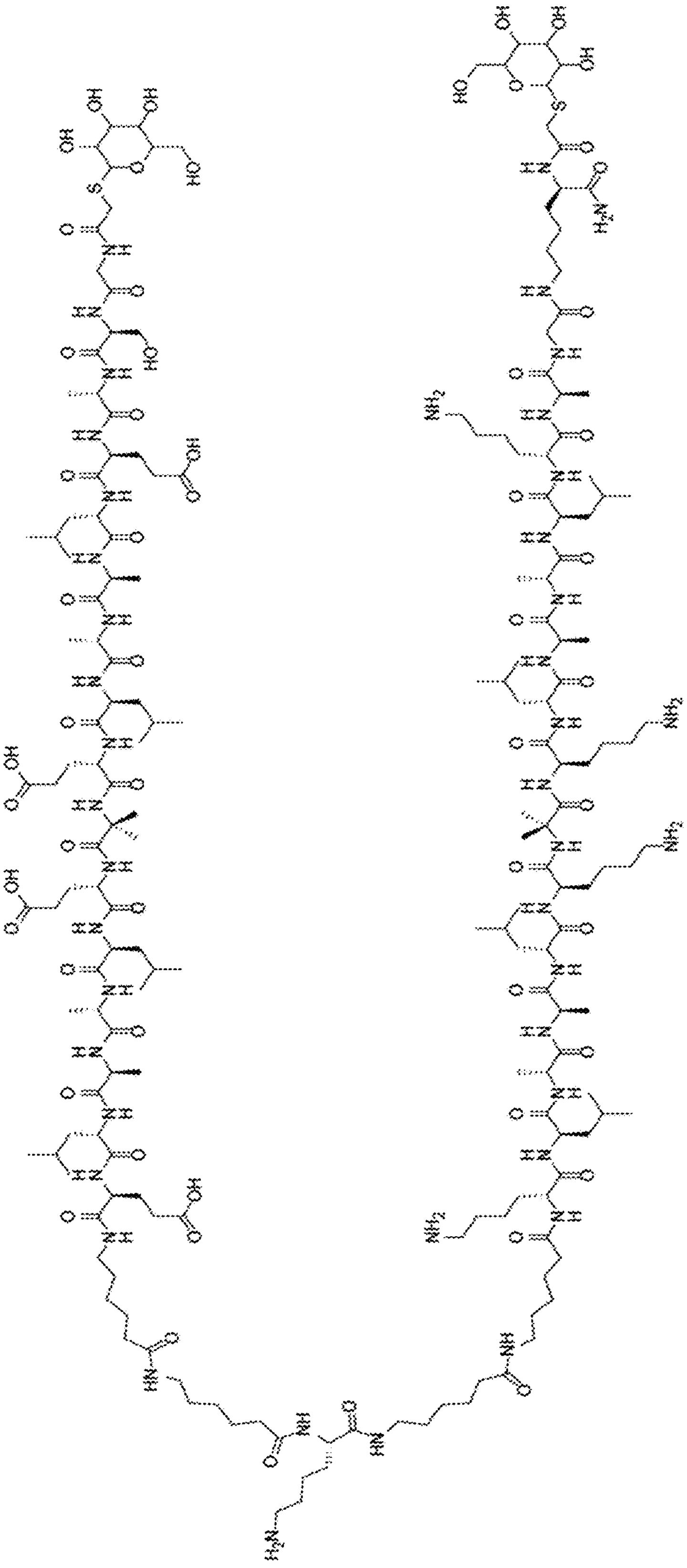
Figure 8:
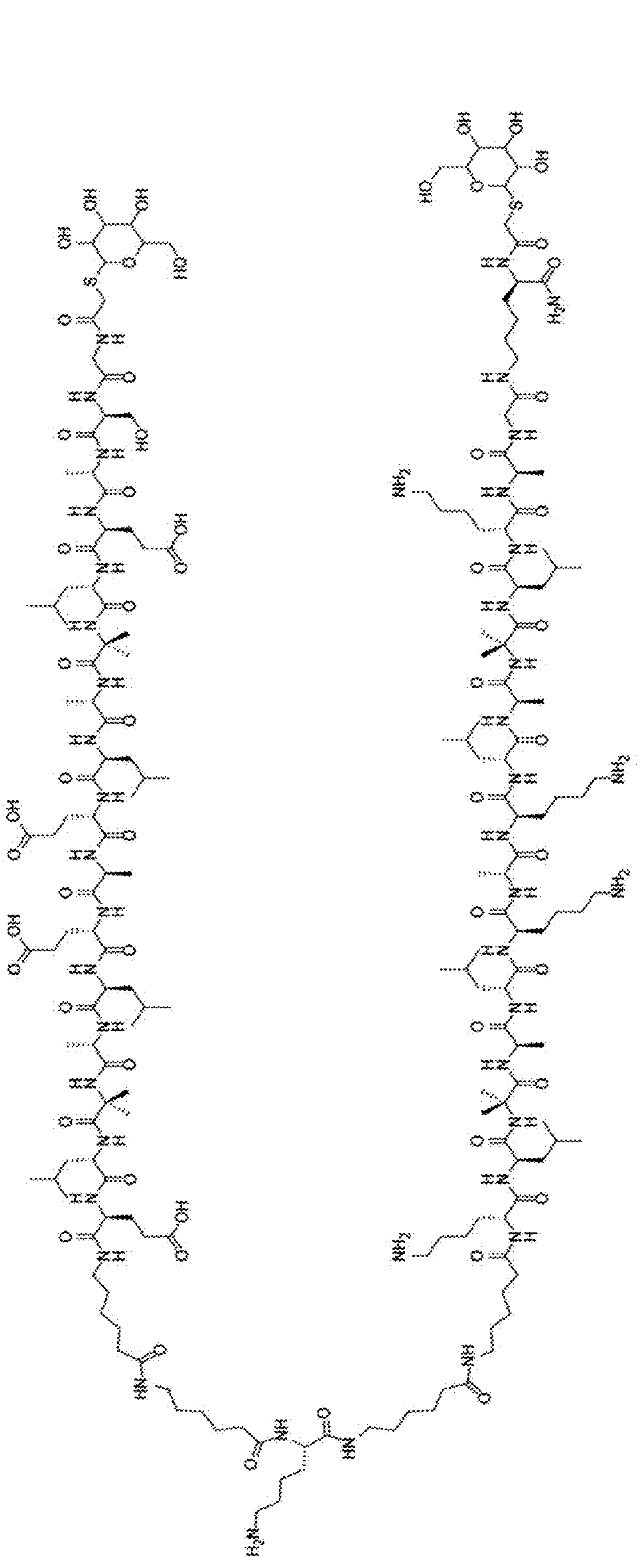
Figure 9:
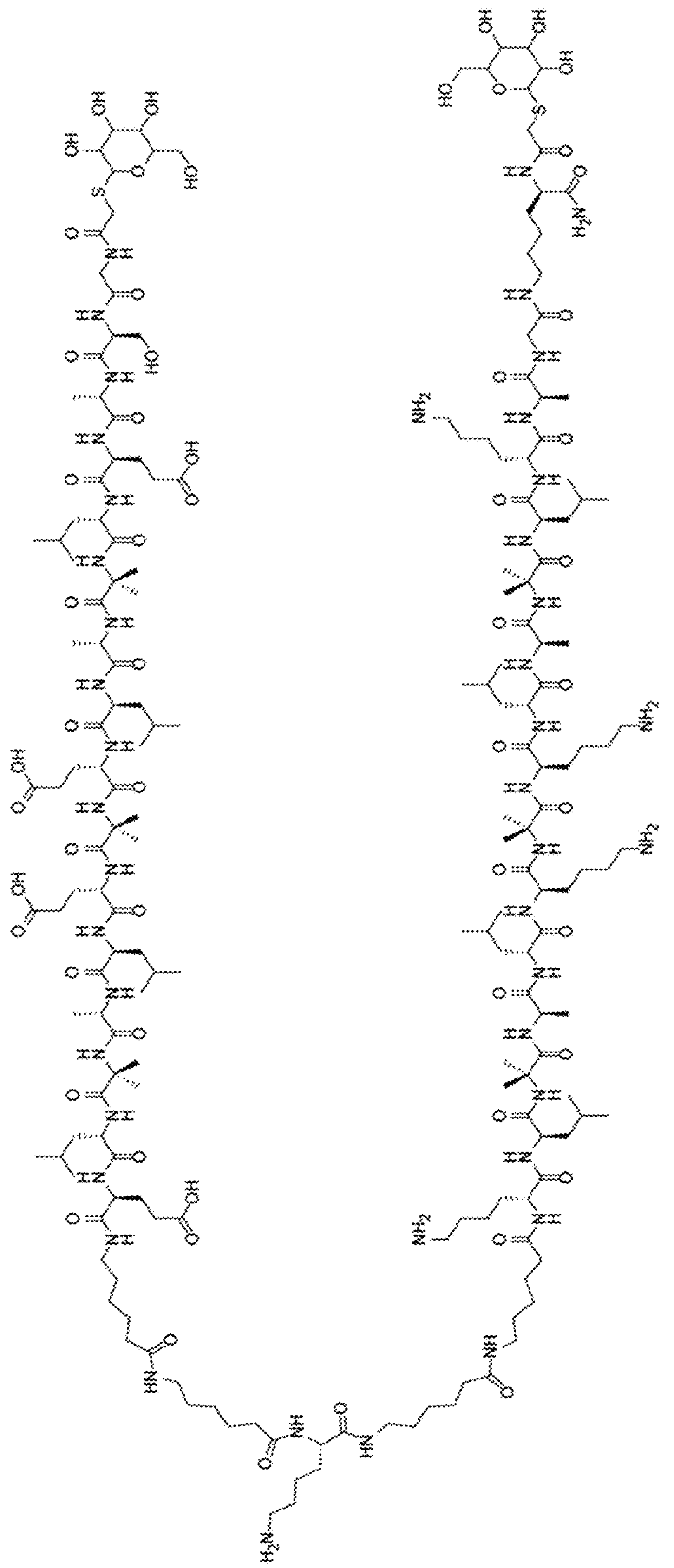

Since nucleic acid materials such as mRNAs, etc. are destroyed easily when exposed to the external environment, carriers are necessary for stable storage and transport. However, because the nucleic acid materials such as mRNAs, etc. are flexible and have irregular structures, it is very difficult to develop a carrier or a platform that allows secure storage while maintaining their structures and activities.

At present, lipid nanoparticles (LNPs) have been developed as carriers for nucleic acid materials such as mRNAs, etc. However, they are greatly limited in storage and transport because stability is ensured at low temperatures (−80 to −20° C.) only. In addition, because the lipid nanoparticles are easily degraded in the body before reaching the target, the efficacy of the nucleic acid materials cannot be exerted enough. Furthermore, as the single-stranded nucleic acids (ssNAs) such as mRNAs, which are fibrous multivalent anions consisting of hundreds to thousands of nucleotides, are stuffed into spherical nanostructure, there are problems such as penalties in entropy, electrostatic repulsion, etc.

In order to solve these problems, the inventors of present disclosure have made efforts to design a new high-functional peptide capable of packaging the fibrous structure of nucleic acid materials such as mRNAs in unfolded states while providing stability (thermal stability, etc.) against external environment and a conjugate based thereon, and have completed the present disclosure.

The peptide according to the present disclosure and the conjugate containing the same can provide a carrier of a new structure that forms a self-assembled monolayer (SAM) on the surface of nucleic acid having a fibrous structure despite the flexible and irregular structure of the nucleic acid material such as mRNA.

The peptide or the conjugate containing the same according to the present disclosure is also referred to as a 'self-adjusting building block' or a 'SAB' because it forms a supramolecular composite through self-assembly with a nucleic acid material. It can form a self-assembled monolayer not only for nucleic acid materials such as mRNAs but also for organic and inorganic nanoparticles such as gold nanoparticles. In addition, because volume fraction and structure can be controlled dynamically depending on the molecular structure or surface structure of the target, it can store any negatively charged material stably from external environment by forming a self-assembled monolayer.

Hereinafter, the present disclosure is described in detail referring to the attached drawings and specific exemplary embodiments.

In the present disclosure, "A and/or B" means "A and B, or A or B".

In the present disclosure, the 'self-assembly' is a precise and convenient "bottom-up" approach for designing ordered 3-dimensional and biocompatible nanobiomaterials. Renewable macromolecular nanostructures can be obtained from highly specific interactions between building blocks. These intermolecular associations organize supramolecular structures mainly by non-covalent electrostatic interaction, hydrogen bonding, van der Waals force, etc. Supramolecular chemistry or biology gathers a vast body of 2D or 3D complex structures and entities formed by association of chemical or biological species. These associations are governed by the principles of molecular complementarity or molecular recognition and self-assembly. The knowledge of the rules of intermolecular association can be used to design polymolecular assemblies in the form of membranes, films, layers, micelles, tubules or gels for a variety of biomedical or technological applications (J.-M. Lehn, *Science,* 295, 2400-2403, 2002).

In an aspect, the present disclosure relates to a fusion peptide consisting of: (a) a first peptide represented by any sequence selected from SEQ ID NO 1 and SEQ ID NOS 3-8; (b) a gene-binding region consisting of 1-4 residue peptides containing a lysine (K) residue, an arginine (R) residue or a glutamic acid (E) residue; (c) a second peptide represented by any sequence selected from SEQ ID NO 2 and SEQ ID NOS 3-8; (d) first linker bound between the first peptide and the gene-binding region; and (e) a second linker bound between the gene-binding region and the second peptide.

[SEQ ID NO 1]
$X_1$-E-L-$X_2$-$X_3$-L-E-$X_4$-E-L-$X_5$-$X_6$-L-E

[SEQ ID NO 2]
K-L-$X_7$-$X_8$-L-K-$X_9$-K-L-$X_{10}$-$X_{11}$-L-K-$X_{12}$

[SEQ ID NO 3]
AUAUAUAU

[SEQ ID NO 4]
AUAUAUAUA

[SEQ ID NO 5]
AUAUAUAUAU

[SEQ ID NO 6]
AUAUAUAUAUA

[SEQ ID NO 7]
AUAUAUAUAUAU

[SEQ ID NO 8]
AUAUAUAUAUAUA

In SEQ ID NOS 1 and 2, each of $X_1$ to $X_{12}$ is independently any one selected from a group consisting of alanine (A), Aib (2-aminoisobutyric acid) and leucine (L).

In the fusion peptide according to the present disclosure, the first peptide α-helical block and the second peptide α-helical block have an α-helical secondary structure and may be arranged side by side with the linker at the center. The first peptide α-helical block and the second peptide α-helical block arranged side by side forms a hairpin structure through hydrophobic interaction of amino acid molecules.

Specifically, the fusion peptide contains the dimeric α-helical block consisting of a first peptide represented by any sequence selected from SEQ ID NO 1 and SEQ ID NOS 3-8 (a), and the second peptide represented by any sequence selected from SEQ ID NO 2 and SEQ ID NOS 3-8 (c). The dimeric α-helical block has an α-helical secondary structure and is arranged side by side with gene-binding region (b) at the center. The dimeric α-helical block consisting of the first and second peptides arranged side by side forms a hairpin structure through hydrophobic interaction between two peptide amino acid molecules.

In the fusion peptide, the dimeric α-helical block consisting of the first and second peptides exhibits hydrophobicity and is involved in the formation of a hairpin structure. The first peptide and the second peptide may provide dynamic plasticity upon binding with drugs, gold nanoparticles or nucleic acid molecules by forming sliding, scissoring or bending arrangement through non-covalent interaction.

In the fusion peptide, the gene-binding region (b) is a binding region which is involved in the formation of a flexible binding of the dimeric α-helical block consisting of the first and second peptides and the formation of binding with various negatively charged molecules (drugs, gold nanoparticles or nucleic acid molecules).

The structure of the dimeric α-helical block may be adjusted appropriately depending on the first and second peptides. Specifically, when the first peptide is a sequence represented by SEQ ID NO 1, the second peptide may be a sequence represented by SEQ ID NO 2, and the fusion peptide may have a hairpin structure.

When the first peptide is any sequence of SEQ ID NOS 3-8, the second peptide may be any sequence selected from SEQ ID NOS 3-8, and the fusion peptide may have a linear or cyclic structure.

In SEQ ID NOS 1 and 2, each of $X_1$ to $X_{12}$ is independently any one selected from a group consisting of alanine (A), Aib (2-aminoisobutyric acid) and leucine (L).

In an exemplary embodiment of the present disclosure, the first peptide may be any one selected from SEQ ID NOS 9-13, and the second peptide may be any one selected from SEQ ID NOS 14-17.

[SEQ ID NO 9]
AELAALEAELAALE

[SEQ ID NO 10]
AELUALEAELAULE

[SEQ ID NO 11]
AELUALEAELAULE

[SEQ ID NO 12]
AELUALEUELAULE

[SEQ ID NO 13]
UELUALEUELAULE

[SEQ ID NO 14]
KLAALKAKLAALKA

[SEQ ID NO 15]
KLUALKAKLAULKA

[SEQ ID NO 16]
KLUALKUKLAULKA

[SEQ ID NO 17]
KLUALKUKLAULKU

Electrostatic interaction may be formed between the glutamic acid (E) of the first peptide and the lysine (K) of the second peptide, and hydrophobic interaction may be formed between the leucine (L) of the first peptide and the second peptide.

The second peptide may further contain a third linker at its terminal. The third linker may be any one selected from a group consisting of G, GG, GGG, GS, GGS, GSG, GSS, GK, GGK, GKK, K and KK.

In the fusion peptide, the gene-binding region (b) may contain one or more of a lysine (K) residue, an arginine (R) residue or a glutamic acid (E) residue. Specifically, it may contain one to four of a lysine (K) residue, an arginine (R) residue or a glutamic acid (E) residue. More specifically, it may contain one or two of a lysine (K) residue, an arginine (R) residue or a glutamic acid (E) residue. Most specifically, it may contain one of a lysine (K) residue, an arginine (R) residue or a glutamic acid (E) residue.

One or more nucleobase selected from adenine, cytosine, guanine, thymine and uracil may be bound to the peptide side chain of the gene-binding region (b) through a covalent bond. Specifically, one or more nucleobase selected from adenine, cytosine, guanine, thymine and uracil may be bound per the peptide. More specifically, 1-10 nucleobases may be bound. Further more specifically, 1-5 nucleobases may be bound. Further more specifically, 1-2 nucleobases may be bound. Most specifically, one nucleobase may be bound.

Each of the first linker and the second linker may independently be any one selected from a group consisting of GG, GGG, Ahx (6-aminohexanoic acid), $Ahx_2$, Ado (12-aminododecanoic acid) and 8Ado (8-amino-3,6-dioxaoctanoic acid). The first linker and the second linker may be nonexistent. However, it is preferred that both the first linker and the second linker exist.

Although the first linker and the second linker may be identical to or different from each other, it is preferred that they are identical. The first linker and the second linker may further include any one selected from a group consisting of GG, GGG, Ahx (6-aminohexanoic acid), $Ahx_2$, Ado (12-aminododecanoic acid) and 8Ado (8-amino-3,6-dioxaoctanoic acid), specifically any one selected from a group consisting of GGG, Ahx (6-aminohexanoic acid), $Ahx_2$ and Ado (12-aminododecanoic acid). Since they provide space and flexibility so as to prevent interference by the peptide structure in the gene-binding region (b), it may be favorable to achieve the above conditions in order to attain structural activity.

The GG and GGG of the first linker and/or the second linker consist of less than four residues. It may be a sequence consisting of one or more glycine (G) residue, specifically two or three glycine (G) residues connected continuously.

In the fusion peptide according to the present disclosure, the first and second peptides have a dimeric α-helical block structure. The dimeric α-helical block has an α-helical structure consisting of one complete cycle as shown in the α-helical wheel diagram of FIG. 12C. Specifically, referring to FIG. 12C, glutamic acid (E)-leucine (L)-leucine (L)-glutamic acid (E) in the helical wheel structure of the first peptide are arranged to oppose the second peptide, and lysine (K)-leucine (L)-leucine (L)-lysine (K) in the helical wheel structure of the second peptide are arranged to oppose the first peptide. Accordingly, dynamic plasticity may be provided because electrostatic interaction is formed between the glutamic acid (E) of the first peptide and the lysine (K) of the second peptide and hydrophobic interaction is formed between the leucine (L) of the first peptide and the second peptide. Since the fusion peptide according to the present disclosure has superior dynamic plasticity, its 3D structure can be changed dynamically depending on the structural change caused by binding to negatively charged materials such as nucleic acid materials, gold nanoparticles, etc. Nanostructures are formed through the binding and self-assembly having superior mechanical properties.

Accordingly, because the fusion peptide according to the present disclosure has flexibility and stiffness at the same time and hydrophilic molecules with various functions can be introduced at the terminals of the first and second peptides, the fusion peptide can be utilized in various applications as a new peptide-based platform.

In another aspect, the present disclosure relates to a peptide-molecule conjugate containing: i) the fusion peptide described above; and ii) a hydrophilic molecule bound to at least one or both of the terminals of the first peptide and the second peptide of the fusion peptide.

The peptide-molecule conjugate according to the present disclosure may also be referred to as a multi-block self-assembling fusion peptide. The peptide-molecule conjugate has a multi-block structure formed by binding of one block molecule. The block molecule may be: a) a first peptide; b) gene-binding region; c) a second peptide; d) a first linker; e) a second linker; or a hydrophilic polymer formed from binding of the first peptide and the second peptide, and these block molecules may be bound to each other to form a multi-block fusion peptide. The structure of these block molecules will be described below.

The hydrophilic molecules bound to the first peptide and the second peptide may be identical or different from each other. When the hydrophilic molecules are bound to both the first peptide and the second peptide, they may be expressed as first and second hydrophilic molecules. The hydrophilic molecule bound to the first peptide may be expressed as a first hydrophilic molecule, and the hydrophilic molecule bound to the second peptide may be expressed as second hydrophilic molecule.

A third linker may further exist for the binding of the second peptide and the second hydrophilic molecule. The third linker may be any one selected from a group consisting of G, GG, GGG, GS, GGS, GSG, GSS, GK, GGK, GKK, K and KK. The third linker is located between the second peptide and the second hydrophilic molecule.

The hydrophilic molecule is not specially limited as long as it is a molecule exhibiting hydrophilicity. The hydrophilic molecule may increase the binding sufficiency of nucleic acid material by being bound to the fusion peptide and maintaining the amphiphilic property of the peptide.

The hydrophilic molecule may be a hydrophilic polymer or a hydrophilic targeting ligand. The hydrophilic polymer may be any one selected from a group consisting of polyethylene glycol, Pluronic, pullulan, hyaluronic acid, glycol chitosan, heparin, chondroitin sulfate, fucoidan, dextran and a derivative thereof, more specifically polyethylene glycol.

The hydrophilic targeting ligand is not specially limited as long as it is any cell-directing moiety capable of binding to a fusion peptide and delivering the fusion peptide specifically to a target cell. For example, it may be one or more selected from a group consisting of a carbohydrate, an aptamer, a vitamin, folic acid, a hexosamine and a peptide which binds to a specific target on a cell membrane or cell surface, specifically, one or more carbohydrate which may be a monosaccharide, a disaccharide, a trisaccharide, a tetrasaccharide, an oligosaccharide or a polysaccharide. More specifically, it may be one or more selected from a group consisting of N-acetylgalactosamine (GalNAc), galactose, glucose, mannose, lactose, galactosamine, N-formylgalactosamine, N-propionylgalactosamine and N-butanoylgalactosamine.

The peptide-molecule conjugate with the hydrophilic molecule bound may effectively facilitate delivery into a target cell, provide high stability by forming a self-assembled monolayer when it forms a nanostructure by binding to a drug, a gold nanoparticle or a nucleic acid molecule, and inhibit nonspecific delivery to other organs or cells.

The hydrophilic molecule may be linked at the nucleotide level indirectly by cloning using an expression vector, or directly by a chemical or physical covalent bond or non-covalent bond between the fusion peptide of the present disclosure and the hydrophilic molecule.

The peptide-molecule conjugate has a molecular length of 5-6 nm and has a helicity of 0.8-0.9 in distilled water. Because it has a stable structure with the very high helicity, it can be stored for a long time even in distilled water at room temperature.

The peptide-molecule conjugate forms a self-assembled monolayer surrounding a nucleic acid material via a non-covalent bond with the nucleic acid material. It was verified through experiment that the self-assembled monolayer has a thickness of 5-7 nm, which corresponds to the molecular length of the peptide-molecule conjugate.

The peptide-molecule conjugate may have a chemical structure shown in the drawings, specifically any one selected from FIGS. 1-9, 33A, 34A, 34B, 35A, 35B, 36A, 37A, 38A, 38B, 38C, 39A, 40A, 40B, 41A, 41B, 41C, 43A, 43B, 43C, 43D and 45, which may be expressed as Formulas 1-31 in order. The chemical names of the chemical structures can be referred to in Table 1.

The present disclosure also provides a composition for nucleic acid delivery, which contains the peptide-molecule conjugate as an active ingredient.

The composition may further contain a nucleic acid. The nucleic acid may be a DNA or an RNA, specifically a naturally occurring or artificial DNA or RNA molecule, which may be single-stranded or double-stranded. The nucleic acid molecule may be one or more, and may be nucleic acid molecules of the same (e.g., having the same nucleotide sequence) or different types. Specifically, the nucleic acid may include one or more of a cDNA, a decoy DNA, a cfDNA, a ctDNA, an RNA, a siRNA, a miRNA, a shRNA, a stRNA, a snoRNA, a snRNA, a PNA, an antisense oligomer, a plasmid and other modified nucleic acids, although not being limited thereto.

Since the peptide-molecule conjugate in the composition of the present disclosure binds to the surface of a negatively charged nucleic acid, without special limitation in size, and forms a self-assembled monolayer, it can be used for a recombinant gene expression construct of any practical size.

The composition of the present disclosure may be used as a vaccine composition when the nucleic acid is a nucleic acid for vaccination or therapy.

The peptide-molecule conjugate of the present disclosure may be prepared into a nucleic acid carrier through binding with a nucleic acid. Owing to superior intracellular delivery rate and stable protection from the inactivation or denaturation of the nucleic acid by risk factors (urea, RNase, temperature, distilled water, etc.), it exhibits remarkable stability, storage and distribution characteristics and nucleic acid delivery effect as compared to the existing nucleic acid carriers.

In an example of the present disclosure, a nanostructure was prepared by mixing the peptide-molecule conjugate with an EGFP mRNA as a genetic material to be delivered and the activity of the gene under various environmental conditions and the location and expression level of the gene in Hela cells (cancer cells) were measured. As a result, improved gene delivery efficiency was verified.

In the present disclosure, the composition ratio of the peptide-molecule conjugate and the nucleic acid may be a charge ratio of 0.1:1-10:1, specifically a charge ratio of 0.2:1-5:1, more specifically a charge ratio of 0.25-1:1, for effective delivery of the nucleic acid. If the composition ratio is outside the above ranges, the effect of the nucleic acid may decrease due to the decreased activity of the nucleic acid.

The composition of the present disclosure may be affected by a material for facilitating or inhibiting endosomal escape during intracellular delivery of the nucleic acid. The material for inhibiting endosomal escape may be, for example, bafilomycin A, etc., and the material for facilitating endosomal escape may be, for example, amantadine, ammonium chloride, polyethylenimine, chloroquine, etc., although not being specially limited thereto. Whereas use the material for inhibiting endosomal escape such as bafilomycin A can inhibit gene delivery, the use of the material for facilitating endosomal escape can improve gene delivery.

That is to say, since the composition of the present disclosure not only stably protects nucleic acids by enabling long-term storage and distribution of the nucleic acids but also improves the intracellular delivery rate of the nucleic acids, it can be used not only for gene delivery not only for cultured cells but also for in-vivo gene delivery, i.e., to cells, tissues or organs of living animals.

In the composition, the peptide-molecule conjugate and the nucleic acid exist, through self-assembly, as a nanostructure consisting of: a core containing the nucleic acid; and a self-assembled monolayer surrounding the core. The nanostructure may be in the form of a nanotube, and the self-assembled monolayer may have an average thickness of 5-7 nm.

Hereinafter, the present disclosure will be described in more detail through examples. The examples are provided only to describe the present disclosure more specifically and it will be obvious to those having ordinary knowledge in the art that the scope of the present disclosure is not limited by the examples.

Experimental Methods

Experimental Materials and Devices

Fmoc-amino acids, Fmoc-NH-PEG8-propionic acids, Fmoc-epsilon-Ahx-OH and Fmoc-12-Ado-OH were purchased from AAPPTec (Louisville, KY). The coupling reagents 2-(6-chloro-1H-benzotriazole-1-yl)-1,1,3,3-tetramethylaminium hexafluorophosphate (HCTU) and 1-hydroxybenzotriazole hydrate (HOBt) were purchased from AnaSpec (Fremont, USA). N,N-diisopropylethylamine (DIPEA), sodium citrate tribasic dihydrate and hydrogen tetrachloroaurate (III) ($HAuCl_4 \cdot H_2O$) were purchased from Sigma-Aldrich (St. Louis, USA). M13mp18 ssDNA was purchased from New England BioLabs (Ipswich, USA) (Catalog No.: N4040S). 1-Thio-beta-D-glucose tetraacetate was acquired from Alfa Aesar (Ward Hill, USA). CleanCap® enhanced green fluorescent protein (EGFP) mRNA (5-methoxyuridine) was purchased from TriLink BioTechnologies (San Diego, USA). EGFP mRNA labeled using Cy5-labeled antisense oligonucleotide (/5Cy5/GCG AGC TGC ACG CTG CCG TC) (SEQ ID NO: 18) was prepared by Integrated DNA Technologies (Coralville, USA). Dulbecco's modified Eagle's medium (DMEM), Opti-MEM reduced-serum medium, trypsin-EDTA and Dulbecco's phosphate-buffered saline (DPBS) were purchased from GIBCO (Grand Island, USA). Fetal bovine serum (FBS), an antibiotic mixture (penicillin-streptomycin), LysoTracker™ Red DND-99 and LysoTracker™ Green DND-26 were purchased from Invitrogen (Waltham, USA).

CD (Circular Dichroism) Spectroscopy

CD spectra were measured using a Chirascan circular dichroism spectrometer equipped with a Peltier temperature controller (Applied Photophysics, Surrey, UK). The concentration of a sample for measurement such as a peptide-molecule conjugate (SAB) was adjusted to 20-26 μM. A nucleic acid material such as EGFP mRNA was prepared at a concentration of 104 nM. The peptide-molecule conjugate (SAB) was sonicated and kept at room temperature for 1 hour before measurement in order to prevent aggregation. All measurements were made at 20° C. using a cuvette having a path length of 2 mm. The peptide-molecule conjugate (SAB) was measured in a wavelength range of 190-260 nm and the sample containing a nucleic acid material such as mRNA was measured in a wavelength range of 190-320 nm. Measurement was repeated 3 times and the average value was taken.

EMSA Assay (Electrophoretic Mobility Shift Assay with mRNA)

When a nanostructure was formed through self-assembly by reacting a peptide-molecule conjugate (SAB) with a nucleic acid material (dsDNA or mRNA), agarose gel EMSA was conducted to measure their interactions, binding ratio, stability, etc.

First, the nucleic acid material of a fixed concentration (100 fmol mRNA) was reacted with the peptide-molecule conjugate (SAB) of various concentrations. Immediately before mixing with the nucleic acid material, the peptide-molecule conjugate (SAB) was sonicated for 5 minutes to prevent self-aggregation. The sonicated peptide-molecule conjugate (SAB, 5 μL) was added to the nucleic acid material (5 mL) and a nanostructure was prepared by adding distilled water. The sample was prepared by snap cooling. Specifically, after heating at 70° C. for 10 minutes and snap-cooling on ice, the prepared sample was stored at room temperature. The stored sample was mixed with 2 μL of 60% glycerol. Electrophoresis was performed at 100 V for 60 minutes on 0.8% agarose gel using 1×TBE. The band was observed after staining with SYBR™ Gold nucleic acid gel stain (Invitrogen, Waltham, USA).

AFM (Atomic Force Microscopy)

A solution (20 μM, 20 μL) containing the sample such as the fusion peptide or the peptide-molecule conjugate (SAB) was dropped on the surface of cleanly cut mica and then dried completely at room temperature. AFM images were obtained using a NX10 system (Park Systems, Suwon, Korea) equipped with a PPP-NCHR AFM probe (Nanosensors, Switzerland) in the non-contact mode. The result was analyzed using the XEI program (Park Systems, Suwon, Korea).

TEM (Transmission Electron Microscopy)

The sample was prepared on a carbon-coated copper grid (carbon type-B grid, 200-mesh copper grid with a 97 μm hole; Ted Pella, Redding, USA). The solutions of AuNPs and the peptide-molecule conjugate (SAB) were prepared as 0.9 nM and 6.67 μM, respectively. After dropping the sample solution on the grid and drying completely, the sample was stained by treating with 2 μL of a 2% (w/v) uranyl acetate solution for 1 minute. After preparing mRNA and peptide-molecule conjugate (SAB) solutions at concentrations of 5-10 nM and 0.62-9.96 μM, respectively, the sample solution was dropped on a grid and then absorbed with a filter paper 1 minute later. Then, the sample was stained immediately with 2 μL of 0.2-2% uranyl acetate for 10-30 seconds. The remaining solution was removed with a filter paper and the sample was analyzed with a JEM-F200 multipurpose electron microscope (JEOL, Akishima, Japan) under the condition of 120 kV or 200 kV. The result was analyzed using the DigitalMicrograph™ software (Gatan, Pleasanton, USA).

Flow Cytometry

The level of cellular penetration and the efficiency of cellular infection were analyzed by flow cytometry using a BD LSR II flow cytometer (Becton Dickinson and Company, Franklin Lakes, USA). After separating cells by treating with 100 μL of trypsin-EDTA (0.05%) on a 96-well plate and diluting with DMEM of the same volume, the resulting solution was transferred to a microtube and then centrifuged. The cells were resuspended in 300 μL of DPBS and then transferred to a Falcon™ round-bottom polystyrene tube (Corning, Corning, NY). For detection of Cy5, the cells were exposed to a 640-nm laser and then detected with a 660/20-nm bandpass filter. For detection of EGFP, the cells were exposed to a 488-nm laser and then detected with a 525/50-nm bandpass filter. The result was analyzed using the FlowJo software (BD, Franklin Lakes, USA).

Confocal Microscopy

After treating the sample with 50 nM LysoTracker™ Red DND-99 or LysoTracker™ Green DND-26, lysosomes were stained by incubating at 37° C. for 15-30 minutes in DMEM. For microscopic observation, the cells were washed 4 times with 100 μL of DPBS and then the medium was replaced with Opti-MEM. The fluorescence of the cells was observed using a LSM 880 confocal microscope (Carl Zeiss, Oberkochen, Germany). The microscopic images were analyzed using the ZEN software (Carl Zeiss, Oberkochen, Germany).

Statistical Analysis

All experimental results were represented as mean±standard error, and the statistical significance of the experimental results was tested by Student's t-test. P-value≤0.05 was considered significant.

Examples 1-31. Preparation of Peptide-Molecule Conjugates (SAB1 to SAB3, SAB-$g_1$ to SAB-$g_6$)

Peptide-molecule conjugates having the structures shown in FIGS. 1-9, 33A, 34A, 34B, 35A, 35B, 36A, 37A, 38A, 38B, 38C, 39A, 40A, 40B, 41A, 41B, 41C, 43A, 43B, 43C, 43D and 45 (SAB1 to SAB3, SAB-$g_1$ to SAB-$g_6$, etc.) were synthesized by a Fmoc solid-phase peptide synthesis (SPPS) protocol on Rink Amide MBHA resin LL (100-200 mesh, 0.30-0.40 mmol $g^{-1}$, Novabiochem, Germany). They were synthesized according to the manual or using a Tribute peptide synthesizer (Protein Technologies Ltd; Manchester, UK). When the synthesis was completed, the resin-bound peptide was treated with a cleavage cocktail (trifluoroacetic acid (TFA):1,2-ethanedithiol:tioanisole at a ratio of 95:2.5:2.5 or trifluoroacetic acid (TFA):water:triisopropylsilane (TIS) at a ratio of 95:2.5:2.5) for 3 hours for cleavage from the resin and final deprotection. The peptide was precipitated using TBME (tert-butyl methyl ether) and then purified by reversed-phase high-performance liquid chromatography (HPLC) using acetonitrile and water containing 0.1% TFA as mobile phases. The molecular weight of the peptide was identified by MALDI-TOF (matrix-assisted laser desorption/ionization time-of-flight) mass spectrometry (autoflex max; Bruker, Germany). The purity of the peptide measured by analytical HPLC was >95%. The concentration of the peptide was determined spectrophotometrically in water/acetonitrile (1:1) using the molar extinction coefficient of amide bond at 230 nm (200 $M^{-1}$ $cm^{-1}$).

The chemical structures of the prepared peptide-molecule conjugates are shown in FIGS. 1-9, 33A, 34A, 34B, 35A, 35B, 36A, 37A, 38A, 38B, 38C, 39A, 40A, 40B, 41A, 41B, 41C, 43A, 43B, 43C, 43D and 45, and were named as SAB1, SAB2, SAB3, SAB-$g_1$, SAB-$g_2$, SAB-$g_3$, SAB-$g_4$, SAB-$g_5$, SAB-$g_6$, etc. in order. They are summarized in Table 1.

TABLE 1

| Ex. No. | Peptide-molecule conjugates | Relevant figures and names |
|---|---|---|
| 1 | Ac-(PEG8)-AELAALEAELAALE-GGG-K-GGG-KLAALKAKLAALKAG-(PEG8)-$NH_2$ | 1, 10, 11 |
| 1 | Ac-(PEG8)-AELAALEAELAALE-GGG-K-GGG-KLAALKAKLAALKAG-(PEG8)-$NH_2$ | SAB1 |

TABLE 1-continued

| Ex. No. | Peptide-molecule conjugates | Relevant figures and names |
|---|---|---|
| 2 | Ac-(PEG8)-AELAALEAELAALE-$(Ahx)_2$-K-$(Ahx)_2$-KLAALKAKLAALKAG-(PEG8)-$NH_2$ | 2, 10, 11, 15 |
| 2 | Ac-(PEG8)-AELAALEAELAALE-$(Ahx)_2$-K-$(Ahx)_2$-KLAALKAKLAALKAG-(PEG8)-$NH_2$ | SAB2 |
| 3 | Ac-(PEG8)-AELAALEAELAALE-Ado-K-Ado-KLAALKAKLAALKAG-(PEG8)-$NH_2$ | 3, 10, 11, 13 |
| 3 | Ac-(PEG8)-AELAALEAELAALE-Ado-K-Ado-KLAALKAKLAALKAG-(PEG8)-$NH_2$ | SAB3 |
| 4 | Glucose-(PEG8)-AELAALEAELAALE-$(Ahx)_2$-K-$(Ahx)_2$-KLAALKAKLAALKAG-(PEG8)-$NH_2$ | 4, 10, 11, 16, 17 |
| 4 | Glucose-(PEG8)-AELAALEAELAALE-$(Ahx)_2$-K-$(Ahx)_2$-KLAALKAKLAALKAG-(PEG8)-$NH_2$ | SAB-$g_1$ |
| 5 | Glucose-(PEG8)-AELAALEAELAALE-$(Ahx)_2$-K-$(Ahx)_2$-KLAALKAKLAALKAG-(PEG8)-K($^N$glucose)-$NH_2$ | 5, 10, 11, 16, 17 |
| 5 | Glucose-(PEG8)-AELAALEAELAALE-$(Ahx)_2$-K-$(Ahx)_2$-KLAALKAKLAALKAG-(PEG8)-K($^N$glucose)-$NH_2$ | SAB-$g_2$ |
| 6 | Glucose-GS-AELAALEAELAALE-$(Ahx)_2$-K-$(Ahx)_2$-KLAALKAKLAALKAG-K($^N$glucose)-$NH_2$ | 6, 10, 11, 16-32 |
| 6 | Glucose-GS-AELAALEAELAALE-$(Ahx)_2$-K-$(Ahx)_2$-KLAALKAKLAALKAG-K($^N$glucose)-$NH_2$ | SAB-$g_3$ |
| 7 | Glucose-GS-AELAALEUELAALE-$(Ahx)_2$-K-$(Ahx)_2$-KLAALKUKLAALKAG-K($^N$glucose)-$NH_2$ | 7, 10, 11, 16, 17 |
| 7 | Glucose-GS-AELAALEUELAALE-$(Ahx)_2$-K-$(Ahx)_2$-KLAALKUKLAALKAG-K($^N$glucose)-$NH_2$ | SAB-$g_4$ |
| 8 | Glucose-GS-AELUALEAELAULE-$(Ahx)_2$-K-$(Ahx)_2$-KLUALKAKLAULKAG-K($^N$glucose)-$NH_2$ | 8, 10, 11, 16 |
| 8 | Glucose-GS-AELUALEAELAULE-$(Ahx)_2$-K-$(Ahx)_2$-KLUALKAKLAULKAG-K($^N$glucose)-$NH_2$ | SAB-$g_5$ |
| 9 | Glucose-GS-AELUALEUELAULE-$(Ahx)_2$-K-$(Ahx)_2$-KLUALKUKLAULKAG-K($^N$glucose)-$NH_2$ | 9, 10, 11, 17 |
| 9 | Glucose-GS-AELUALEUELAULE-$(Ahx)_2$-K-$(Ahx)_2$-KLUALKUKLAULKAG-K($^N$glucose)-$NH_2$ | SAB-$g_6$ |
| 10 | Ac-(PEG8)-AELAALEAELAALE-$(Ahx)_2$-E (adenine)-$(Ahx)_2$-KLAALKAKLAALKAG-(PEG8) | 33A, 33B |
| 10 | Ac-(PEG8)-AELAALEAELAALE-$(Ahx)_2$-E (adenine)-$(Ahx)_2$-KLAALKAKLAALKAG-(PEG8) | |
| 11 | Ac-(PEG8)-AELAALEAELAALE$(Ahx)_2$-E (adenine)E (adenine)-$(Ahx)_2$-KLAALKAKLAALKAG-(PEG8) | 34A, 34C, 35 |
| 11 | Ac-(PEG8)-AELAALEAELAALE$(Ahx)_2$-E (adenine)E (adenine)-$(Ahx)_2$-KLAALKAKLAALKAG-(PEG8) | $(PEG8)_2$-AA-U0 |
| 12 | Ac-(PEG8)-AELAALEAELAALE$(Ahx)_2$-E (adenine)GE (adenine)-$(Ahx)_2$-KLAALKAKLAALKAG-(PEG8) | 34B, 34C |
| 12 | Ac-(PEG8)-AELAALEAELAALE$(Ahx)_2$-E (adenine)GE (adenine)-$(Ahx)_2$-KLAALKAKLAALKAG-(PEG8) | $(PEG8)_2$-AGlyA-U0 |
| 13 | Glucose-GS-AELAALEAELAALE-$(Ahx)_2$-E (adenine)-E (adenine)-$(Ahx)_2$-KLAALKAKLAALKAG-GS | 35A, 35B, 35C |
| 13 | Glucose-GS-AELAALEAELAALE-$(Ahx)_2$-E (adenine)-E (adenine)-$(Ahx)_2$-KLAALKAKLAALKAG-GS | $(PEG8)_2$-AA-U0 |
| 14 | Glucose-GS-AELAALEAELAALE-$(Ahx)_2$-E (thymine)-E (thymine)-$(Ahx)_2$-KLAALKAKLAALKAG-GS | 36A, 36B |

TABLE 1-continued

| Ex. No. | Peptide-molecule conjugates | Relevant figures and names |
|---|---|---|
| 14 | Glucose-GS-AELAALEAELAALE-$(Ahx)_2$-E (thymine)-E (thymine)-$(Ahx)_2$-KLAALKAKLAALKAG-GS | $Glc_1$-TT-U0 |
| 15 | Glucose-GS-AELAALEAELAALE-$(Ahx)_2$-E (adenine)E (adenine)-$(Ahx)_2$-KLAALKAKLAALKAG-K (glucose) | 37A, 37B |
| 15 | Glucose-GS-AELAALEAELAALE-$(Ahx)_2$-E (adenine)E (adenine)-$(Ahx)_2$-KLAALKAKLAALKAG-K (glucose) | $Glc_2$-AA-U0 |
| 16 | Glucose-GS-AELAALEUELAALE-$(Ahx)_2$-E (adenine)E (adenine)-$(Ahx)_2$-KLAALKUKLAALKAG-K (glucose) | 38A, 38D |
| 16 | Glucose-GS-AELAALEUELAALE-$(Ahx)_2$-E (adenine)E (adenine)-$(Ahx)_2$-KLAALKUKLAALKAG-K (glucose) | $Glc_2$-AA-U2 |
| 17 | Glucose-GS-AELUALEAELAULE-$(Ahx)_2$-E (adenine)E (adenine)-$(Ahx)_2$-KLUALKAKLAULKAG-K (glucose) | 38B, 38D |
| 17 | Glucose-GS-AELUALEAELAULE-$(Ahx)_2$-E (adenine)E (adenine)-$(Ahx)_2$-KLUALKAKLAULKAG-K (glucose) | $Glc_2$-AA-U4 |
| 18 | Glucose-GS-AELUALEUELAULE-$(Ahx)_2$-E (adenine)E (adenine)-$(Ahx)_2$-KLUALKUKLAULKAG-K (glucose) | 38C, 38D, 43 44 |
| 18 | Glucose-GS-AELUALEUELAULE-$(Ahx)_2$-E (adenine)E (adenine)-$(Ahx)_2$-KLUALKUKLAULKAG-K(glucose) | $Glc_2$-AA-U6 |
| 19 | Glucose-GS-UELUALEUELAULE-$(Ahx)_2$-E (adenine)E (adenine)-$(Ahx)_2$-KLUALKUKLAULKUG-K (glucose) | 39A, 39B, 42, 43A |
| 19 | Glucose-GS-UELUALEUELAULE-$(Ahx)_2$-E (adenine)E (adenine)-$(Ahx)_2$-KLUALKUKLAULKUG-K (glucose) | $Glc_2$-AA-U8 |
| 20 | Ac-R-GS-UELUALEUELAULE-$(Ahx)_2$-E (adenine)E (adenine)-$(Ahx)_2$-KLUALKUKLAULKUG-K (glucose) | 40A, 40C |
| 20 | Ac-R-GS-UELUALEUELAULE-$(Ahx)_2$-E (adenine)E (adenine)-$(Ahx)_2$-KLUALKUKLAULKUG-K (glucose) | R-AA-Glc-U8 |
| 21 | Ac-R-GS-UELUALEUELAULE-$(Ahx)_2$-E (thymine)E (thymine)-$(Ahx)_2$-KLUALKUKLAULKUG-K (glucose) | 40B, 40C |
| 21 | Ac-R-GS-UELUALEUELAULE-$(Ahx)_2$-E (thymine)E (thymine)-$(Ahx)_2$-KLUALKUKLAULKUG-K (glucose) | R-TT-Glc-U8 |
| 22 | Ac-R-GS-UELUALEUELAULE-$(Ahx)_2$-E (thymine)E (thymine)-$(Ahx)_2$-KLUALKUKLAULKUG-K(PEG8) | 41A, 41D |
| 22 | Ac-R-GS-UELUALEUELAULE-$(Ahx)_2$-E (thymine)E (thymine)-$(Ahx)_2$-KLUALKUKLAULKUG-K(PEG8) | R-TT-PEG8-U8 |
| 23 | Ac-R-GS-UELUALEUELAULE-$(Ahx)_2$-E (thymine)E (thymine)-$(Ahx)_2$-KLUALKUKLAULKUG-K$(PEG8)_2$ | 41B, 41D |
| 23 | Ac-R-GS-UELUALEUELAULE-$(Ahx)_2$-E (thymine)E (thymine)-$(Ahx)_2$-KLUALKUKLAULKUG-K$(PEG8)_2$ | R-TT-$(PEG8)_2$-U8 |
| 24 | Ac-S-GS-UELUALEUELAULE-$(Ahx)_2$-E (thymine)E (thymine)-$(Ahx)_2$-KLUALKUKLAULKUG-K(PEG8) | 41C, D |
| 24 | Ac-S-GS-UELUALEUELAULE-$(Ahx)_2$-E (thymine)E (thymine)-$(Ahx)_2$-KLUALKUKLAULKUG-K(PEG8) | S-TT-PEG8-U8 |
| 25 | Glucose-GS-UELUALEUELAULE-$(Ahx)_2$-E (cytosine)E (cytosine)-$(Ahx)_2$-KLUALKUKLAULKUG-K (glucose) | 43B, 43E, 44 |
| 25 | Glucose-GS-UELUALEUELAULE-$(Ahx)_2$-E (cytosine)E (cytosine)-$(Ahx)_2$-KLUALKUKLAULKUG-K (glucose) | CC |
| 26 | Glucose-GS-UELUALEUELAULE-$(Ahx)_2$-E (guanine)E (guanine)-$(Ahx)_2$-KLUALKUKLAULKUG-K (glucose) | 43C, 43E, 44 |
| 26 | Glucose-GS-UELUALEUELAULE-$(Ahx)_2$-E (guanine)E (guanine)-$(Ahx)_2$-KLUALKUKLAULKUG-K (glucose) | GG |
| 27 | Glucose-GS-UELUALEUELAULE-$(Ahx)_2$-E (thymine)E (thymine)-$(Ahx)_2$-KLUALKUKLAULKUG-K (glucose) | 43D, 43E, 44 |

TABLE 1-continued

| Ex. No. | Peptide-molecule conjugates | Relevant figures and names |
|---|---|---|
| 27 | Glucose-GS-UELUALEUELAULE-$(Ahx)_2$-E (thymine)E (thymine)-$(Ahx)_2$-KLUALKUKLAULKUG-K (glucose) | TT |
| 28 | Glycolic acid-SGSG-C-GG-AUAUAUAUAUA-GG-R-GG-AUAUAUAUAUA-GG-C (linear) | 45, 46, 48, 49 |
| 28 | Glycolic acid-SGSG-C-GG-AUAUAUAUAUA-GG-R-GG-AUAUAUAUAUA-GG-C (linear) | lin-R(AU)A5-GA |
| 29 | Glycolic acid-SGSG-C-GG-AUAUAUAUAUA-GG-R-GG-AUAUAUAUAUA-GG-C (cyclic; disulfide) | 45, 47, 48, 49 |
| 29 | Glycolic acid-SGSG-C-GG-AUAUAUAUAUA-GG-R-GG-AUAUAUAUAUA-GG-C (cyclic; disulfide) | lin-R(AU)A5-Glc |
| 30 | Glucose-SGSG-C-GG-AUAUAUAUAUA-GG-R-GG-AUAUAUAUAUA-GG-C (linear) | 45,50 |
| 30 | Glucose-SGSG-C-GG-AUAUAUAUAUA-GG-R-GG-AUAUAUAUAUA-GG-C (linear) | cyc-R(AU)A5-GA |
| 31 | Glucose-SGSG-C-GG-AUAUAUAUAUA-GG-R-GG-AUAUAUAUAUA-GG-C (cyclic; disulfide) | 45,50 |
| 31 | Glucose-SGSG-C-GG-AUAUAUAUAUA-GG-R-GG-AUAUAUAUAUA-GG-C (cyclic; disulfide) | cyc-R(AU)A5-Glc |

Test Example 1. Chemical Structure and Analysis of Peptide-Molecule Conjugates (SABs)

Figure 10:
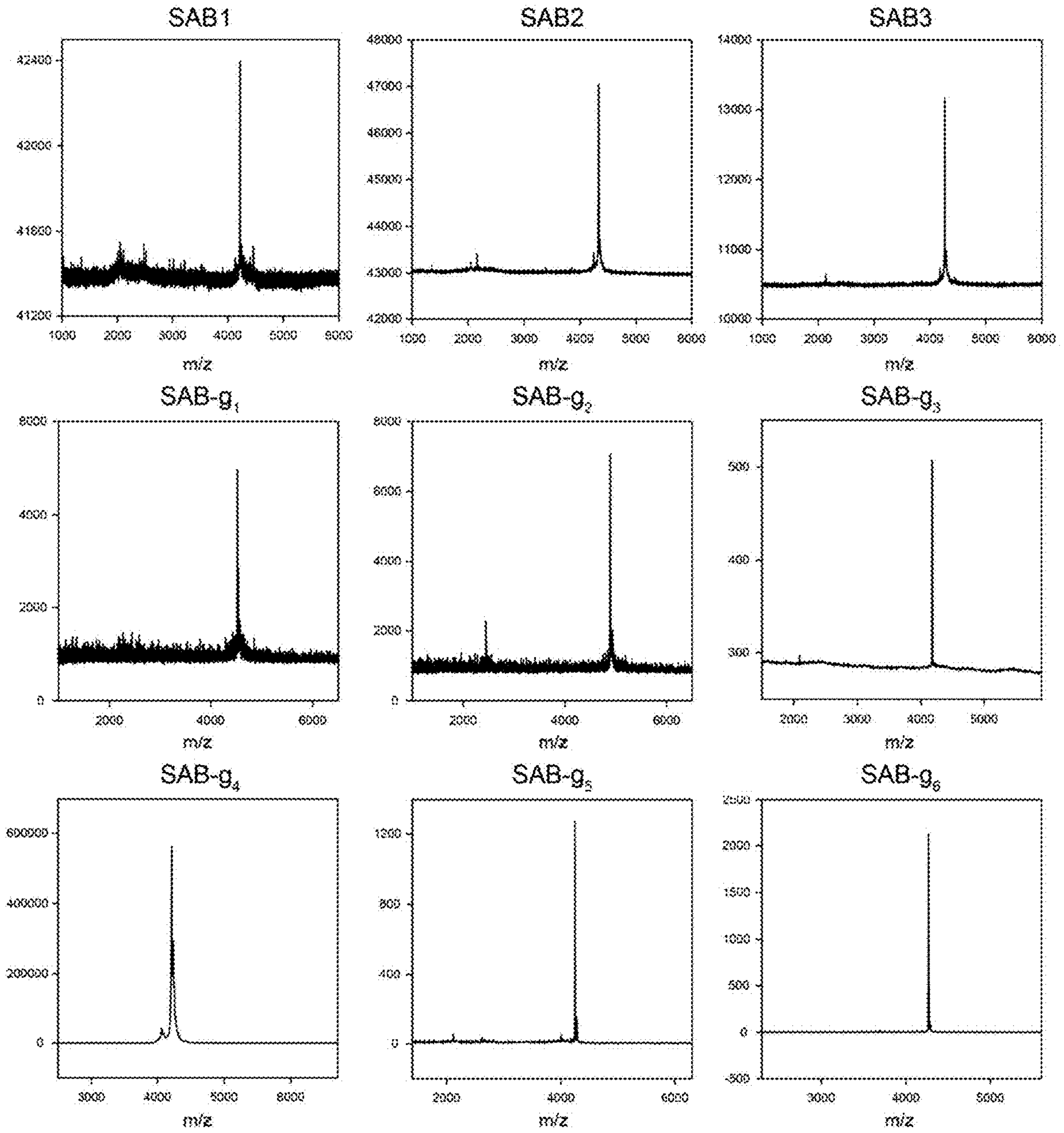
FIG. 10 shows a MALDI-TOF MS analysis result for peptide-molecule conjugates prepared in Examples 1-9 (SAB1 to SAB3, SAB-$g_1$ to SAB-$g_6$).
Figure 11:
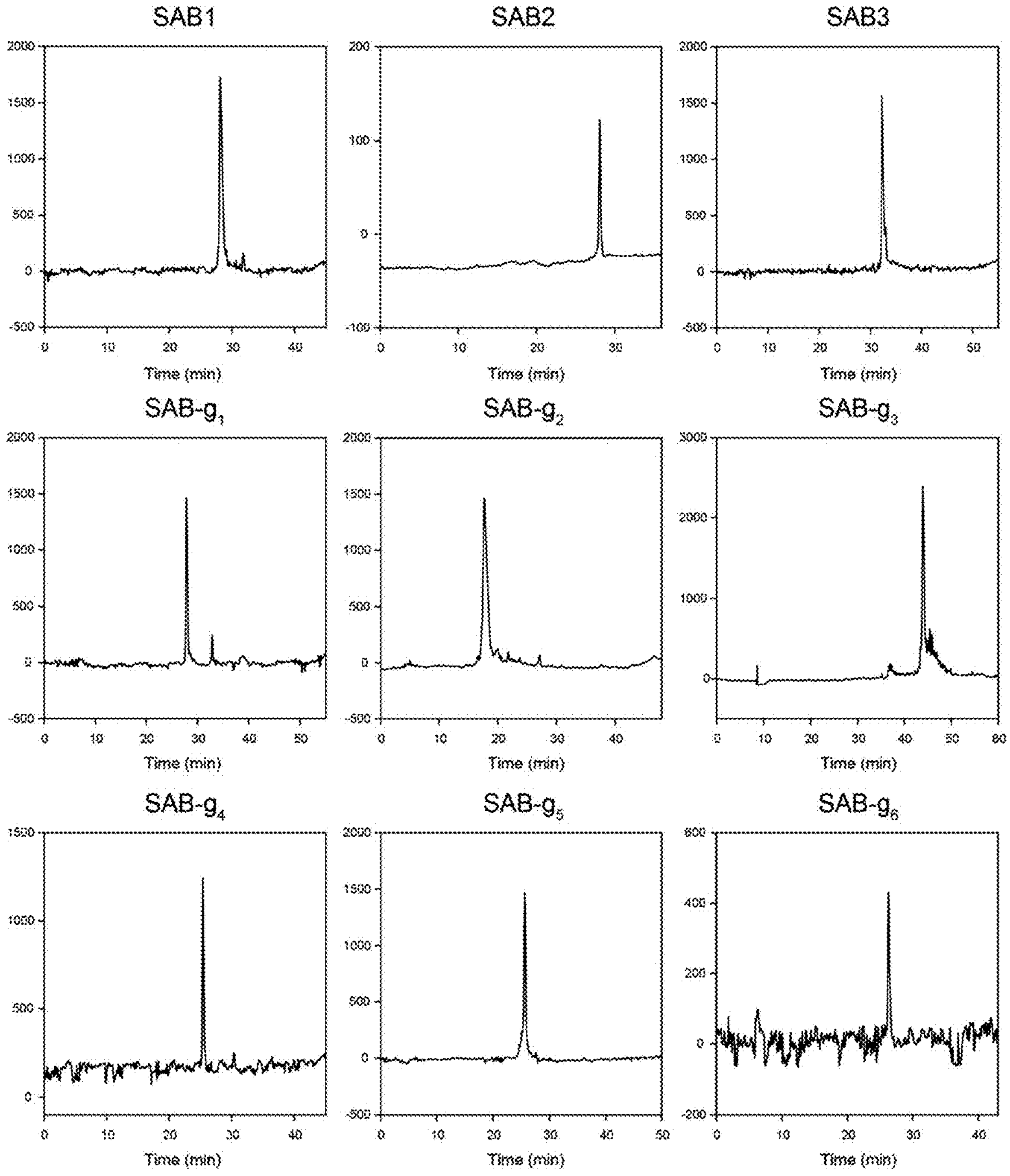
FIG. 11 shows an HPLC analysis result for peptide-molecule conjugates prepared in Examples 1-9 (SAB1 to SAB3, SAB-$g_1$ to SAB-$g_6$).

The peptide-molecule conjugates prepared in Examples 1-9 (SAB1 to SAB3, SAB-$g_1$ to SAB-$g_6$) were purified by HPLC and then analyzed by MALDI-TOF MS. The result is shown in FIG. 10 and FIG. 11 and their chemical structures are shown in FIGS. 1-9.

FIGS. 1-9 show the chemical structures of the peptide-molecule conjugates (SAB). In the figures, 'Ahx' indicates aminohexanoic acid, 'Ado' indicates aminododecanoic acid, PEG8 indicates polyethylene glycol 8, and U indicates Aib (2-aminoisobutyric acid). The structures are as follows.

[Structural Formula 1]

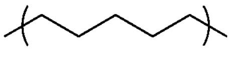

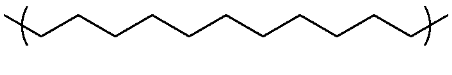

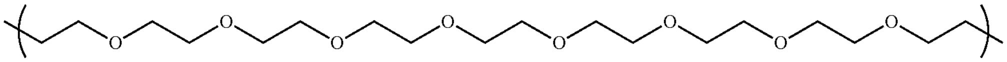

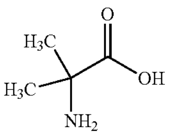

FIG. 10 shows the MALDI-TOF MS spectra of the peptide-molecule conjugates prepared in Examples 1-9 (SAB1 to SAB3, SAB-$g_1$ to SAB-$g_6$), and FIG. 11 shows the HPLC analysis result for the peptide-molecule conjugates prepared in Examples 1-9 (SAB1 to SAB3, SAB-$g_1$ to SAB-$g_6$). It can be seen that the peptide-molecule conjugate (SAB1 to SAB3, SAB-$g_1$ to SAB-$g_6$) having various sequences and structures were synthesized and purified successfully according to the method of Examples 1-9.

Test Example 2. Theoretical Structures and Principles of Self-Adjusting Building Blocks The peptide-molecule conjugates of Examples 1-3 (SAB1 to SAB3) were designed. The peptide-molecule conjugates are also called 'SABs', which means self-adjusting building blocks. The peptide-molecule conjugates were designed so that self-assembled monolayers can be formed also for nucleic acid materials (mRNA, etc.) having irregular and flexible structures. Because the peptide-molecule conjugates were designed centered on the balance of dynamic plasticity (structural adaptation to surrounding environment) and stiffness (resistance to deformation), the volume fraction and structure can be adjusted dynamically depending on the structure of the targeted materials.

Figure 12A:
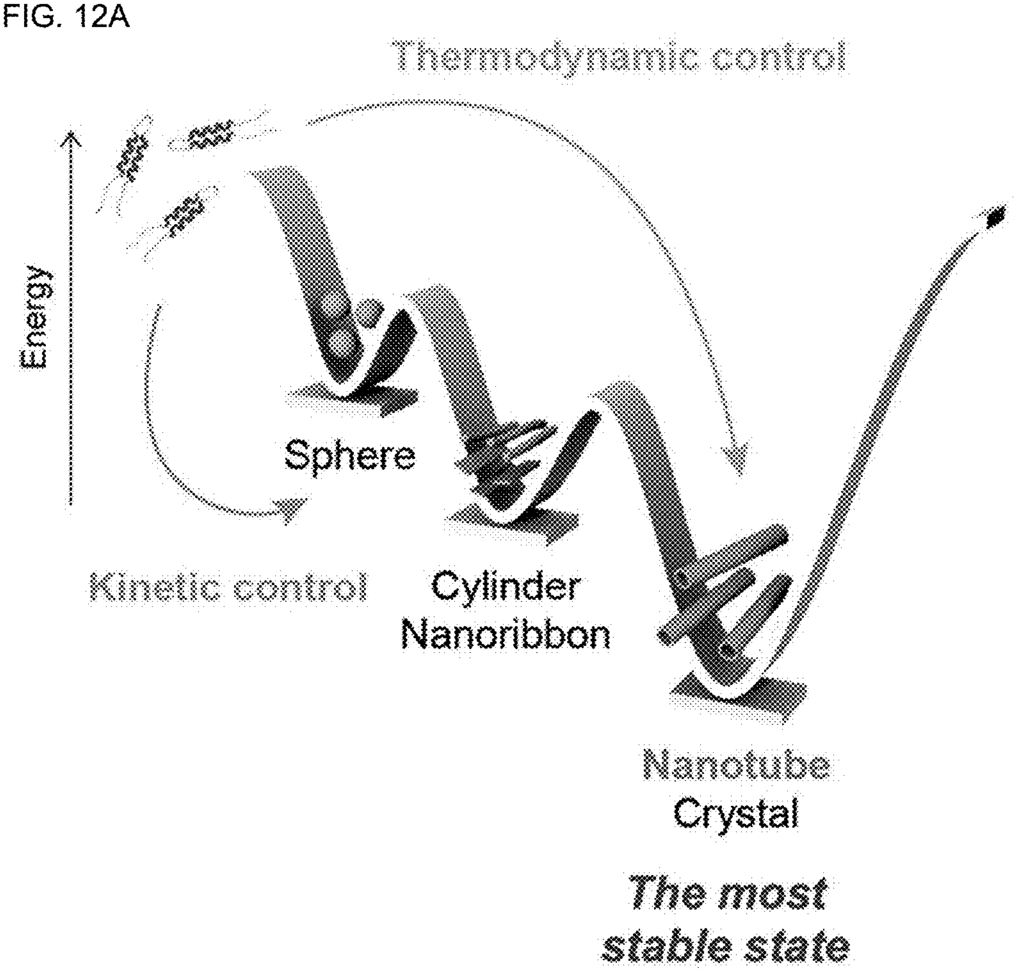
FIGS. 12A to 12E show the structure of peptide-molecule conjugates designed according to the present disclosure and coating of various target molecules through self-assembly.
Figure 12B:
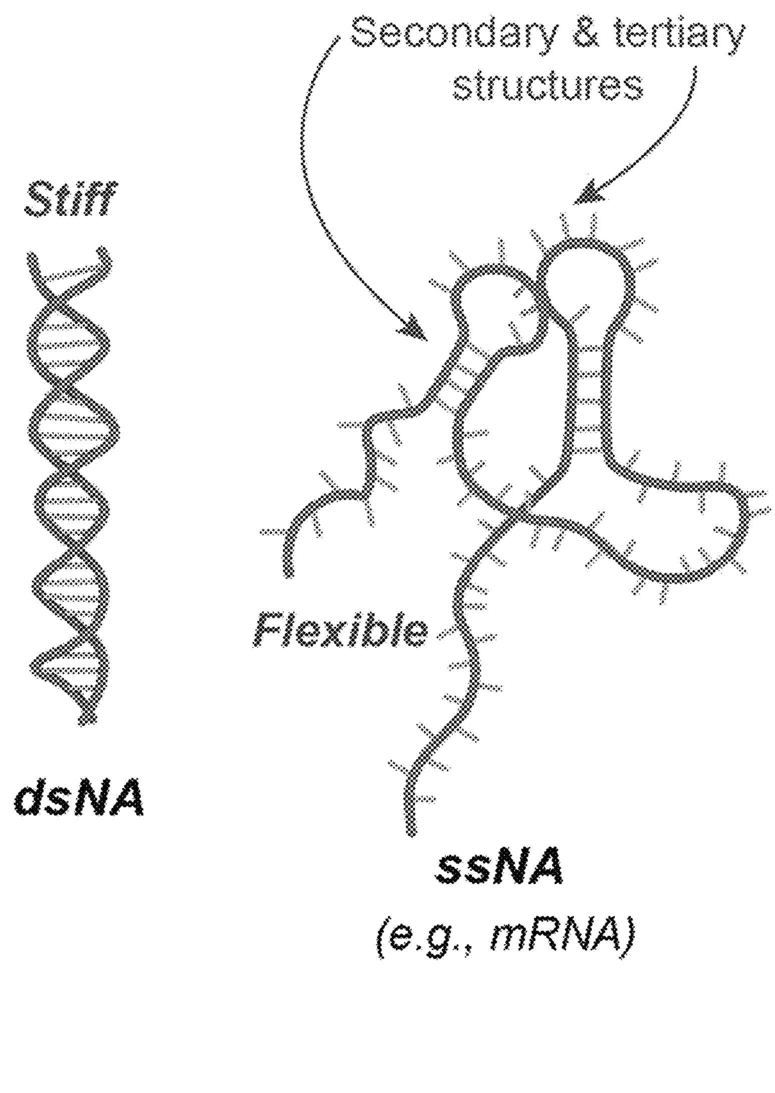
Figure 12C:
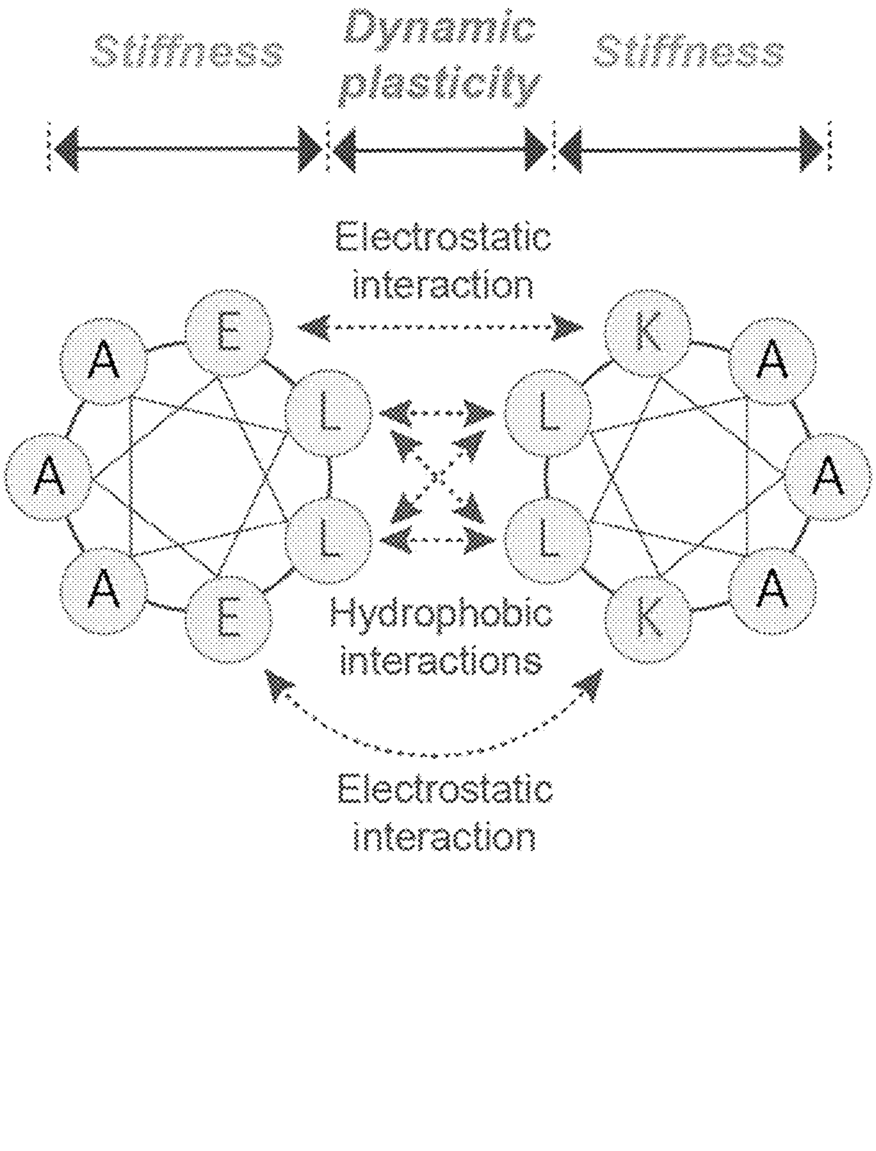
Figure 12D:
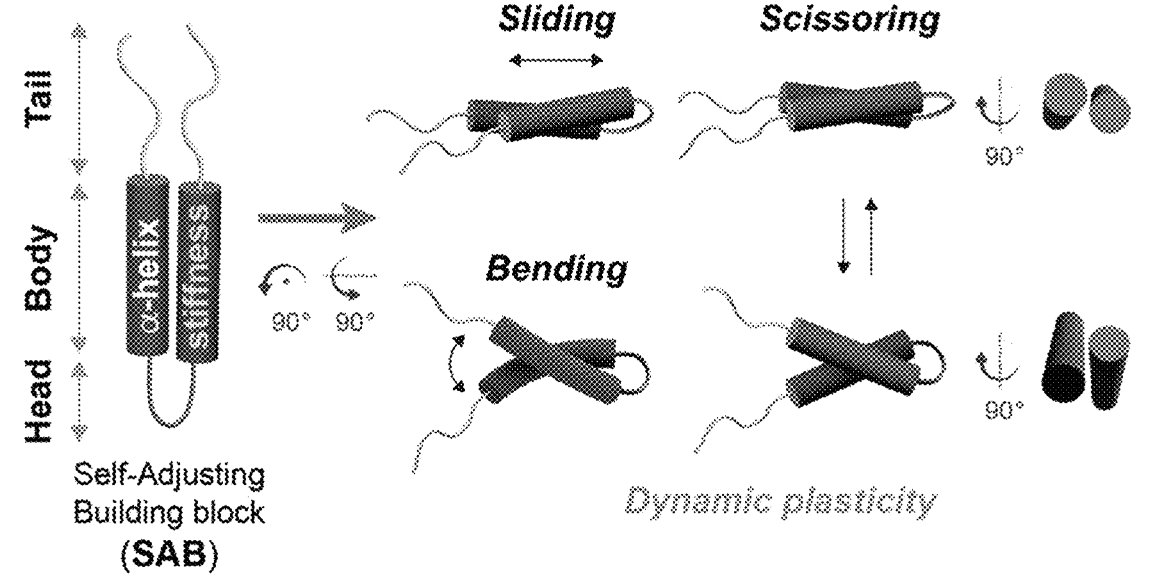
Figure 12E:
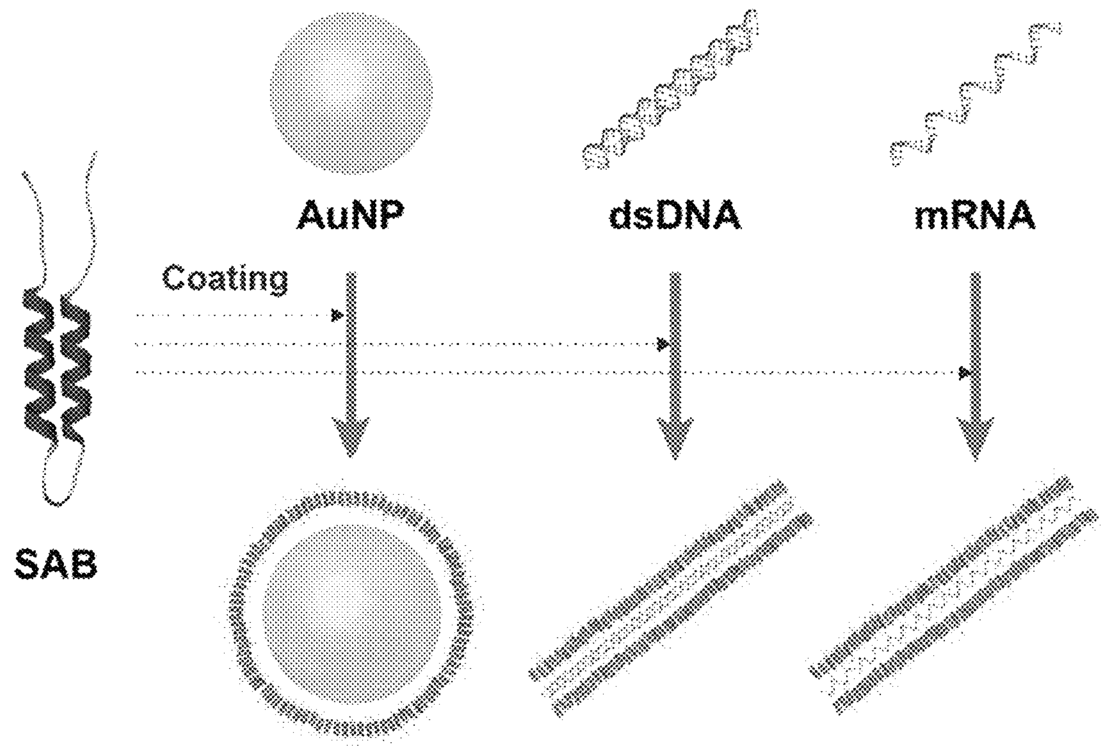

FIGS. 12A to 12E shows the structure of the peptide-molecule conjugates designed according to the present disclosure and coating of various target molecules through self-assembly. FIG. 12A shows a result of analyzing the thermodynamic stability of nanostructures depending on type. FIG. 12B shows the difference in stiffness and irregularity of a double-stranded nucleic acid (dsNA) and a single-stranded nucleic acid (ssNA), and FIG. 12C shows a result of analyzing a dimeric α-helical block (body domain) of the peptide-molecule conjugate, consisting of an α-helical coiled coil formed from the first and second peptides, using a helical wheel diagram. FIG. 12D schematically shows the principle of the dynamic plasticity of a peptide-molecule conjugate (SAB), and FIG. 12E shows the structure of a peptide-molecule conjugate (SAB) formed from coating of a nucleic acid (dsDNA or mRNA) on the surface of a nanoparticle (AuNP) through self-assembly.

The structure and characteristics of the peptide-molecule conjugate designed according to the present disclosure (SAB) will be described in detail referring to FIGS. 12A to 12E. Many proteins exhibit dynamic characteristics such as allostericity, induced fitting, protein-protein sliding. It is known that they are derived from the stability of the proteins. In the present disclosure, the peptide-molecule conjugates (SABs) were designed by inspiration from the dynamic characteristics of proteins. Specifically, the peptide-molecule conjugate (SAB) was designed to have a hydrophobic α-helical coiled coil domain (body) consisting of first and second peptides, a positively charged domain (head) consisting of a linker, and a hydrophilic domain (tail) formed as a hydrophilic polymer is bound to one terminal of the first and second peptides (FIG. 12D). The body domain plays an important role in the self-adjusting function of the peptide-molecule conjugate. Because two α-helices can be fixed in various directions by multiple non-covalent interactions formed by theα-helical coiled coil structure, the peptide-molecule conjugate can have dynamic plasticity (FIGS. 12C, 12D).

As shown in FIGS. 12C and 12D, the peptide-molecule conjugate (SAB) has a hairpin structure wherein two peptides (first and second peptides) forming the body domain face each other, which provides dynamic plasticity through non-covalent interaction such as sliding, bending or scissoring. In addition, the two peptides also have stiffness together with the dynamic plasticity.

Due to the structural characteristics described above, the peptide-molecule conjugate according to the present disclosure (SAB) can rearrange and self-adjust the structure and volume fraction corresponding to the target. Therefore, it can form a self-assembled monolayer with thermal stability while maintaining the structure and shape of the target.

Test Example 3. Formation of Nanostructure for Gold Nanoparticles Using Peptide-Molecule Conjugate (SAB)

3-1. Synthesis of Gold Nanoparticles (AuNP)

Colloidal gold was prepared by reducing $HAuCl_4$ with sodium citrate. 50 mL of a 0.01% $HAuCl_4$ (0.243 mM) aqueous solution was boiled vigorously while stirring in a round-bottom flask equipped with a reflux condenser. Then, 10 mL of a 0.1% sodium citrate aqueous solution (3.4 mM) was added to the boiling $HAuCl_4$ solution. The color of the solution turned from yellow to deep purple and then to wine red within 3 minutes. The mixture was boiled further for 10 minutes and cooled to room temperature while continuously stirring overnight. The concentration of the colloidal gold was determined with a spectrophotometer.

3-2. Coating

It was investigated whether the gold nanoparticles (AuNP) prepared above are coated with the peptide-molecule conjugates prepared in Examples 1-3 (SAB1 to SAB3). First, the peptide-molecule conjugates of Examples 1-3 (SAB1 to SAB3) were dispersed in distilled water to prepare 20 μM aqueous solutions, respectively. After sonicating the SAB1 to SAB3 aqueous solutions (20 μM, 50 μL) for at least 5 minutes, they were immediately added to the AuNP solution (200 μL), respectively. After conducting reaction overnight and centrifuging at 16,100 g for 30 minutes, the reaction was resuspended in deionized water. After washing twice, the solution was analyzed by CD and TEM.

3-3. Analysis Result

Figure 13A:
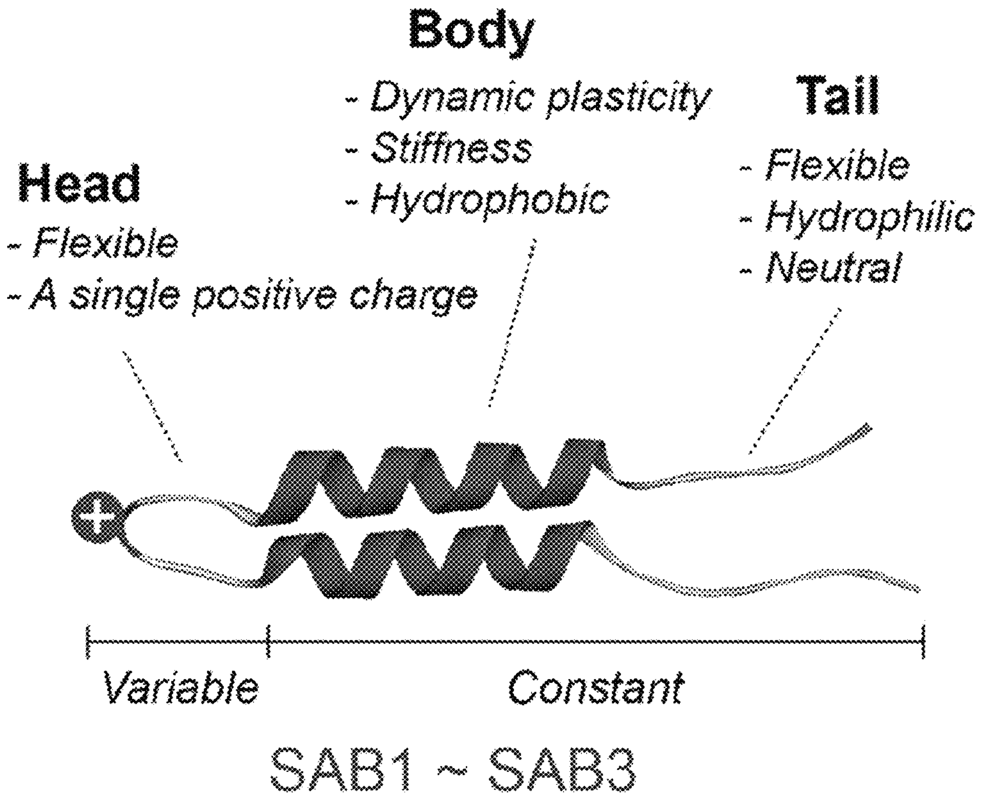
FIGS. 13A to 13D show results of identifying the structure of a nanostructure formed through self-assembly when a peptide-molecule conjugate (SAB1 to SAB3) is mixed with a gold nanoparticle and a double-stranded DNA (dsDNA).
Figure 13B:
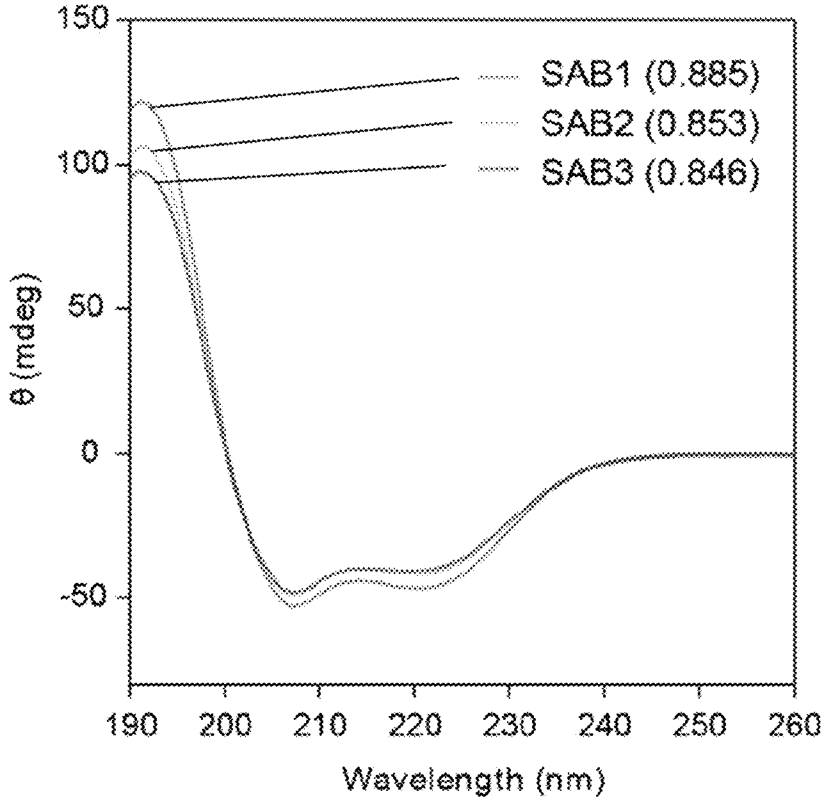
Figure 13C:
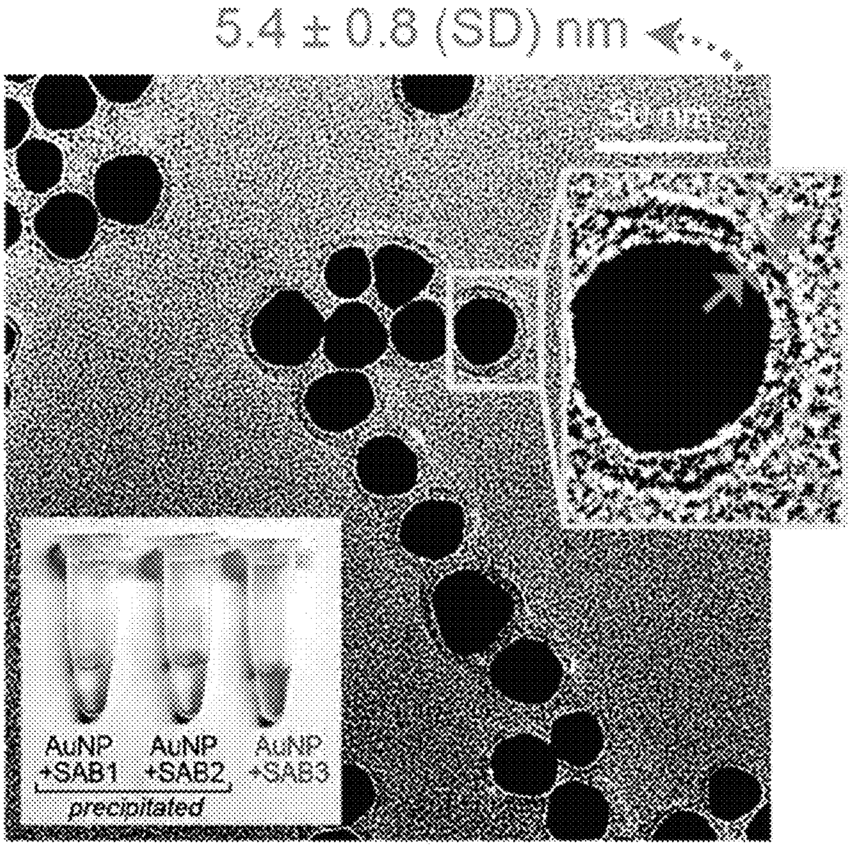
Figure 13D:
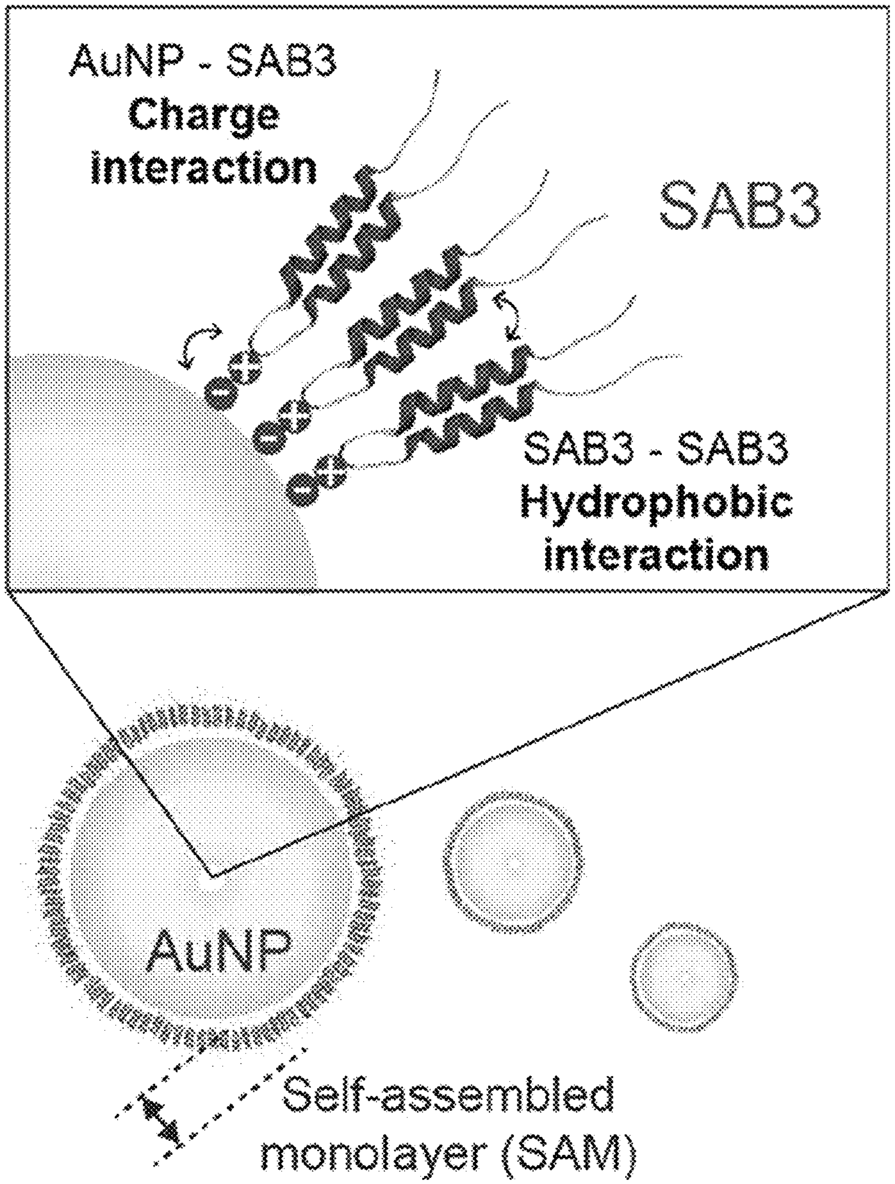

FIGS. 13A to 13D show results of identifying the structure of the nanostructures formed through self-assembly when the peptide-molecule conjugates (SAB1 to SAB3) were mixed with the gold nanoparticles and double-stranded DNA (dsDNA). FIG. 13A shows the structure of peptide-molecule conjugates (SAB1 to SAB3), and FIG. 13B shows the CD spectra of the peptide-molecule conjugates (SAB1 to SAB3) in an aqueous solution at 20° C. The numerical values in parentheses indicate helicities represented by $[\theta]_{222}/[\theta]_{208}$ ratios. FIG. 13C shows the negative-stain TEM image of the self-assembly nanostructure formed as the peptide-molecule conjugate of Example 3 (SAB3) surrounds the surface of the gold nanoparticles (AuNP). The insert image was obtained after adding peptide-molecule conjugates (SAB1 to SAB3) to the gold nanoparticle aqueous solution. FIG. 13D schematically shows the formation of a self-assembled monolayer (SAM) by the peptide-molecule conjugate of Example 3 (SAB3) on the surface of the gold nanoparticles (AuNP).

Figure 14:
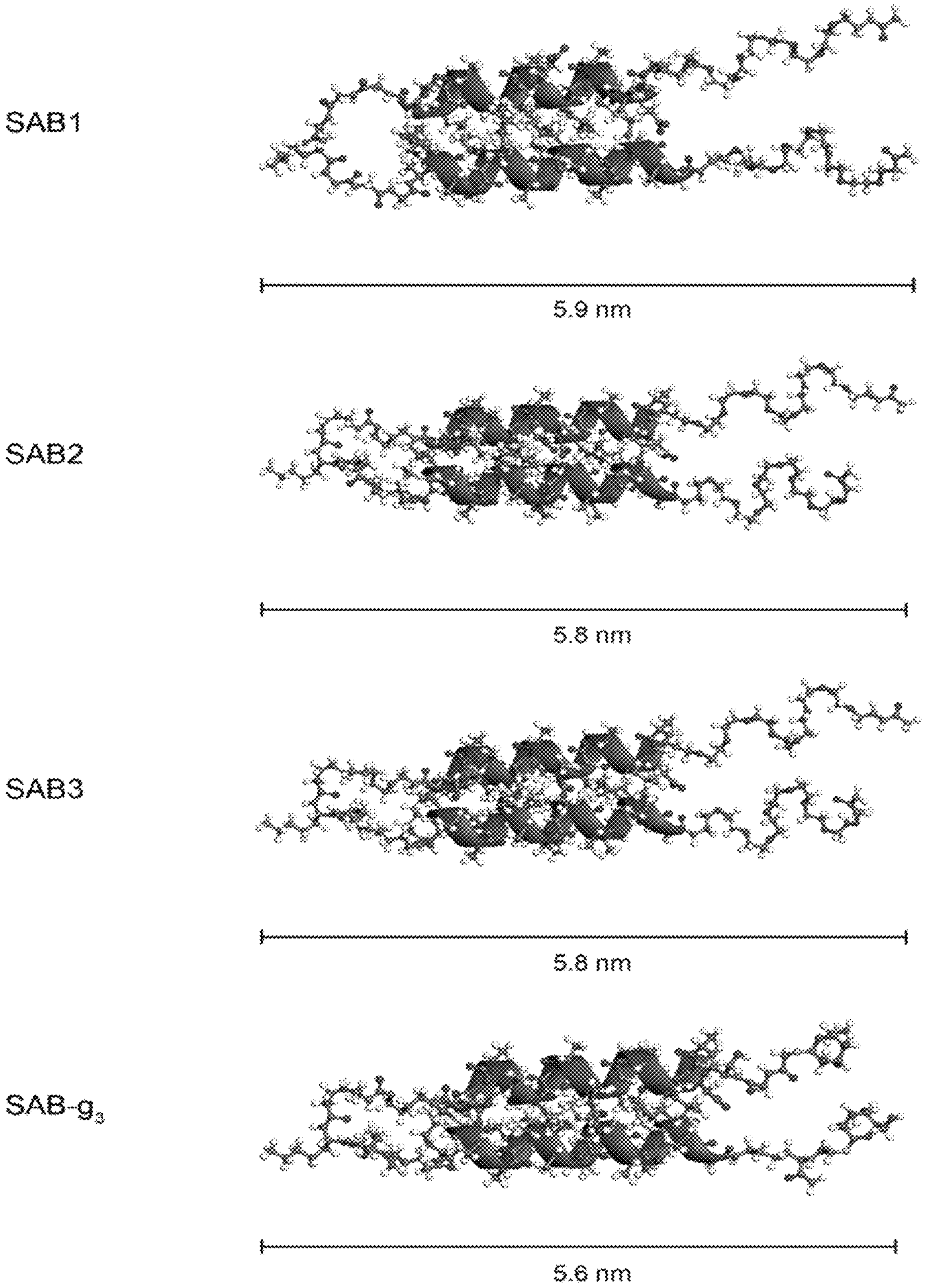
FIG. 14 shows a result of calculating the molecular length of peptide-molecule conjugates of Examples 1-3 (SAB1 to SAB3) in coiled coil states.

FIG. 14 shows a result of calculating the molecular length of the peptide-molecule conjugates of Examples 1-3 (SAB1 to SAB3) in coiled coil states. Specifically, the molecular length was calculated using the molecular modeling software, Discovery Studio 3.5.0.

From FIG. 13A, it can be seen that the peptide-molecule conjugate according to the present disclosure (SAB) is designed such that the structures of the body and tail moieties are constant and the head moiety, which is a linker connecting the first and second peptides, is variable.

From FIG. 13B, it was confirmed that all the peptide-molecule conjugates of Examples 1-3 (SAB1 to SAB3) maintain the helicity states well (($[\theta]_{222}/[\theta]_{208}$ ratios=0.8-0.9). This means that the α-helical coiled coil structures of the first and second peptides are successfully maintained in the peptide-molecule conjugates of Examples 1-3 (SAB1 to SAB3).

First, it was investigated whether gold nanoparticles can be coated with the peptide-molecule conjugate according to the present disclosures of Examples 1-3 (SAB1 to SAB3). As a result of adding the peptide-molecule conjugates of Examples 1-3 (SAB1 to SAB3) to a gold nanoparticle aqueous solution, it was confirmed that the peptide-molecule conjugates of Examples 1-3 (SAB1 to SAB3) successfully coat the surface of gold nanoparticles as single layers, as shown in FIG. 13C.

The gold nanoparticles were surface-modified using citrate to exhibit negative charge. However, for the peptide-molecule conjugates of Examples 1 and 2 (SAB1, SAB2), precipitates were formed due to aggregation of the gold nanoparticles. Accordingly, it was confirmed that use of the peptide-molecule conjugate of Example 3 (SAB3) is preferable in terms of dispersibility for nanoparticles such as gold nanoparticles.

Referring to FIG. 13D, the peptide-molecule conjugate of Example 3 (SAB3) is bound to the surface of negatively charged gold nanoparticles (AuNP) through electrostatic interaction between the positively charged linker (head) of the peptide-molecule conjugate of Example 3 (SAB3) and the surface of the gold nanoparticles. The peptide-molecule conjugate of Example 3 (SAB3) is tightly bound due to the hydrophobic interaction between the first and second peptides. Through this, the peptide-molecule conjugate according to the present disclosure of Example 3 (SAB3) forms a single self-assembled monolayer by surrounding the surface of the gold nanoparticles by simple mixing only without use of an additional catalyst or a binding process, thereby forming nanostructures with the gold nanoparticles. The thickness of the self-assembled monolayer of the peptide-molecule conjugate (SAB3) formed on the surface of the gold nanoparticles was measured as shown in FIG. 13C. The thickness of the self-assembled monolayer was 5.4±0.8 (SD) nm. It was confirmed that self-assembled monolayers of uniform size were formed also on other gold nanoparticles.

The molecular length of the peptide-molecule conjugate (SAB3) was measured to investigate whether the layer formed by the peptide-molecule conjugate (SAB3) is a single layer or a multiple layer. As shown in FIG. 14, the molecular length of the peptide-molecule conjugate (SAB1 to SAB3, SAB-$g_3$) was 5.6-5.9 nm, and the average molecular length of the peptide-molecule conjugate (SAB3) was 5.8 nm. From these results, it was confirmed that the molecular length of the peptide-molecule conjugate (SAB3) corresponds to the monolayer thickness of the gold nanoparticle nanostructure, suggesting that the gold nanoparticles are coated with a single layer of the peptide-molecule conjugate (SAB3).

Test Example 4. Formation of Nanostructure for dsDNA Using Peptide-Molecule Conjugate (SAB)

It was investigated whether the peptide-molecule conjugate (SAB) forms a self-assembled monolayer also for double-stranded DNA (dsDNA). Unlike for gold nanoparticles, the peptide-molecule conjugate exists as a fibrous nanostructure for dsDNA.

For this, a pTWIN1 plasmid DNA vector was purchased from New England BioLabs (Ipswich, USA), genetically recombined to express a specific protein (Rev), and then linearized with a BamH1 restriction enzyme purchased from the same company to prepare a linear double-stranded DNA (dsDNA) (7528 base pairs). The peptide-molecule conjugates of Examples 1-3 (SAB1 to SAB3) were dispersed in distilled water to prepare 20 μM aqueous solutions. The SAB1 to SAB3 aqueous solutions (20 μM, 50 μL) were sonicated for at least 5 minutes and then immediately added to the dsDNA solution (200 μL). The concentration of the dsDNA was fixed while the concentration of the peptide-molecule conjugate (SAB) was varied by concentration or dilution. The dsDNA and the peptide-molecule conjugate of Example 2 (SAB2) were mixed such that the charge ratio (+/−) was 0, 0.008, 0.016, 0.031, 0.063, 0.125, 0.25, 0.5, 1, 2, 4, 8, 16, 32 and 64. A SAB2/dsDNA nanostructure was prepared by incubating the mixture overnight. Then, after centrifuging at 16,100 g for 30 minutes, the nanostructure was resuspended in deionized water. After washing twice, the nanostructure was analyzed by TEM and EMSA.

Figure 15A:
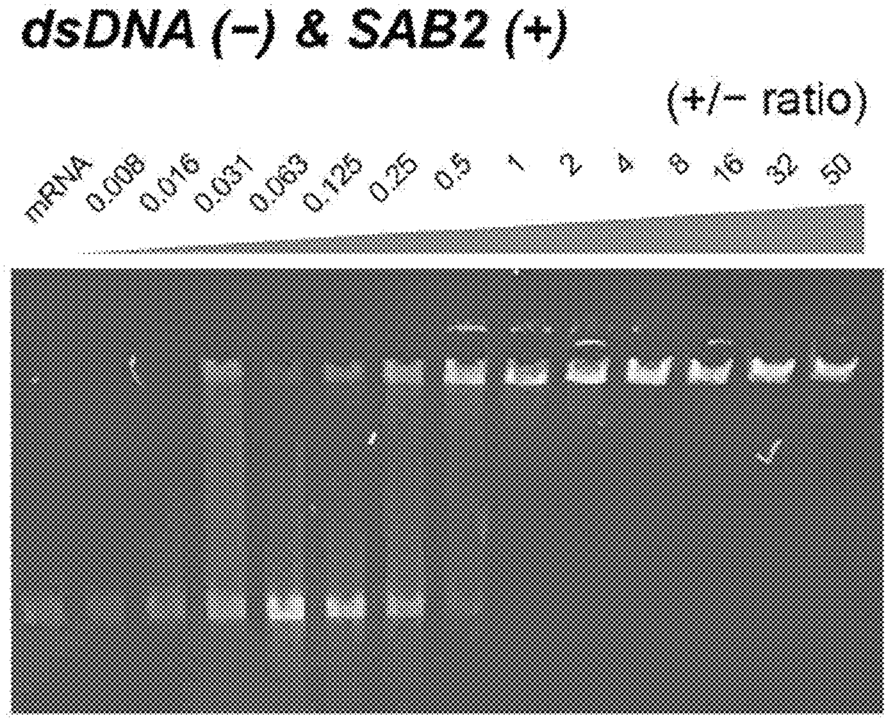
FIG. 15A shows an EMSA result of detecting the formation of a nanostructure through self-assembly after addition of a peptide-molecule conjugate of Example 2 (SAB2) of different concentrations to dsDNA.
Figure 15B:
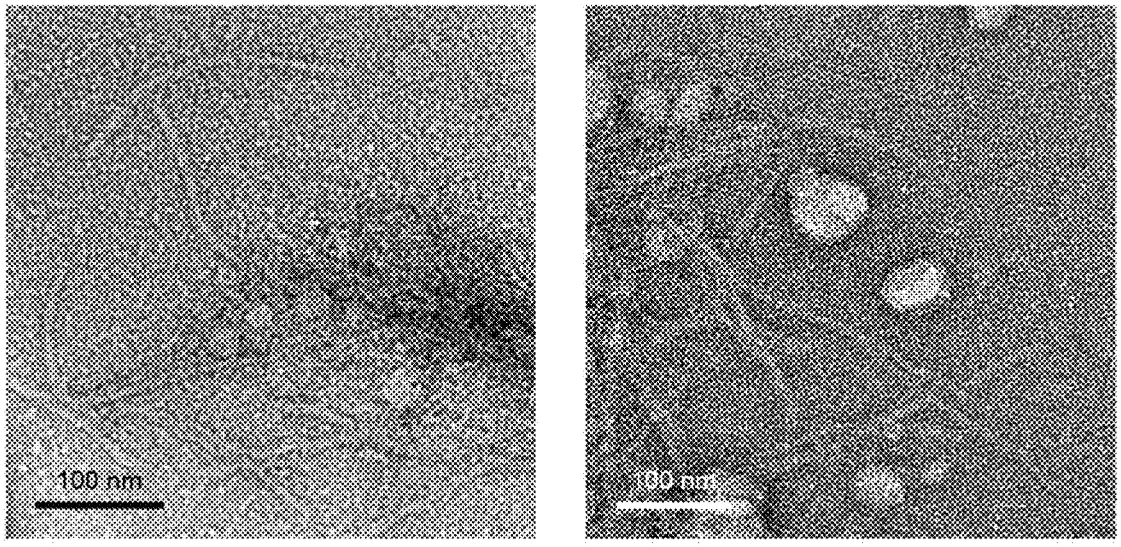
FIG. 15B show the TEM images of a SAB2/dsDNA (+/−=1) nanostructure showing that the fibrous nanostructure of the dsDNA is maintained.
Figure 15C:
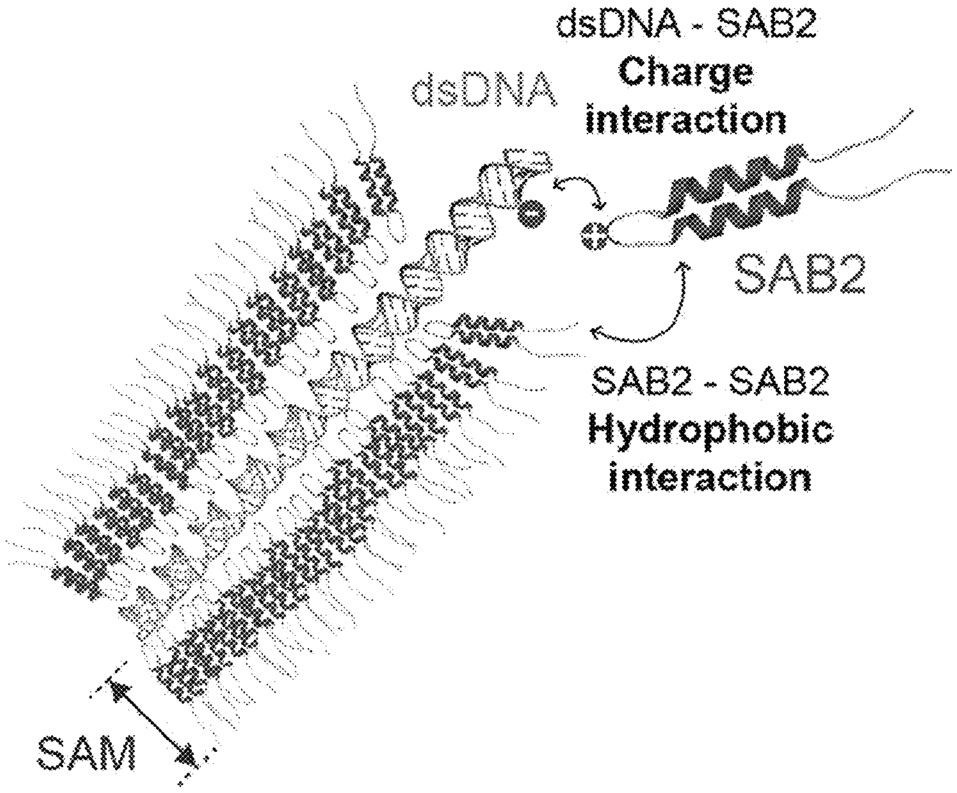
FIG. 15C schematically shows the self-assembly of a SAB2/dsDNA nanostructure.

FIG. 15A shows an EMSA result of detecting the formation of a nanostructure through self-assembly after addition of the peptide-molecule conjugate of Example 2 (SAB2) of different concentrations to dsDNA. FIG. 15B show the TEM images of the SAB2/dsDNA (+/−=1) nanostructure showing that the fibrous nanostructure of the dsDNA is maintained. FIG. 15C schematically shows the self-assembly of the SAB2/dsDNA nanostructure.

When the peptide-molecule conjugate according to the present disclosures of Examples 1-3 (SAB1 to SAB3) were added to the linear double-stranded DNA (dsDNA), all the peptide-molecule conjugates (SAB1 to SAB3) self-assembled to form nanostructures. But, the peptide-molecule conjugate of Example 2 (SAB2) showed the best result. Therefore, the peptide-molecule conjugate of Example 2 (SAB2) was used in the examples using nucleic acid materials.

From FIG. 15A, it can be seen that the EMSA band is delayed gradually as the concentration of the peptide-molecule conjugate of Example 2 (SAB2) is increased. Through this, it can be seen that the peptide-molecule conjugate of Example 2 (SAB2) forms a nanostructure through self-assembly with dsDNA. Specifically, the delay of band was observed from when the charge ratio (+/−) was 0.031. When the charge ratio was 0.5, the SAB2/dsDNA nanostructure was prepared through self-assembly of the peptide-molecule conjugate of Example 2 (SAB2) and dsDNA.

From FIG. 15B, it was confirmed that the peptide-molecule conjugate of Example 2 (SAB2) and dsDNA form the SAB2/dsDNA nanostructure through self-assembly, and the nanostructure is in the form of a fibrous nanostructure. It is because the peptide-molecule conjugate of Example 2 (SAB2) is coated on the fibrous structure of the dsDNA.

From FIG. 15C, it can be seen that the SAB2/dsDNA nanostructure formed from the peptide-molecule conjugate of Example 2 (SAB2) and the dsDNA also contains a self-assembled monolayer coated on the dsDNA through electrostatic and hydrophobic interactions.

Test Example 5. Analysis of Helicity of Peptide-Molecule Conjugates of Examples 4-9 (SAB-$g_n$, n=1 to 6)

In Test Example 4, it was confirmed that the peptide-molecule conjugates (SABs) were successfully coated on nucleic acid materials such as dsDNA, and the peptide-molecule conjugate prepared in Example 2 (SAB2) is the most suitable among them. Therefore, experiment was performed using the peptide-molecule conjugate prepared in Example 2 (SAB2).

Figure 16:
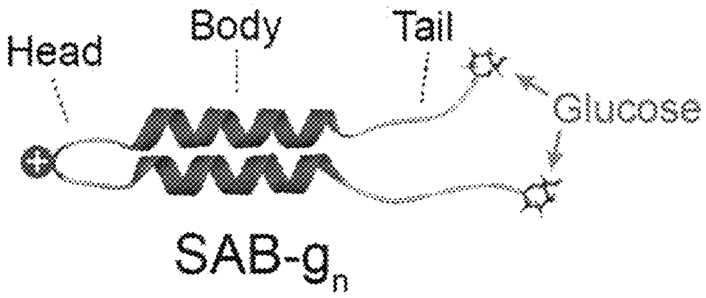
FIG. 16 schematically shows the chemical structure of peptide-molecule conjugates of Examples 4-9 (SAB-$g_n$, n=1 to 6).

Six derivatives (analogues) were designed using the peptide-molecule conjugate prepared in Example 2 (SAB2), and the peptide-molecule conjugates of Examples 4-9 (SAB-$g_n$, n=1 to 6) were prepared (FIG. 16).

Glucose is bound to the tail domain of the peptide-molecule conjugates of Examples 4-9 (SAB-$g_n$, n=1 to 6) as a hydrophilic molecule for cell targeting. Glucose is known as a targeting ligand binding to GLUT-1 overexpressed in endothelial cells in the blood-brain barrier and cancer cells. After adding the peptide-molecule conjugates of Examples 4-9 (SAB-$g_n$, n=1 to 6) in distilled water and storing for 20° C., they were analyzed by CD (circular dichroism) spectroscopy.

Figure 17:
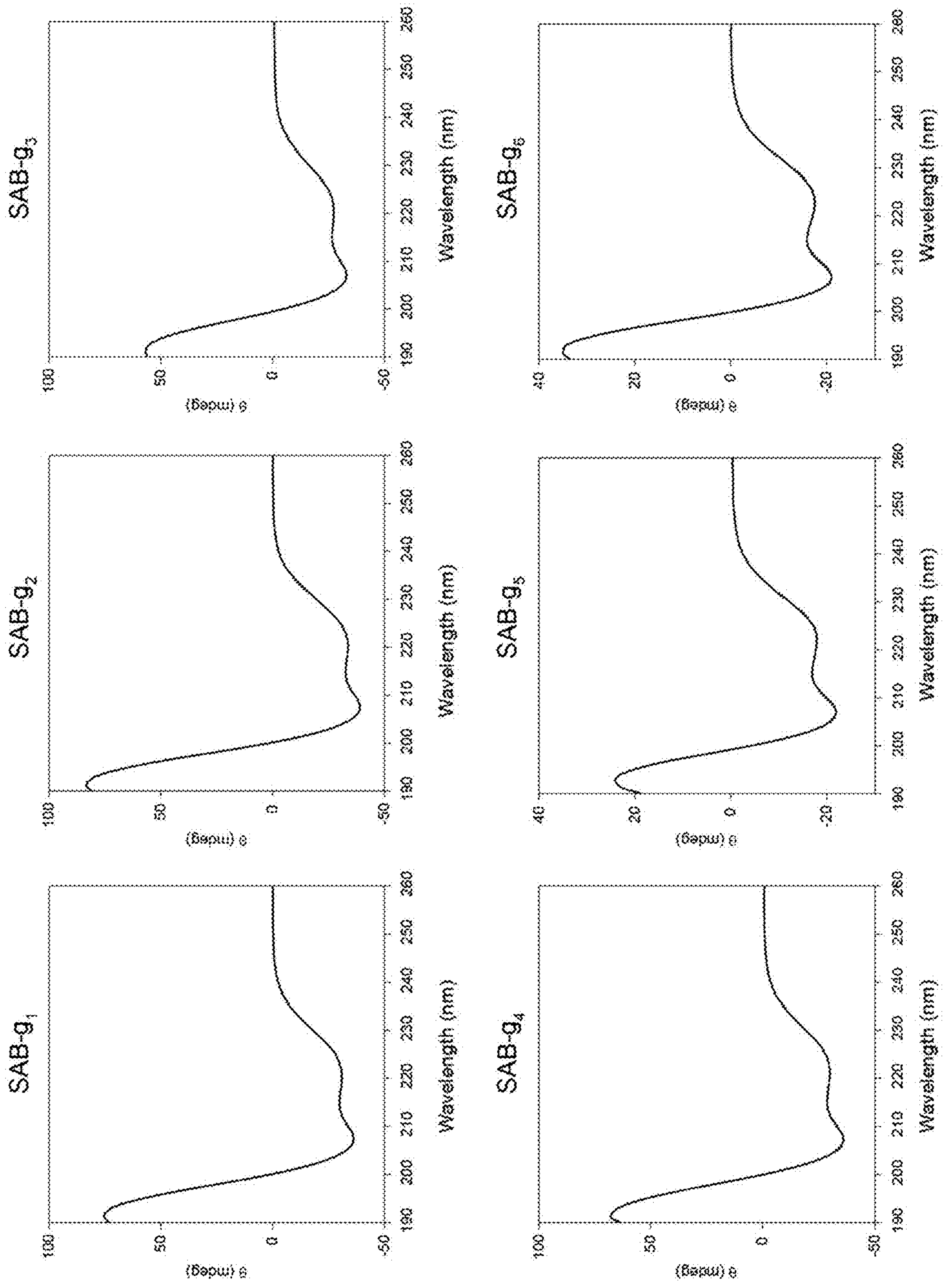
FIG. 17 shows the CD spectra of peptide-molecule conjugates of Examples 4-9 (SAB-$g_n$, n=1 to 6) in an aqueous solution at 20° C.

FIG. 16 schematically shows the chemical structure of the peptide-molecule conjugates of Examples 4-9 (SAB-$g_n$, n=1 to 6), and FIG. 17 shows the CD spectra of the peptide-molecule conjugates of Examples 4-9 (SAB-$g_n$, n=1 to 6) in an aqueous solution at 20° C.

From FIG. 17, it can be seen that the peptide-molecule conjugates of Examples 4-9 (SAB-$g_n$, n=1 to 6) have superior helicity.

Test Example 6. Formation of Nanostructures for mRNA Using Peptide-Molecule Conjugates (SAB)

20 μM aqueous solutions were prepared by dispersing the peptide-molecule conjugates of Example 2 and Examples 4-9 (SAB2, SAB-$g_n$, n=1 to 6) in distilled water. After sonicating the peptide-molecule conjugate (SAB-$g_n$, n=1 to 6) aqueous solution for 5 minutes, it was immediately mixed with an EGFP mRNA (200 μL) solution. The EGFP mRNA was CleanCap® enhanced green fluorescent protein (EGFP) mRNA (5-methoxyuridine) (Catalog No.: L-7601) purchased from TriLink BioTechnologies (San Diego, USA). An SAB-$g_n$/dsDNA nanostructure was prepared as follows by mixing the peptide-molecule conjugate (SAB-$g_n$, n=1 to 6) with the EGFP mRNA. The concentration of the EGFP mRNA was fixed while the concentration of the peptide-molecule conjugate (SAB-$g_n$, n=1 to 6) was varied by concentration or dilution. The EGFP mRNA and the peptide-molecule conjugate (SAB-$g_n$, n=1 to 6) were mixed at a charge ratio (+/−) of 0, 0.008, 0.016, 0.031, 0.063, 0.125, 0.25, 0.5, 1, 2, 4, 8, 16, 32 or 50. Because the peptide-molecule conjugate (SAB-$g_n$, n=1 to 6) has one positive charge in the head domain and the EGFP mRNA has 996 negative charges, the charge ratio was calculated based thereon.

After incubating the mixture solution overnight and centrifuging at 16,100 g for 30 minutes, the mixture was resuspended in deionized water. After washing twice, the resulting nanostructure was analyzed by EMSA.

From the EMSA result for the samples, the optimum charge ratios (+/−) of the EGFP mRNA and the peptide-molecule conjugate (SAB-$g_n$, n=1 to 6) showing completely delayed electrophoretic mobility are shown in Table 2. The complete delay of electrophoretic mobility means that the SAB-$g_n$/dsDNA nanostructure was formed through self-assembly of the EGFP mRNA and the peptide-molecule conjugate (SAB-$g_n$, n=1 to 6).

TABLE 2

| Building blocks | +/− |
|---|---|
| SAB2 | 30 |
| SAB-$g_1$ | 20 |
| SAB-$g_2$ | >30 |
| SAB-$g_3$ | 0.25 |
| SAB-$g_4$ | 5 |
| SAB-$g_5$ | 10 |
| SAB-$g_6$ | >4 |

From Table 2, it was confirmed that SAB-$g_n$/dsDNA nanostructures are formed from self-assembly with mRNA when the peptide-molecule conjugates of Example 2 and Examples 4-9 (SAB2, SAB-$g_n$, n=1 to 6) are used as building blocks. However, the mixing charge ratio for completely forming the nanostructures is different depending on the peptide-molecule conjugate (SAB-$g_n$, n=1 to 6). Among them, the peptide-molecule conjugate of Example 6 (SAB-$g_3$) could form the nanostructure with mRNA at the lowest concentration. Therefore, the peptide-molecule conjugate of Example 6 (SAB-$g_3$) was used in the following experiments as the peptide-molecule conjugate.

Test Example 7. Structural Analysis of Nanostructure of Peptide-Molecule Conjugate (SAB) and mRNA A 20 μM aqueous solution was prepared by dispersing the peptide-molecule conjugate of Example 6 (SAB-$g_3$) in distilled water. After sonicating the peptide-molecule conjugate of Example 6 (SAB-$g_3$) aqueous solution for 5 minutes, it was immediately mixed with an EGFP mRNA (200 μL) solution. The EGFP mRNA was CleanCap® enhanced green fluorescent protein (EGFP) mRNA (5-methoxyuridine) (Catalog No.: L-7601) purchased from TriLink BioTechnologies (San Diego, USA). The peptide-molecule conjugate of Example 6 (SAB-$g_3$) and the EGFP mRNA were mixed as follows. The concentration of the EGFP mRNA was fixed while the concentration of the peptide-molecule conjugate of Example 6 (SAB-$g_3$) was varied by concentration or dilution. The EGFP mRNA and the peptide-molecule conjugate (SAB-$g_3$) were mixed at a charge ratio (+/−) of 0, 0.008, 0.016, 0.031, 0.063, 0.125, 0.25, 0.5, 1, 2, 4, 8, 16, 32 or 50. Because the peptide-molecule conjugate of Example 6 (SAB-$g_3$) has one positive charge in the head domain and the EGFP mRNA has 996 negative charges, the charge ratio was calculated based thereon.

After incubating the mixture solution overnight and centrifuging at 16,100 g for 30 minutes, the mixture was resuspended in deionized water. After washing twice, SAB-$g_3$/mRNA nanostructures were prepared at different charge ratios, and they were analyzed by TEM and EMSA. Since the prepared SAB-$g_3$/mRNA nanostructures were formed along the mRNA nanofiber, they are in the form of nanotubes. Therefore, the SAB-$g_3$/mRNA nanostructure is also referred to as an SAB nanotube.

Figure 18:
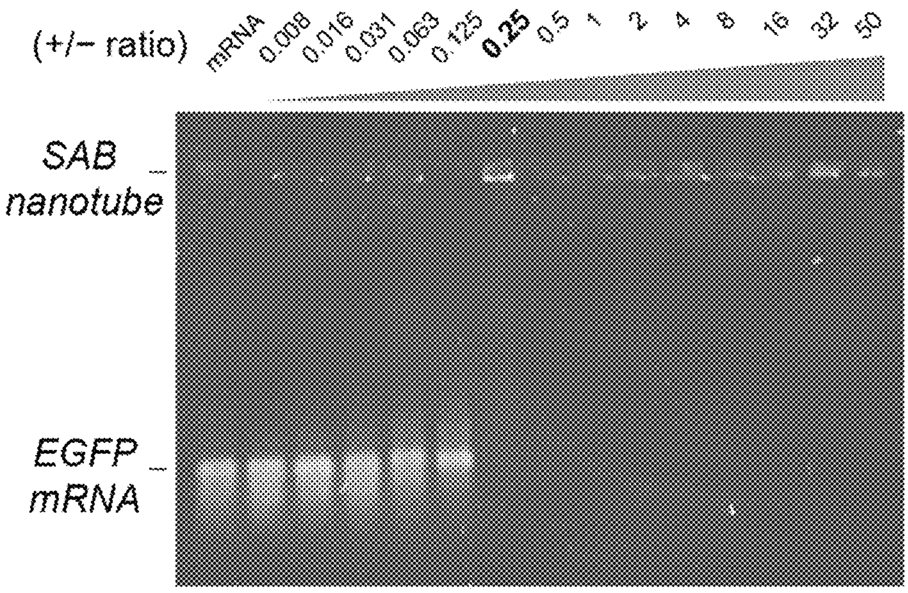
FIG. 18 shows an EMSA result for nanostructures prepared by mixing a peptide-molecule conjugate of Example 6 (SAB-$g_3$) with an EGFP mRNA at different charge ratios (+/−).
Figure 19:
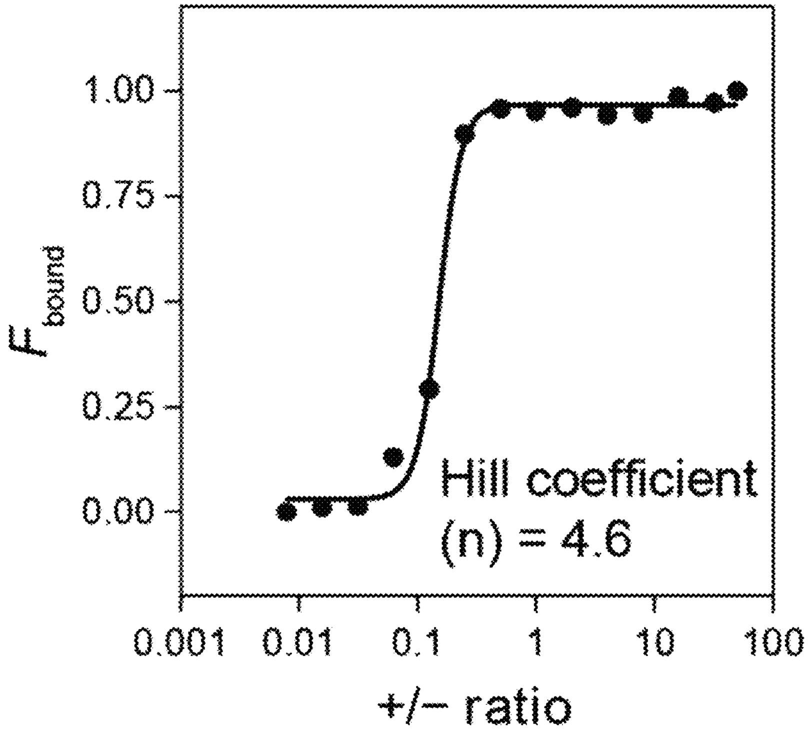
FIG. 19 shows a result of analyzing the degree of binding ($F_{bound}$) of a nanostructure of a peptide-molecule conjugate of Example 6 (SAB-$g_3$) and an EGFP mRNA from EMSA data. The Hill coefficient was calculated from the Hill equation represented by Equation 1. $F_{bound}$ is the fraction of mRNA bound by SAB-$g_3$, and $K_{SAB\text{-}g3}$ is the half-saturation constant, which is 0.152.

FIG. 18 shows the EMSA result for the nanostructures prepared by mixing the peptide-molecule conjugate of Example 6 (SAB-$g_3$) with the EGFP mRNA at different charge ratios (+/−), and FIG. 19 shows the result of analyzing the degree of binding ($F_{bound}$) of the nanostructure of the peptide-molecule conjugate of Example 6 (SAB-$g_3$) and the EGFP mRNA from EMSA data. The Hill coefficient was calculated from the Hill equation represented by Equation 1. $F_{bound}$ is the fraction of mRNA bound by SAB-$g_3$, and $K_{SAB\text{-}g3}$ is the half-saturation constant, which is 0.152.

$$y=x^n/(K_{SAB\text{-}g3}{}^n+x^n) \quad \text{[Equation 1]}$$

As shown in FIG. 18, when the peptide-molecule conjugate of Example 6 (SAB-$g_3$) was mixed with the EGFP mRNA at various charge ratios (+/−) and analyzed by EMSA, it was confirmed that complete nanostructures were formed at the charge ratio of 0.25.

As shown in FIG. 19, the mRNA binding graph showed a very sharp sigmoid curve. The Hill coefficient was calculated very high as 4.6, suggesting that he peptide-molecule conjugate of the present disclosure (SAB-$g_3$) exhibits strong charge interaction for binding to the mRNA.

Figure 20:
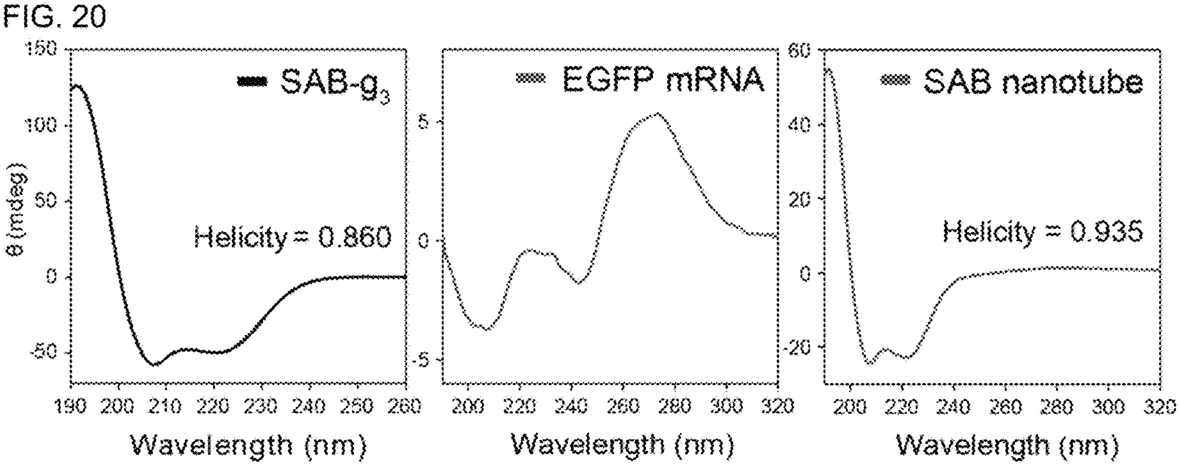
FIG. 20 shows the CD spectra of a nanostructure (SAB nanotube) prepared by mixing a peptide-molecule conjugate of Example 6 (SAB-$g_3$) and an EGFP mRNA at a charge ratio (+/−) of 0.25 in an aqueous solution at 20° C.

FIG. 20 shows the CD spectra of the nanostructure (SAB nanotube) prepared by mixing the peptide-molecule conjugate of Example 6 (SAB-$g_3$) and the EGFP mRNA at a charge ratio (+/−) of 0.25 in an aqueous solution at 20° C. FIG. 20 also shows the CD spectra of the peptide-molecule conjugate of Example 6 (SAB-$g_3$) and the EGFP mRNA, denoted as 'SAB-$g_3$' and 'EGFP mRNA', respectively.

As shown in FIG. 20, the self-assembly of the peptide-molecule conjugate of Example 6 (SAB-$g_3$) and the EGFP mRNA leads to further increase in the affinity for the peptide-molecule conjugate of Example 6 (SAB-$g_3$) and formation of a self-assembled monolayer as the peptide-molecule conjugate of Example 6 (SAB-$g_3$) surrounds the mRNA through hydrophobic interaction. Through this process, the peptide-molecule conjugate of Example 6 (SAB-$g_3$) has higher helicity after binding to the EGFP mRNA (0.935).

Figure 21:
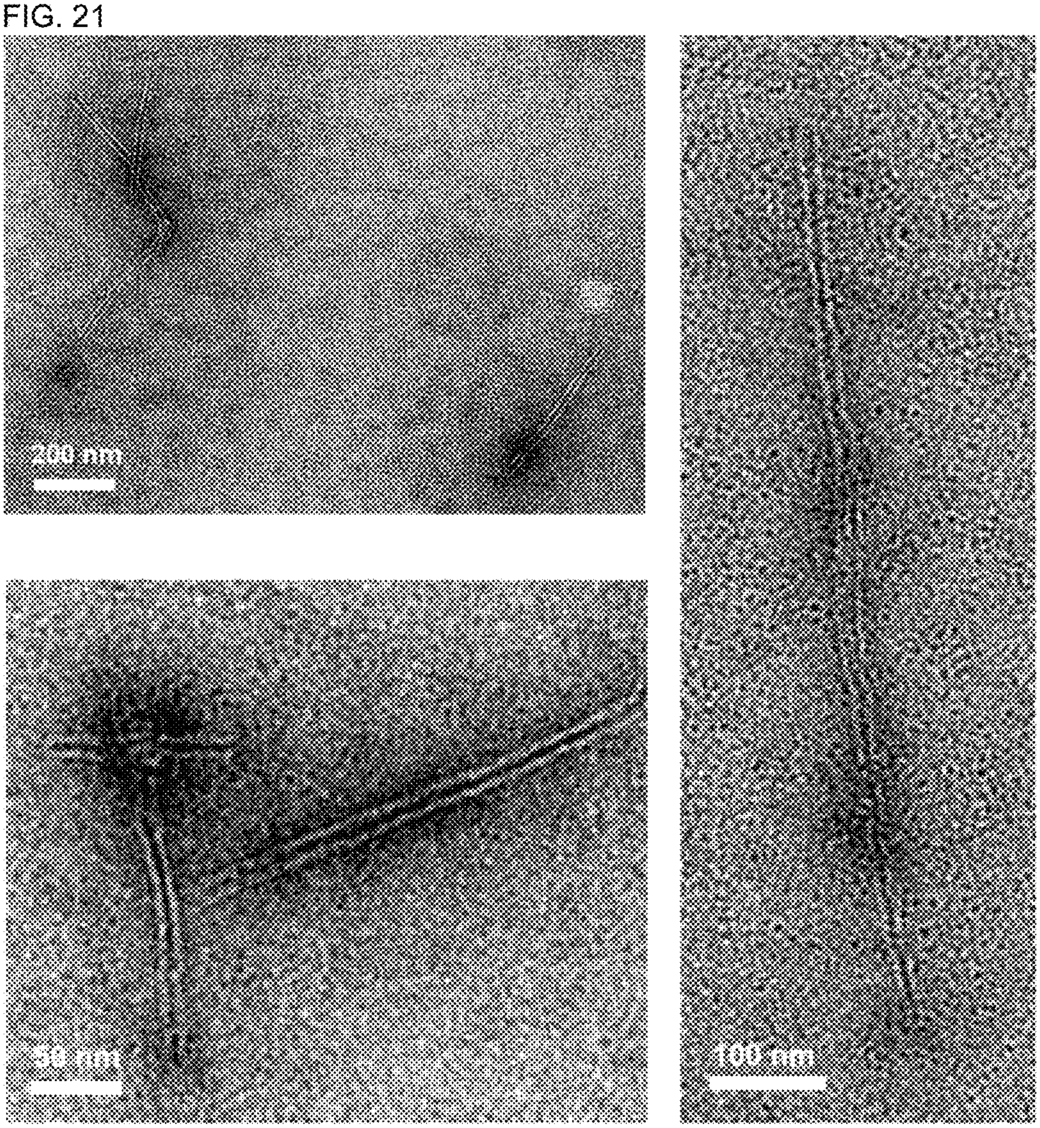
FIG. 21 shows the TEM images of a nanostructure prepared by mixing a peptide-molecule conjugate of Example 6 (SAB-$g_3$) and an EGFP mRNA at a charge ratio (+/−) of 0.25.

FIG. 21 shows the TEM images of the nanostructure prepared by mixing the peptide-molecule conjugate of Example 6 (SAB-$g_3$) and the EGFP mRNA at a charge ratio (+/−) of 0.25.

From FIG. 21, it was confirmed that the nanostructure of the peptide-molecule conjugate of Example 6 (SAB-$g_3$) and the EGFP mRNA is in the form of a nanotube with an average diameter of 17 nm. The core (mRNA) had a diameter of 5 nm and the self-assembled monolayer had an average thickness of 6 nm.

The nanostructure of the peptide-molecule conjugate according to the present disclosure of Example 6 (SAB-$g_3$) and the EGFP mRNA is in the form of a nanotube like tobacco mosaic virus (TMV). A carrier of mRNA that artificially forms a nanotube has never been reported. In addition, the nanostructure of the peptide-molecule conjugate of the present disclosure of Example 6 (SAB-$g_3$) and the EGFP mRNA was confirmed to exist as bent or curved in solution, suggesting that it is more flexible than TMV.

Whereas TMV has a structure wherein the coat protein spirally surrounds the single-strained RNA genome of the virus, the peptide-molecule conjugate of the present disclosure of Example 6 (SAB-$g_3$) coats the mRNA much more stably and densely as it surrounds the mRNA spirally and interacts cooperatively with the mRNA through electrostatic and hydrophobic interaction.

Figure 22A:
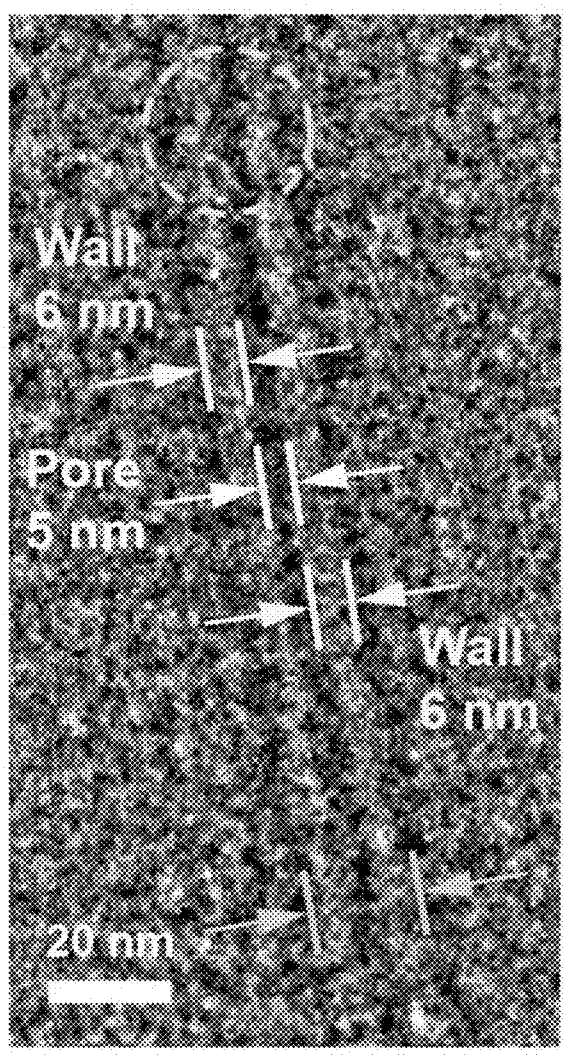
FIGS. 22A to 22C show the 3D structure of a nanostructure prepared by mixing a peptide-molecule conjugate of Example 6 (SAB-$g_3$) with an EGFP mRNA at a charge ratio (+/−) 0.25.
Figure 22B:
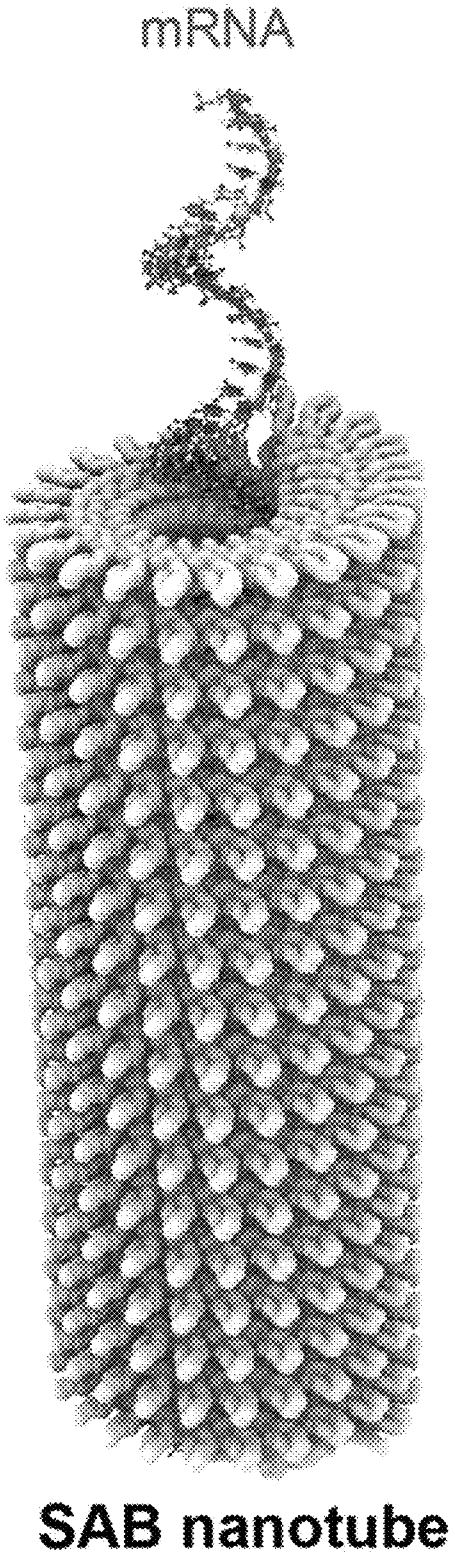
Figure 22C:
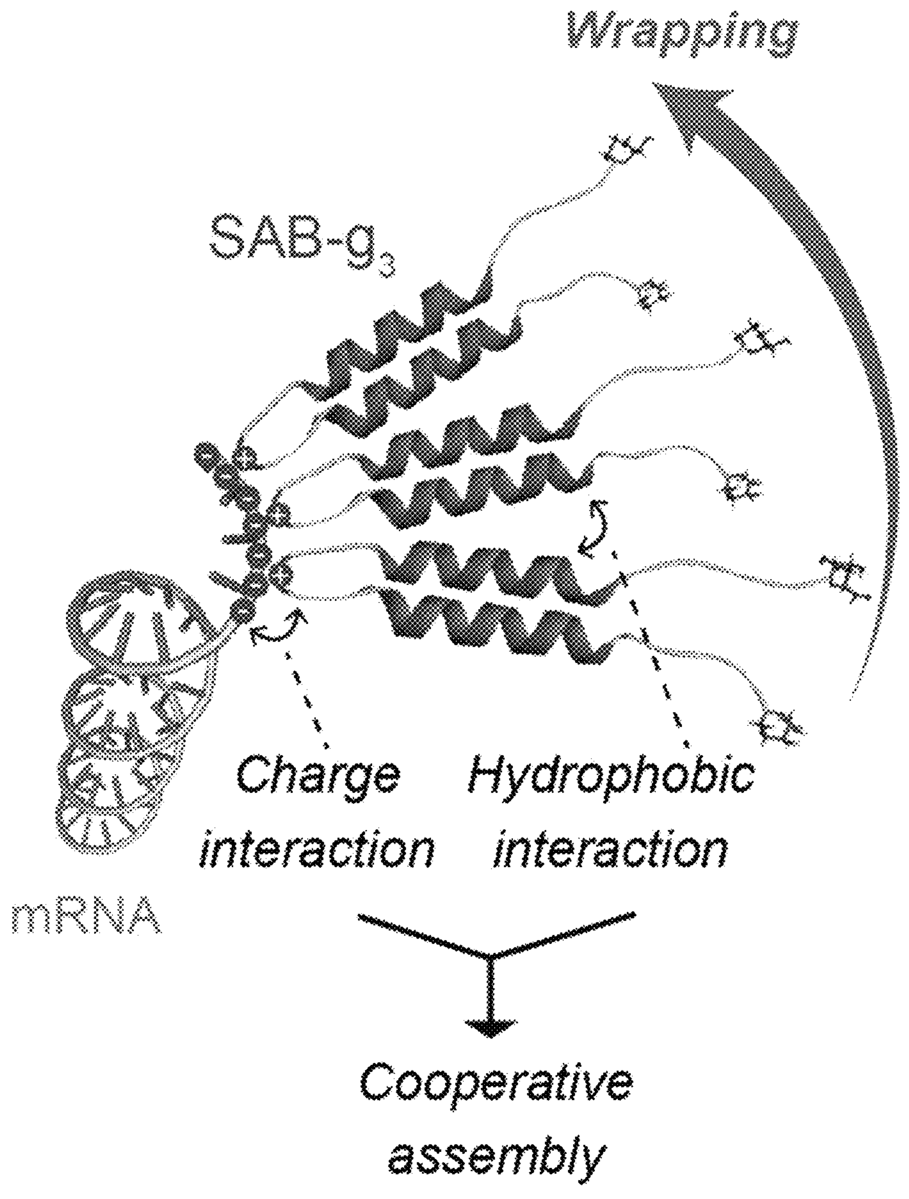

FIGS. 22A to 22C show the 3D structure of the nanostructure prepared by mixing the peptide-molecule conjugate of Example 6 (SAB-$g_3$) with the EGFP mRNA at a charge ratio (+/−) 0.25. FIG. 22A is the TEM image showing the diameter and monolayer thickness of the nanostructure of SAB-$g_3$ and EGFP mRNA (+/−=0.25), FIG. 22B shows the structural model of the nanostructure of SAB-$g_3$ and EGFP mRNA (+/−=0.25), and FIG. 22C schematically shows the formation of the nanostructure of SAB-$g_3$ and EGFP mRNA (+/−=0.25).

Based on these results, the binding of the peptide-molecule conjugate of the present disclosure (SAB-$g_3$) and the EGFP mRNA is schematically shown in FIGS. 22A to 22C. The peptide-molecule conjugate of the present disclosure (SAB-$g_3$) and the EGFP mRNA form a nanostructure through self-assembly via hydrophobic interaction and positive binding cooperativity in addition to electrostatic interaction. Due to superior stability, the peptide-molecule conjugate can coat mRNA densely without restricting the motion of the mRNA in solution. Accordingly, it can store the nucleic acid material such as mRNA safely while providing superior function for activity.

Test Example 8. Intracellular Delivery Pathway of Nanostructure of Peptide-Molecule Conjugate (SAB) and mRNA 8-1. Preparation of Nanostructure of Peptide-Molecule Conjugate (SAB) and mRNA The intracellular delivery effect of the nanostructure of the peptide-molecule conjugate (SAB) and mRNA was investigated. Control groups were treated with nothing (mock) or only with Cy5-AS-EGFP mRNA (mRNA only).

As the EGFP mRNA, Cy5-labeled EGFP mRNA (hereinafter, referred to as 'Cy5-AS-EGFP mRNA') hybridized with a Cy5-labeled oligonucleotide probe was used. Specifically, the Cy5-AS-EGFP mRNA was prepared using a Cy5-labeled antisense oligonucleotide (Cy5-AS: /5Cy5/GCG AGC TGC ACG CTG CCG TC) (SEQ ID NO: 18) and EGFP mRNA. First, after mixing Cy5-AS and EGFP mRNA of the same volumes and concentrations, the Cy5-AS-EGFP mRNA was prepared by heating the mixture for 3 minutes at 94° C. and slowly cooling at room temperature.

The peptide-molecule conjugate prepared in Example 6 (SAB) and the Cy5-AS-EGFP mRNA were mixed in distilled water at a charge ratio (+/− ratio) of 0.125 and 0.25, respectively. After heating the mixture for 10 minutes at 70° C., it was snap-cooled on ice. After incubation at room temperature for 1 hour, the sample immersed in deionized water was diluted 5-fold with Opti-MEM to prepare an SAB-$g_3$/mRNA nanostructure sample. Immediately before the mixing, the peptide-molecule conjugate prepared in Example 6 (SAB) was sonicated for 5 minutes.

8-2. Intracellular Delivery Efficiency

HeLa (ATCC CCL-2) cells were used. The Hela cells were cultured in DMEM (Dulbecco's modified Eagle's medium) containing 10% (v/v) FBS and penicillin-streptomycin.

After seeding $1\times10^4$ HeLa cells in each well of a 96-well cell culture plate (SPL, Pocheon, Korea) and culturing for 24 hours, the sample (200 μL) or the control substance (200 μL) was added to each well and the cells were cultured for 2 hours. The amount of mRNA added to each well was 1 μg. The 96-well cell culture plate (SPL, Pocheon, Korea) and a Nunc™ Lab-Tek™ II chambered coverglass (Thermo Scientific, Waltham, USA) were used for flow cytometry and confocal microscopy. The procedures of the flow cytometry and confocal microscopy are described in detail above in the Experimental methods section.

8-3. Analysis Result

Figure 23:
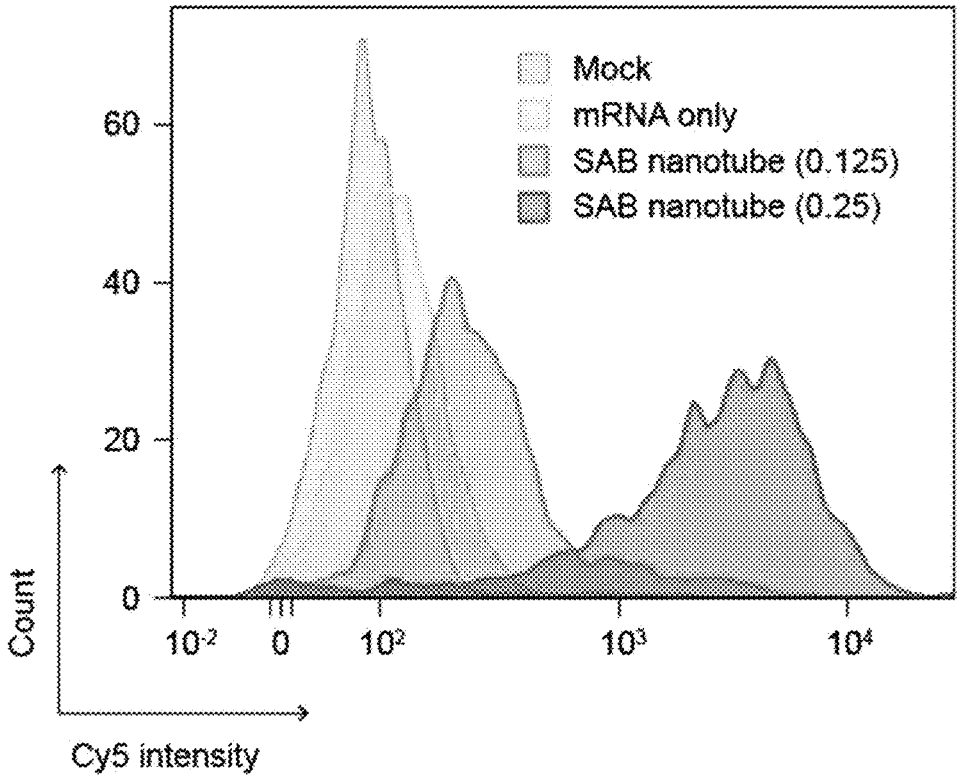
FIG. 23 shows a result of treating Hela cells with a nanostructure (SAB nanotube) of a peptide-molecule conjugate (SAB) and an mRNA and then conducting flow cytometry to investigate intracellular delivery rate.
Figure 24:
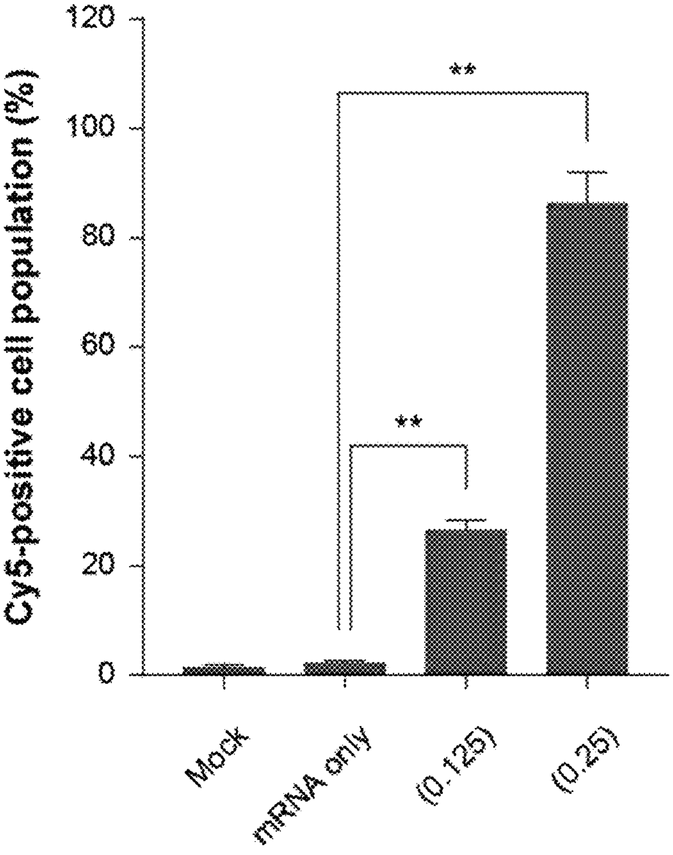
FIG. 24 shows a quantitative analysis result for the flow cytometry result of FIG. 23. Mean±SD (n=3). **P<0.01.

FIG. 23 shows a result of treating Hela cells with the nanostructure (SAB nanotube) of the peptide-molecule conjugate (SAB) and the mRNA and then conducting flow cytometry to investigate intracellular delivery rate. FIG. 24 shows a quantitative analysis result for the flow cytometry result of FIG. 23. Mean±SD (n=3). **P<0.01.

As shown in FIG. 23 and FIG. 24, for the control group treated only with the Cy5-AS-EGFP mRNA, intracellular delivery was observed only partially. The SAB-$g_3$/mRNA nanostructure (SAB nanotube) (charge ratio 0.125) was delivered to 50% or more of cells and the SAB-$g_3$/mRNA nanostructure (SAB nanotube) (charge ratio 0.25) was delivered effectively to 80% or more of cells.

Figure 25:
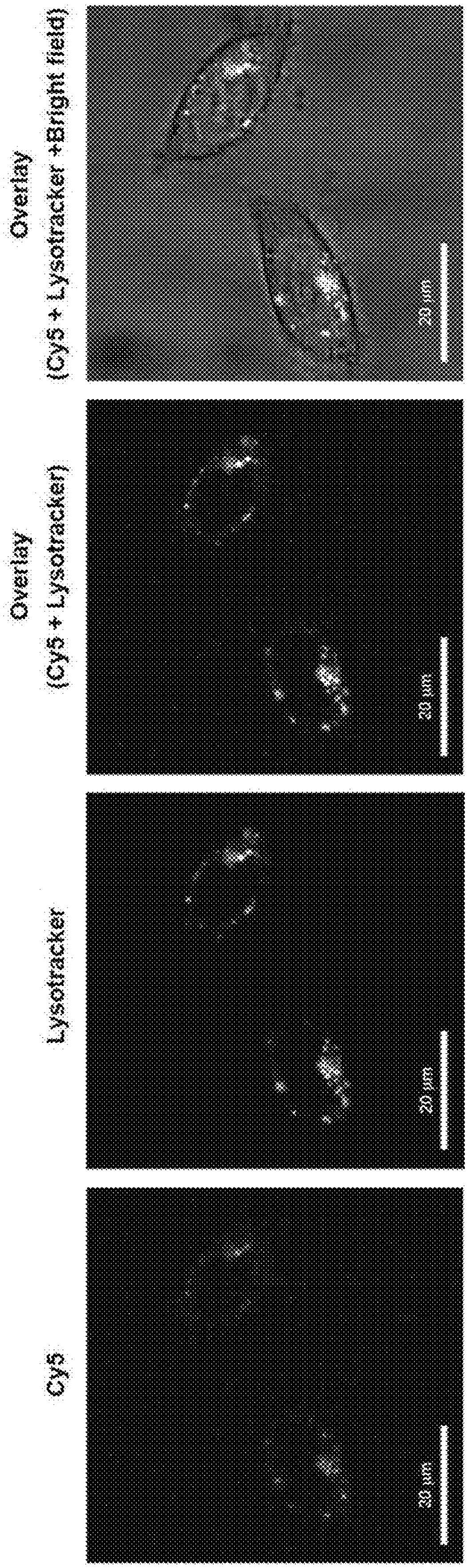
FIG. 25 and FIG. 26 show CLSM (confocal laser scanning microscopy) images obtained after administering a SAB-$g_3$/mRNA nanostructure (SAB nanotube; charge ratio=0.125 or 0.25) to Hela cells. Cy5 (mRNA) is shown in red color, LysoTracker in green, and colocalization in yellow.
Figure 26:
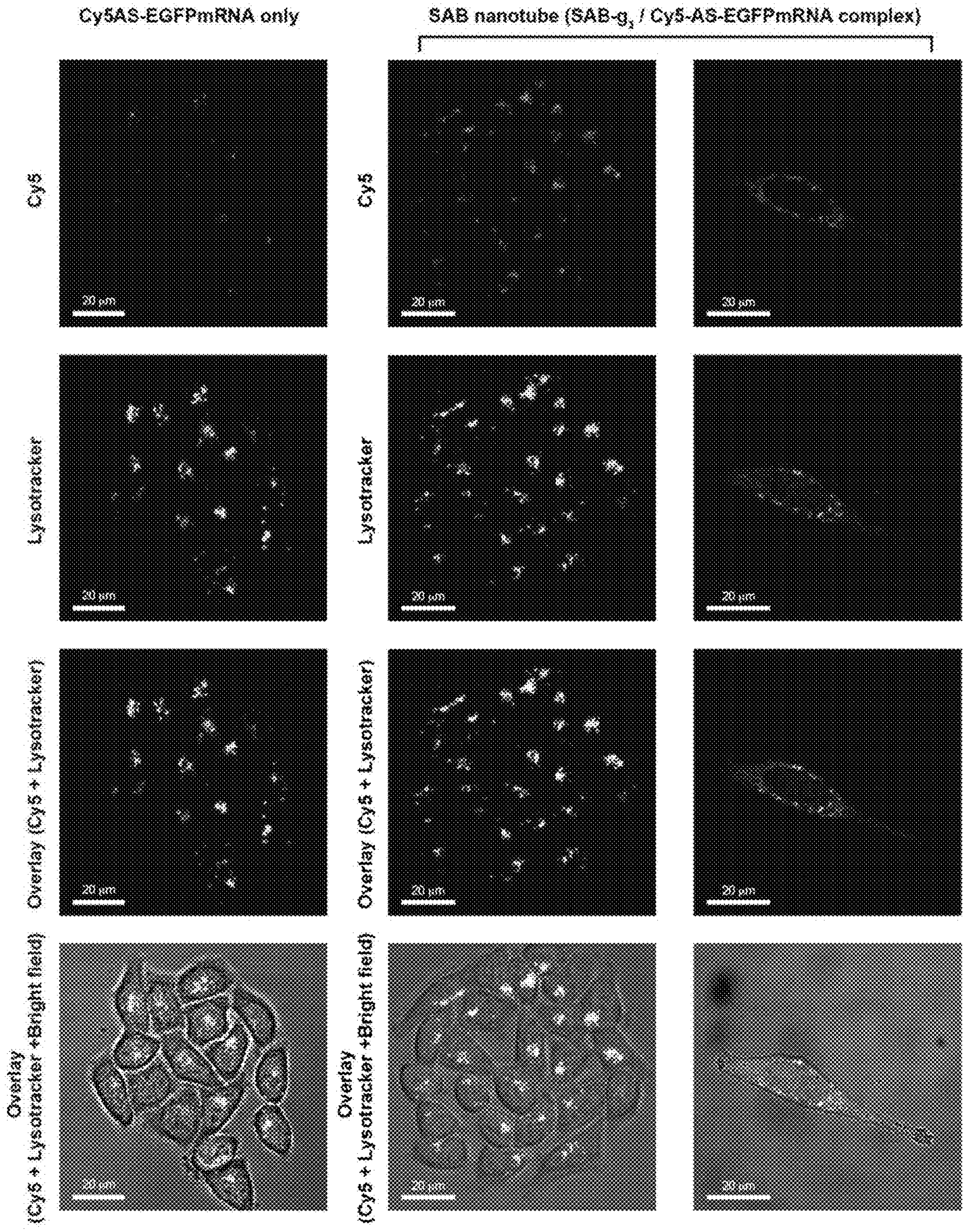

FIG. 25 and FIG. 26 show the CLSM (confocal laser scanning microscopy) images obtained after administering the SAB-$g_3$/mRNA nanostructure (SAB nanotube; charge ratio=0.125 or 0.25) to Hela cells. Cy5 (mRNA) is shown in red color, LysoTracker in green, and colocalization in yellow.

From FIG. 25 and FIG. 26, it can be seen that the SAB-$g_3$/mRNA nanostructure (SAB nanotube) can be effectively delivered into the cytoplasm of HeLa cells. That is to say, the SAB-$g_3$/mRNA nanostructure (SAB nanotube) is very useful as an mRNA carrier since it can stably deliver the mRNA to the cytoplasm such that translation can occur easily.

In addition, the location of the SAB-$g_3$/mRNA nanostructure (SAB nanotube) corresponded in most cases to those of the LysoTracker-labeled acidic cell organelles. That is to say, it can be seen that the SAB-$g_3$/mRNA nanostructure (SAB nanotube) effectively delivers the nucleic acid material into the cytoplasm of cells via acidic cell organelles such as lysosomes.

Test Example 9. Intracellular Delivery Efficiency of Nanostructure of Peptide-Molecule Conjugate (SAB) and mRNA 9-1. Preparation of Nanostructure of Peptide-Molecule Conjugate (SAB) and mRNA (SAB-$g_3$/mRNA)

The intracellular delivery effect of the nanostructure of the peptide-molecule conjugate (SAB) and mRNA was investigated. Control groups were treated with nothing (mock) or only with Cy5-AS-EGFP mRNA (mRNA only).

As the EGFP mRNA, Cy5-labeled EGFP mRNA (hereinafter, referred to as 'Cy5-AS-EGFP mRNA') hybridized with a Cy5-labeled oligonucleotide probe was used. Specifically, the Cy5-AS-EGFP mRNA was prepared using a Cy5-labeled antisense oligonucleotide (Cy5-AS: /5Cy5/ GCG AGC TGC ACG CTG CCG TC) (SEQ ID NO: 18) and EGFP mRNA. First, after mixing Cy5-AS and EGFP mRNA of the same volumes and concentrations, the Cy5-AS-EGFP mRNA was prepared by heating the mixture for 3 minutes at 94° C. and slowly cooling at room temperature.

The peptide-molecule conjugate prepared in Example 6 (SAB-$g_3$) and the Cy5-AS-EGFP mRNA were mixed in distilled water at a charge ratio (+/− ratio) of 0.125 and 0.25, respectively. After heating the mixture for 10 minutes at 70° C., it was snap-cooled on ice. After incubation at room temperature for 1 hour, the sample immersed in deionized water was diluted 5-fold with Opti-MEM to prepare the SAB-$g_3$/mRNA nanostructure. Immediately before the mixing, the peptide-molecule conjugate prepared in Example 6 (SAB) was sonicated for 5 minutes.

9-2. Transfection of mRNA and Protein Expression

HeLa (ATCC CCL-2) cells were used. The Hela cells were cultured in DMEM (Dulbecco's modified Eagle's medium) containing 10% (v/v) FBS and penicillin-streptomycin.

After seeding $1\times10^4$ HeLa cells in each well of a 96-well cell culture plate (SPL, Pocheon, Korea) and culturing for 24 hours, the sample (200 μL) or the control substance (200 μL) was added to each well together with 100 μM chloroquine as an endosomal escape promoter and the cells were cultured for 4 hours. The amount of mRNA added to each well was 1 μg. The 96-well cell culture plate (SPL, Pocheon, Korea) and a Nunc™ Lab-Tek™ II chambered coverglass (Thermo Scientific, Waltham, USA) were used. After washing the cells with DPBS and culturing further for 48 hours after adding a fresh medium, they were analyzed by flow cytometry. The procedure of the flow cytometry is described in detail above in the Experimental methods section.

9-3. Analysis Result

Figure 27:
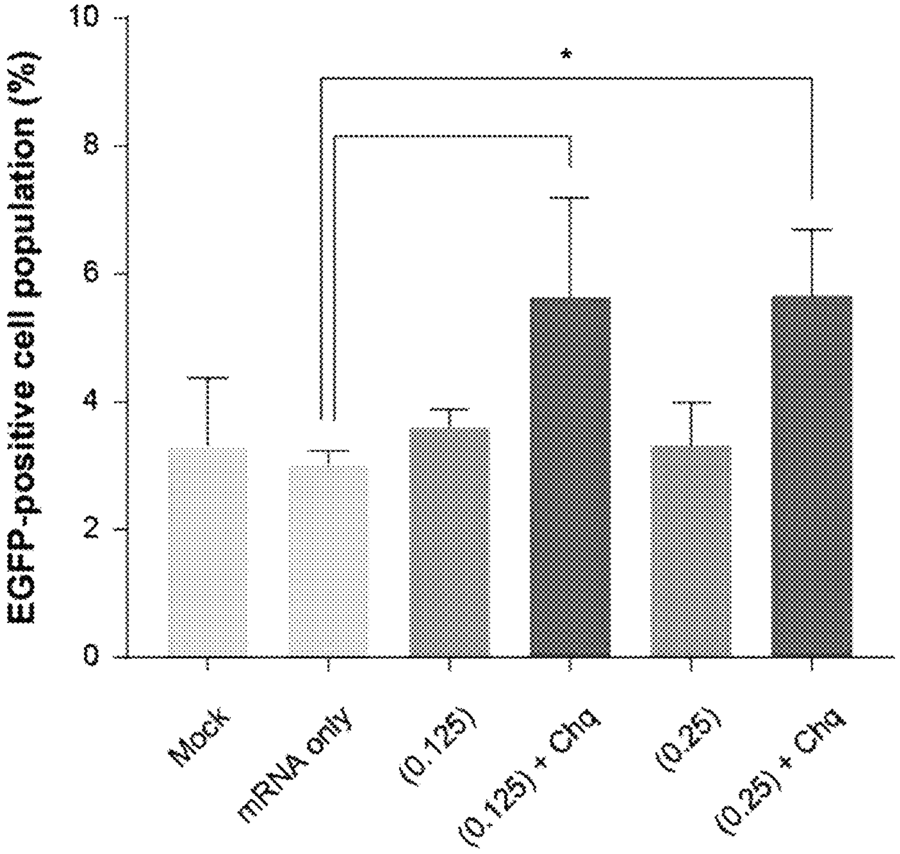
FIG. 27 shows a result of treating HeLa cells treated with chloroquine, which is an autophagy inhibitor, with an SAB-$g_3$/mRNA nanostructure (SAB nanotube, 0.125 or 0.25) and then quantifying the proportion of the cells expressing the EGFP gene by flow cytometry. Chq indicates chloroquine (100 μM). Mean±SD (n=3). *P<0.05.

FIG. 27 shows a result of treating Hela cells treated with chloroquine, which is an endosomal escape promoter, with the SAB-$g_3$/mRNA nanostructure (SAB nanotube, 0.125 or 0.25) and then quantifying the proportion (%) of the cells expressing the EGFP gene by flow cytometry. Chq indicates chloroquine (100 μM). Mean±SD (n=3). *$P<0.05$.

As seen from FIG. 27, significant expression of the EGFP gene was not observed in the cells treated only with the SAB-$g_3$/mRNA nanostructure (0.125, 0.25) without chloroquine.

In contrast, significant expression of the EGFP gene was observed in the cells treated with the SAB-$g_3$/mRNA nanostructure (0.125, 0.25) and chloroquine. That is to say, it was confirmed that the nanostructure of the peptide-molecule conjugate according to the present disclosure (SAB) and mRNA is easily introduced into cells by endocytosis and enables easy delivery of nucleic acids into the cells via lysosomes.

Test Example 10. Analysis of Chemical, Biological and Thermodynamic Stability of Nanostructure of Peptide-Molecule Conjugate (SAB) and mRNA It was investigated whether the nanostructure of the peptide-molecule conjugate (SAB) and mRNA protects the mRNA when it is exposed to various external environments.

10-1. Preparation of Nanostructure of Peptide-Molecule Conjugate (SAB) and mRNA

The intracellular delivery effect of the nanostructure of the peptide-molecule conjugate (SAB) and mRNA was evaluated. A control group was treated with the EGFP mRNA alone (mRNA).

As the EGFP mRNA, Cy5-labeled EGFP mRNA (hereinafter, referred to as 'Cy5-AS-EGFP mRNA') hybridized with a Cy5-labeled oligonucleotide probe was used. Specifically, the Cy5-AS-EGFP mRNA was prepared using a Cy5-labeled antisense oligonucleotide (Cy5-AS: /5Cy5/ GCG AGC TGC ACG CTG CCG TC) (SEQ ID NO: 18) and EGFP mRNA. First, after mixing Cy5-AS and EGFP mRNA of the same volumes and concentrations, the Cy5-AS-EGFP mRNA was prepared by heating the mixture for 3 minutes at 94° C. and slowly cooling at room temperature.

The peptide-molecule conjugate prepared in Example 6 (SAB-$g_3$) and the Cy5-AS-EGFP mRNA were mixed in distilled water at a charge ratio (+/− ratio) of 0.125 and 0.25, respectively. After heating the mixture for 10 minutes at 70° C., it was snap-cooled on ice. After incubation at room temperature for 1 hour, the sample immersed in deionized water was diluted 5-fold with Opti-MEM to prepare the SAB-$g_3$/mRNA nanostructure. Immediately before the mixing, the peptide-molecule conjugate prepared in Example 6 (SAB) was sonicated for 5 minutes.

10-2. Evaluation of Stability (Thermodynamic Stability) Against Urea Denaturation After adding the SAB-$g_3$/mRNA nanostructure (0.25, 1.0) to 0 M, 0.25 M, 0.5 M, 1 M, 2 M, 3 M, 4 M, 5 M, 6 M, 7 M, 8 M or 9 M urea, EMSA (electrophoretic mobility shift assay with mRNA) was conducted after treating for 10 minutes at room temperature.

The fraction of the nanostructure existing as unfolded state due to the unfolding of protein structure after treatment with the urea was calculated as $F_{unf}$. The $F_{unf}$ determined by quantifying the content of the released mRNA. K was calculated as the half-dissociation constant.

10-3. Evaluation of Stability Against Biological Hazards

After adding the SAB-$g_3$/mRNA nanostructure (charge ratio=0, 0.63, 0.125, 0.25, 0.5, 1, 2 or 4) to 50 μU RNase A, EMSA (electrophoretic mobility shift assay with mRNA) was conducted after treating for 20 minutes at 37° C. 10-4. Evaluation of stability against chemical hazards After preparing an aqueous solution by adding the SAB-$g_3$/mRNA nanostructure (charge ratio=0.25) to distilled water and storing for a long time (13 weeks) at 4° C., the stability of the SAB-$g_3$/mRNA nanostructure was evaluated by conducting EMSA (electrophoretic mobility shift assay with mRNA). The analysis was conducted by recovering the SAB-$g_3$/mRNA nanostructure at different times and treating with 1% SDS.

Figure 28:
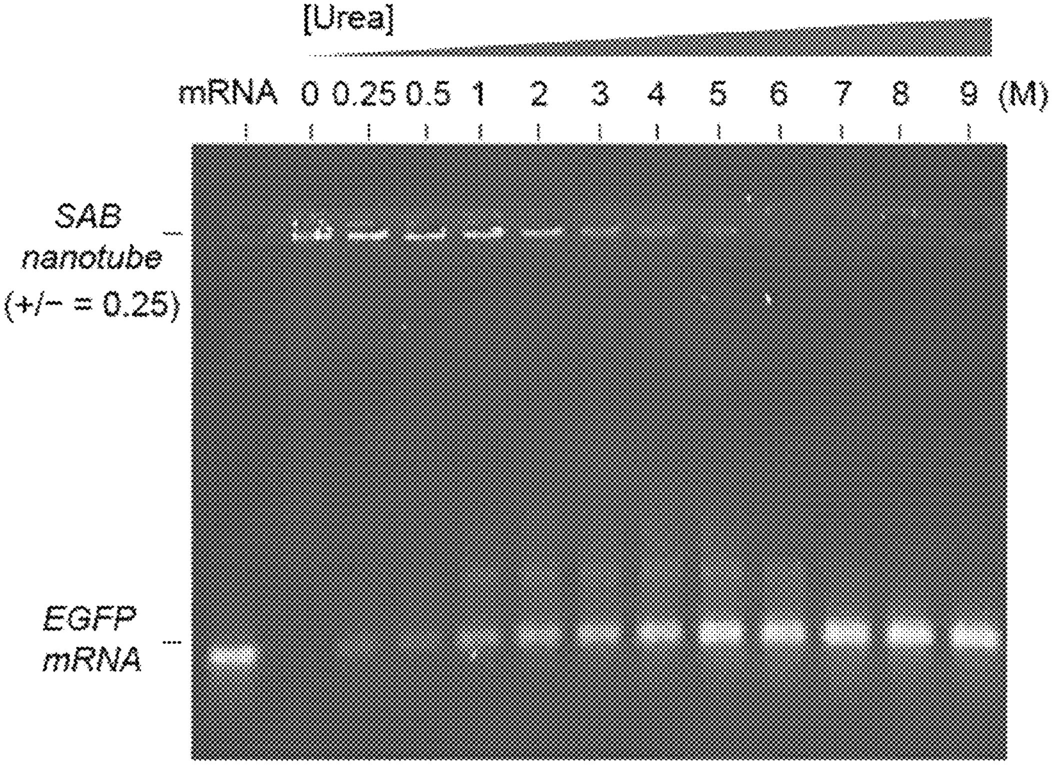
FIG. 28 shows an EMSA result of analyzing urea denaturation stability for an SAB-$g_3$/mRNA nanostructure (charge ratio=0.25).
Figure 29:
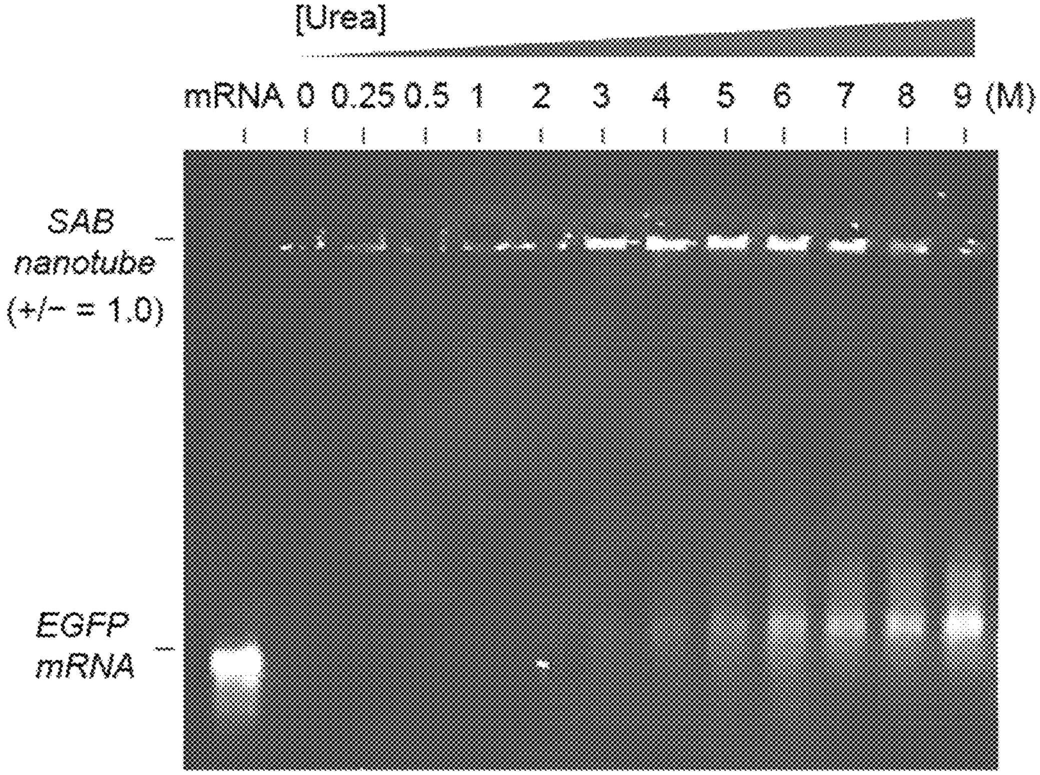
FIG. 29 shows an EMSA result of analyzing urea denaturation stability for an SAB-$g_3$/mRNA nanostructure (charge ratio=1.0).
Figure 30:
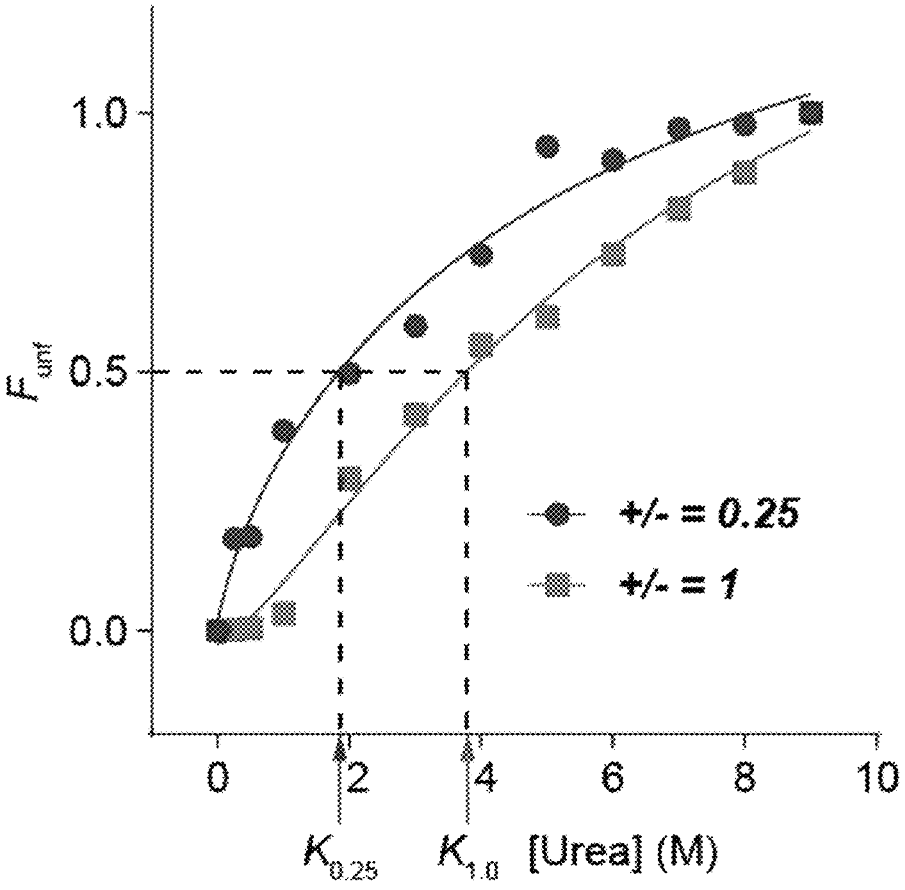
FIG. 30 shows the fraction of unfolded nanostructure ($F_{unf}$) in an SAB-$g_3$/mRNA nanostructure calculated from FIG. 28 and FIG. 29.

FIG. 28 shows the EMSA result of analyzing the urea denaturation stability of the SAB-$g_3$/mRNA nanostructure (charge ratio=0.25). FIG. 29 shows the EMSA result of analyzing the urea denaturation stability of the SAB-$g_3$/mRNA nanostructure (charge ratio=1.0). FIG. 30 shows the fraction of the unfolded nanostructure ($F_{unf}$) of the SAB-$g_3$/mRNA nanostructure calculated from FIG. 28 and FIG. 29.

From FIG. 28 and FIG. 29, it can be seen that the SAB-$g_3$/mRNA nanostructure has superior thermodynamic stability. Since the peptide-molecule conjugate (SAB) is a protein/peptide-like molecule and the SAB-$g_3$/mRNA nanostructure prepared therefrom is a self-assembled protein-protein, their thermodynamic stability was evaluated through urea denaturation. As a result, it was confirmed that the SAB-$g_3$/mRNA nanostructure according to the present disclosure is dissociated and releases mRNA at urea concentrations of 1 M and 5 M, indicating that it has very superior thermodynamic stability.

In particular, it was confirmed that the SAB-$g_3$/mRNA nanostructure has very high thermodynamic stability when the charge ratio of the peptide-molecule conjugate (SAB) and mRNA is 1.0, and it maintains its structure even at the urea concentration of 8 M.

For tobacco mosaic virus (TMV), dissociation occurred at the urea concentration of 0.2-1.8 M. Because the SAB-$g_3$/mRNA nanostructure exhibits significantly superior thermodynamic stability as compared to the TMV nanotube, it can be usefully used as a carrier for storing a nucleic acid material and delivering it into cells.

Figure 31:
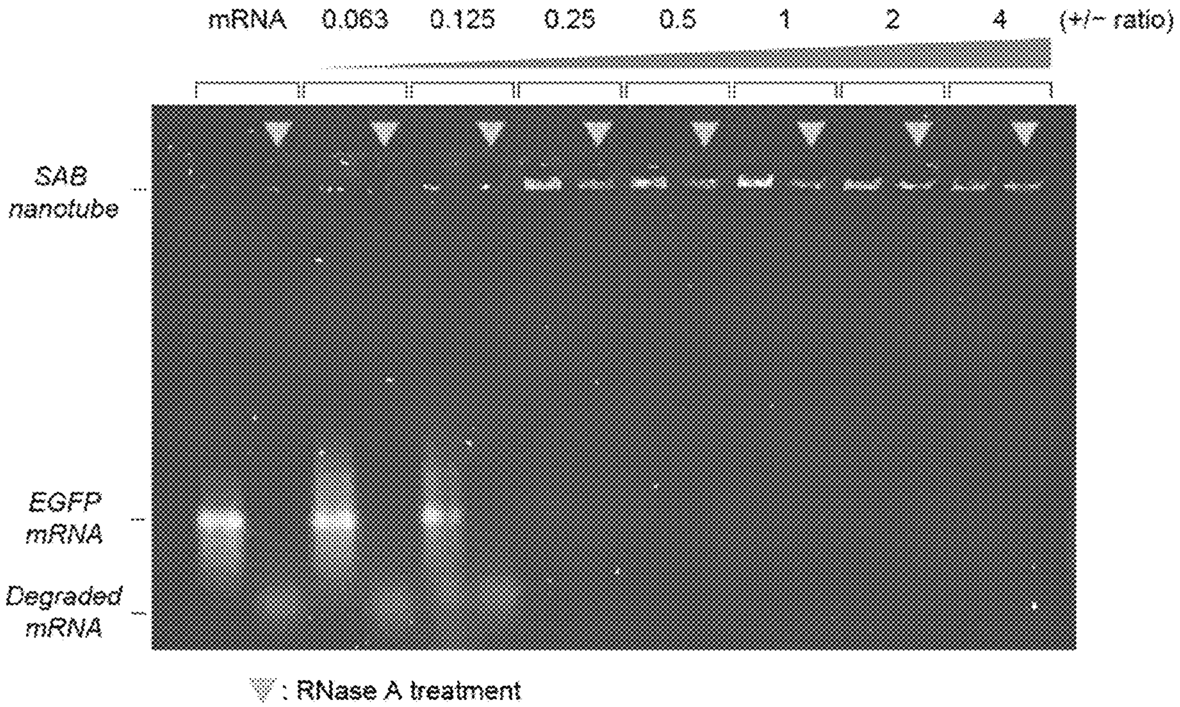
FIG. 31 shows an EMSA result of analyzing the biological stability of an SAB-$g_3$/mRNA nanostructure.
Figure 32:
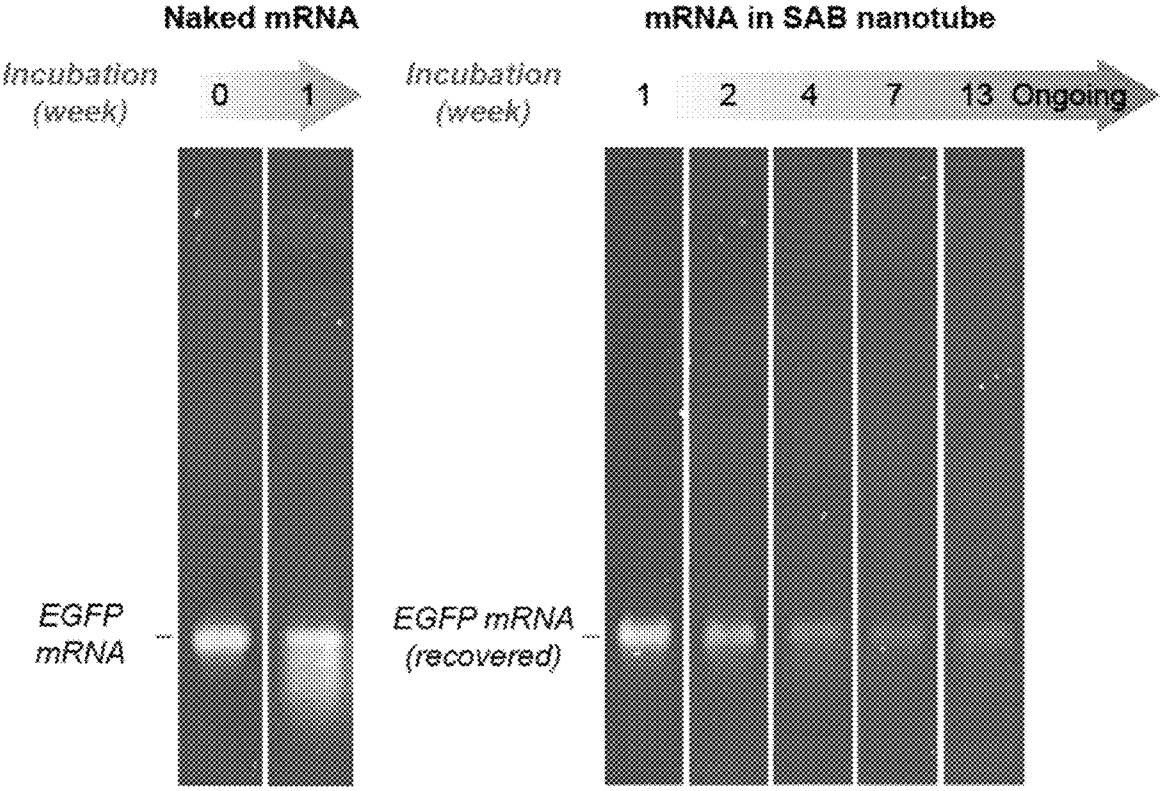
FIG. 32 shows an EMSA result of analyzing the chemical stability of an SAB-$g_3$/mRNA nanostructure.

FIG. 31 shows an EMSA result of analyzing the biological stability of the SAB-$g_3$/mRNA nanostructure, and FIG. 32 shows an EMSA result of analyzing the chemical stability of the SAB-$g_3$/mRNA nanostructure.

As a result of investigating whether the SAB-$g_3$/mRNA nanostructure can protect mRNA from RNase (ribonuclease), it was confirmed that the mRNA coated by the peptide-molecule conjugate (SAB) at a charge ratio of 0.25 or higher was very safe against the attack of RNase A as shown in FIG. 31.

In addition, the stability of the SAB-$g_3$/mRNA nanostructure when stored for a long time under biologically harsh conditions was analyzed. As shown in FIG. 32, the SAB-$g_3$/mRNA nanostructure maintained its structure even after storage in solution for 13 weeks or longer. In contrast, when mRNA was stored alone in solution (naked mRNA), it was degraded within 1 week even at the low temperature of 4° C.

Test Example 11. Preparation and Analysis of Nanostructure of Peptide-Molecule Conjugate and Gene with Nucleobase Bound In the peptide-molecule conjugates of Examples 10-24, a nucleobase is bound to the peptide constituting the gene-binding region (b). Aqueous solutions were prepared by dispersing the peptide-molecule conjugates prepared in Examples 10-24 in distilled water at different concentrations. Specifically, after preparing aqueous solutions by dispersing the peptide-molecule conjugates of Examples 10-24 in distilled water at different concentrations and sonicating for 5 minutes, an ssDNA solution (5 μL) was added and mixed immediately. The ssDNA was prepared PAGE Ultramer® DNA Oligo (40 mer, 100 mer or 200 mer) by IDT Korea.

The concentration of the ssDNA was fixed and the concentration of the peptide-molecule conjugate aqueous solution was varied based on the nucleobase ratio. Specifically, because the peptide-molecule conjugate has one or two nucleobases per head domain and the ssDNA has 20, 50 or 100 nucleobase pairs, the nucleobase ratio was calculated based thereon.

After incubating the mixture of the peptide-molecule conjugate and ssDNA overnight, it was analyzed by EMSA. In the EMSA result, the electrophoretic mobility means that there is hydrogen bonding interaction between the peptide-molecule conjugate and the ssDNA. If the electrophoretic mobility was delayed relatively, it means that the hydrogen bonding interaction between the peptide-molecule conjugate and the ssDNA has increased. In addition, if the mobility was delayed completely, it means that the nanostructure was formed through self-assembly of the ssDNA and the peptide-molecule conjugate.

Figure 33A:
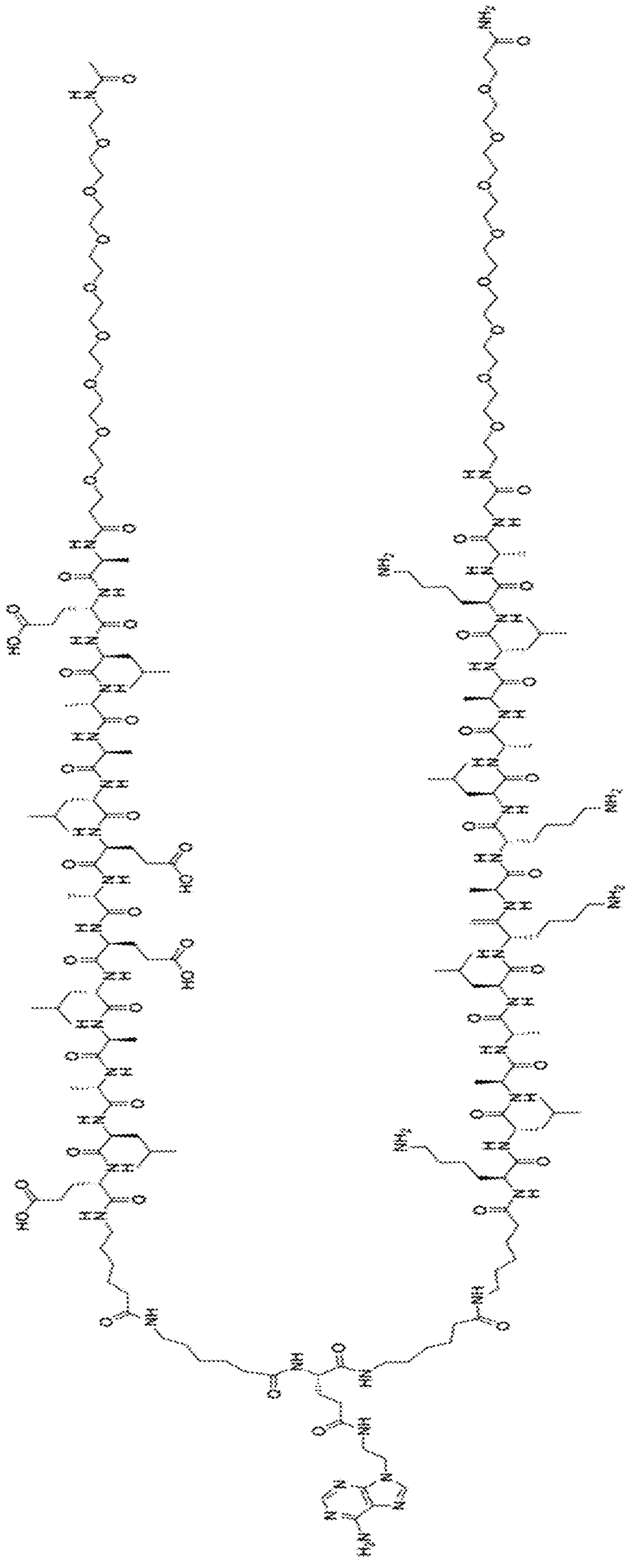
FIG. 33A shows the structure of a peptide-molecule conjugate of Example 10 ($PEG8_2$-A-U0)
Figure 33B:
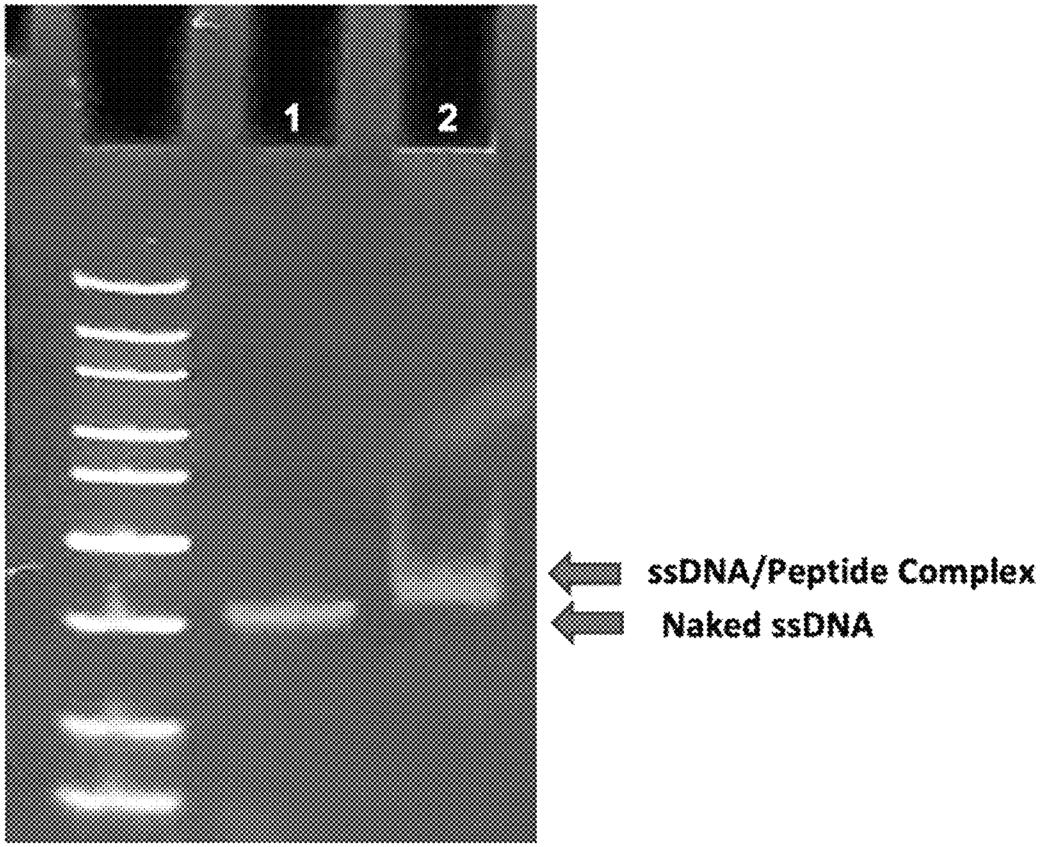
FIG. 33B shows an EMSA result for a nanostructure prepared by mixing peptide-molecule conjugate of Example 10 ($PEG8_2$-A-U0) with ssDNA PolyT40 at a nucleobase ratio of 640.

FIG. 33A shows the structure of the peptide-molecule conjugate of Example 10 ($PEG8_2$-A-U0), and FIG. 33B shows an EMSA result for the nanostructure prepared by mixing peptide-molecule conjugate of Example 10 ($PEG8_2$-A-U0) with ssDNA PolyT40 at a nucleobase ratio of 640. In FIG. 33B, the lane 1 indicates a naked DNA, and the lane 2 indicates an ssDNA/peptide complex.

A 16 M aqueous solution was prepared by dispersing the peptide-molecule conjugate of Example 10 ($PEG8_2$-A-U0) in distilled water. A nanostructure was prepared by mixing the peptide-molecule conjugate of Example 10 ($PEG8_2$-A-U0) and ssDNA PolyT40 (5 μL) at a nucleobase ratio of 640. FIG. 33B shows the EMSA result for the nanostructure. From FIG. 33, it can be seen that electrophoretic mobility is delayed slightly for the mixture of the peptide-molecule conjugate ($PEG8_2$-A-U0) and the ssDNA PolyT40. That is to say, it can be seen that the peptide-molecule conjugate ($PEG8_2$-A-U0) and the ssDNA PolyT40 successfully forms a nanostructure through hydrogen bonding interaction.

Figure 34A:
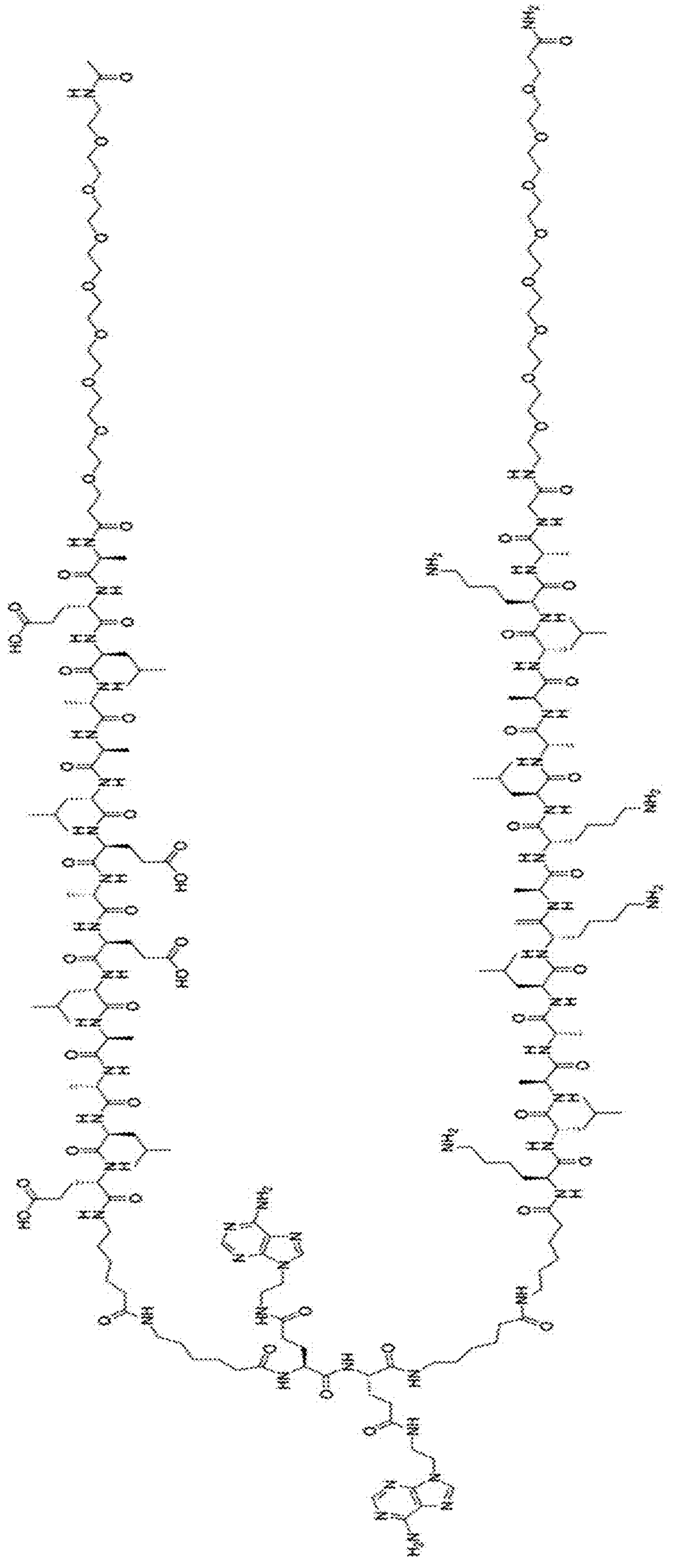
FIG. 34A shows the structure of a peptide-molecule conjugate of Example 11 ($PEG8_2$-AA-U0)
Figure 34B:
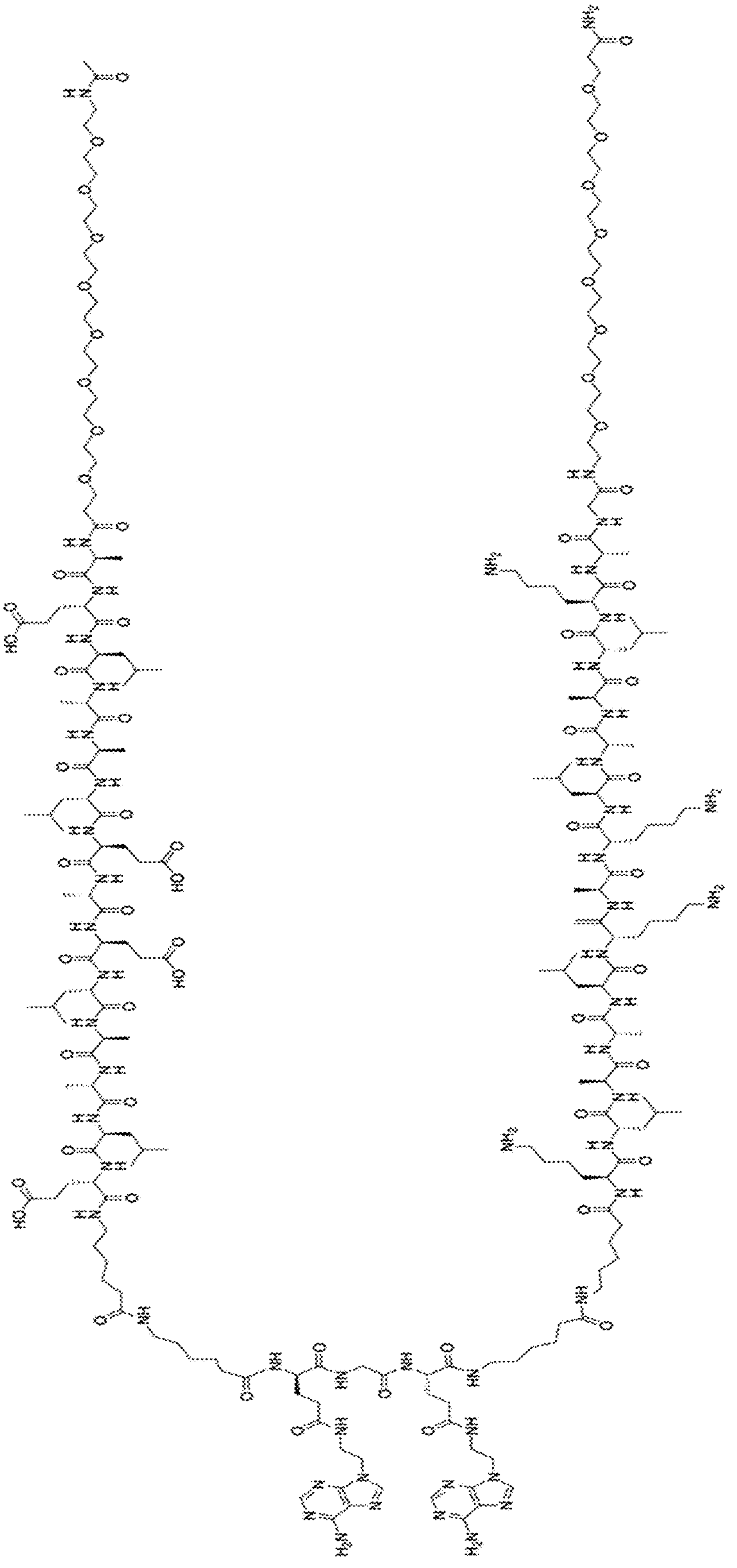
FIG. 34B shows the structure of a peptide-molecule conjugate of Example 12 ($PEG8_2$-AGlyA-U0)
Figure 34C:
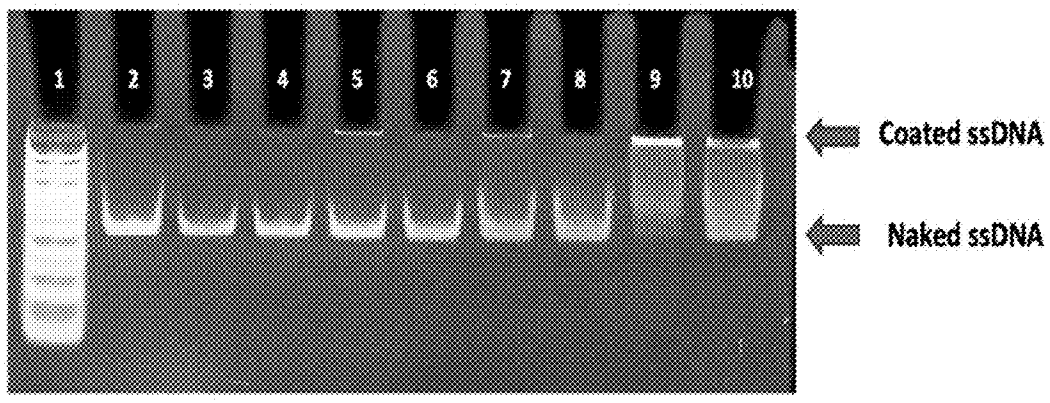
FIG. 34C shows an EMSA result for nanostructures prepared by mixing peptide-molecule conjugates of Examples 11 and 12 ($PEG8_2$-AA-U0 and $PEG8_2$-AGlyA-U0) and ssDNA PolyT40 at different nucleobase ratios.

FIG. 34A shows the structure of the peptide-molecule conjugate of Example 11 ($PEG8_2$-AA-U0), FIG. 34B shows the structure of the peptide-molecule conjugate of Example 12 ($PEG8_2$-AGlyA-U0), and FIG. 34C shows an EMSA result for nanostructures prepared by mixing the peptide-molecule conjugates of Examples 11 and 12 ($PEG8_2$-AA-U0 and $PEG8_2$-AGlyA-U0) and ssDNA PolyT40 at different nucleobase ratios.

1 M, 2 M, 4 M and 16 M aqueous solutions were prepared by dispersing the peptide-molecule conjugates of Examples 11 and 12 ($PEG8_2$-AA-U0, $PEG8_2$-AGlyA-U0) in distilled water, respectively. The peptide-molecule conjugates of Examples 11 and 12 ($PEG8_2$-A-U0, $PEG8_2$-AGlyA-U0) and the ssDNA PolyT40 (5 μL) were mixed at nucleobase ratios of 80, 160, 320 and 1280, respectively, and were analyzed by EMSA.

As shown in FIG. 34, electrophoretic mobility was delayed relatively more when the nucleobase ratio of the peptide-molecule conjugate of Example 11 ($PEG8_2$-AA-U0) and the ssDNA PolyT40 was 1280:1. That is to say, it can be seen that hydrogen bonding interaction occurs more between the peptide-molecule conjugate of Example 11 ($PEG8_2$-AA-U0) and the ssDNA as compared to the peptide-molecule conjugate of Example 12 ($PEG8_2$-AGlyA-U0).

Figure 35A:
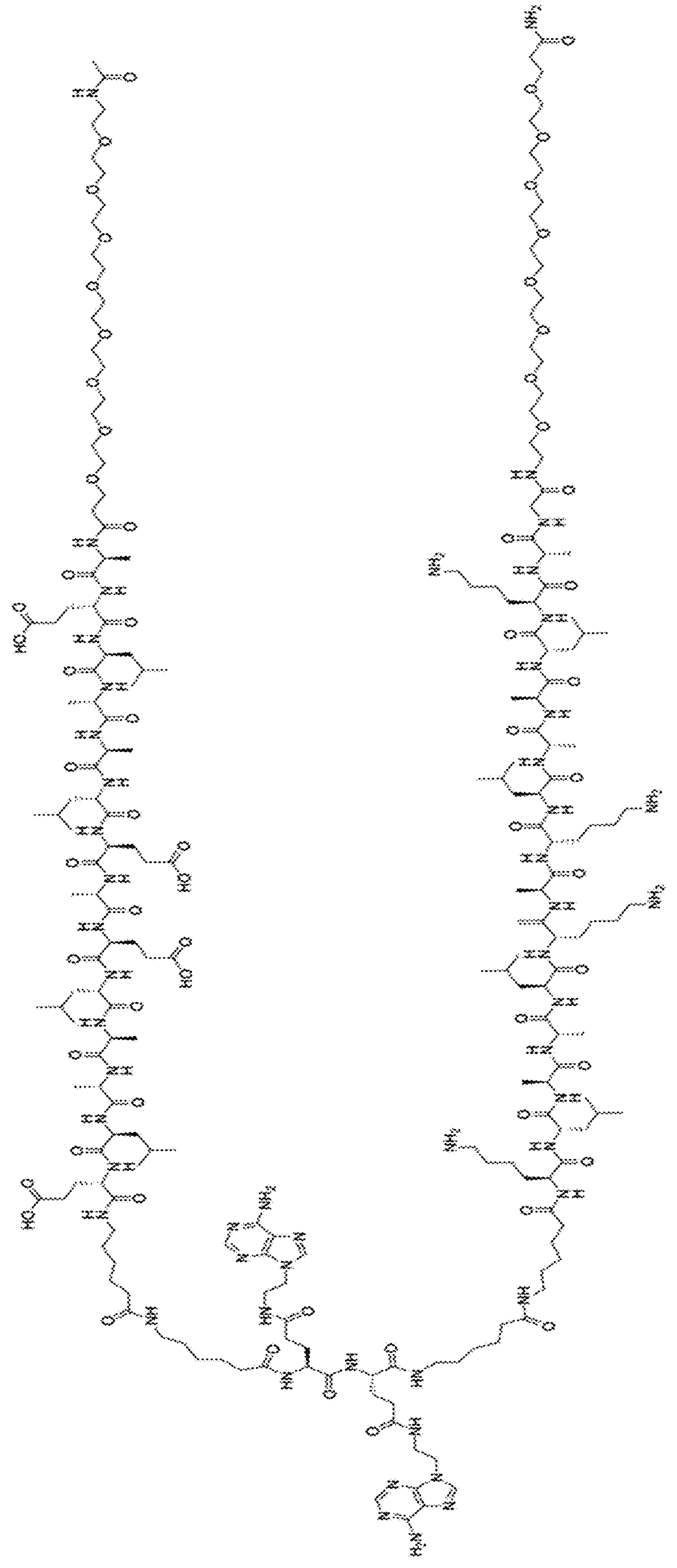
FIG. 35A shows the structure of a peptide-molecule conjugate of Example 11 ($PEG8_2$-AA-U0)
Figure 35B:
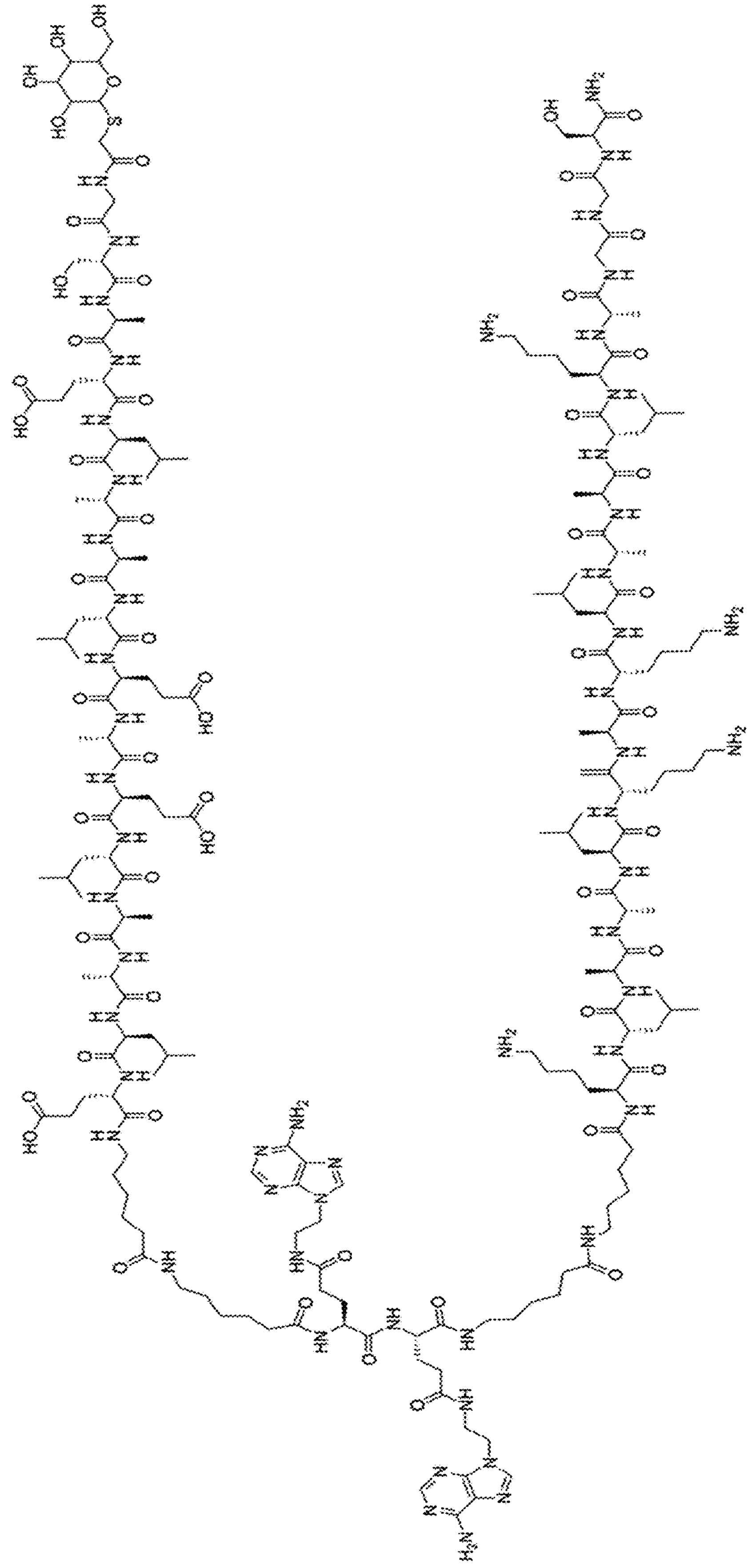
FIG. 35B shows the structure of a peptide-molecule conjugate of Example 13 ($Glc_1$-AA-U0)
Figure 35C:
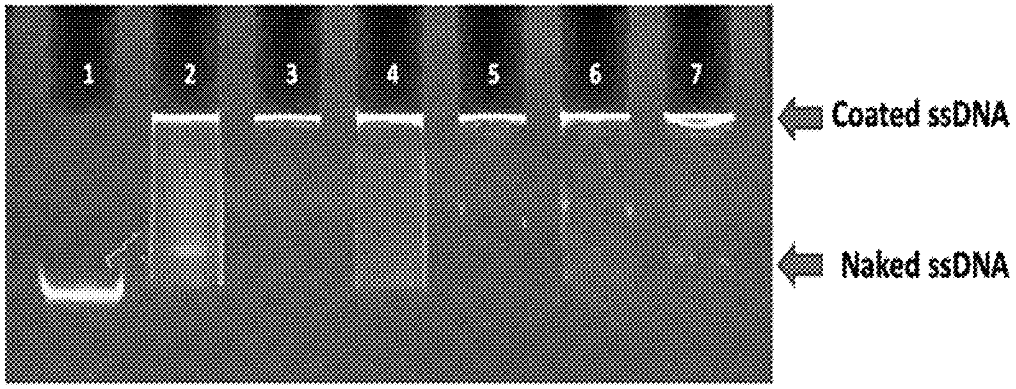
FIG. 35C shows an EMSA result for nanostructures prepared by mixing peptide-molecule conjugates of Example 11 and 13 ($PEG8_2$-AA-U0 and $Glc_1$-AA-U0) and ssDNA PolyT100 at different nucleobase ratios.

FIG. 35A shows the structure of the peptide-molecule conjugate of Example 11 ($PEG8_2$-AA-U0), FIG. 35B shows the structure of the peptide-molecule conjugate of Example 13 ($Glc_1$-AA-U0), and FIG. 35C shows an EMSA result for the nanostructures prepared by mixing peptide-molecule conjugates of Example 11 and 13 ($PEG8_2$-AA-U0 and $Glc_1$-AA-U0) and ssDNA PolyT100 at different nucleobase ratios.

2500 μM, 3750 μM and 4375 μM aqueous solutions were prepared by dispersing the peptide-molecule conjugates of Examples 11 and 13 ($PEG8_2$-AA-U0, $Glc_1$-AA-U0) in distilled water, respectively. The peptide-molecule conjugates of Examples 11 and 13 ($PEG8_2$-AA-U0, $Glc_1$-AA-U0) were mixed with the ssDNA PolyT100 (5 μL) at nucleobase ratios of 80, 120 and 140 and then analyzed by EMSA.

As shown in FIG. 35, electrophoretic mobility was delayed completely when the peptide-molecule conjugate of Example 13 ($Glc_1$-AA-U0) was mixed with the ssDNA PolyT100 at a nucleobase ratio of 80:1. This means that the $Glc_1$-AA-U0/ssDNA PolyT100 nanostructure was formed.

Figure 36A:
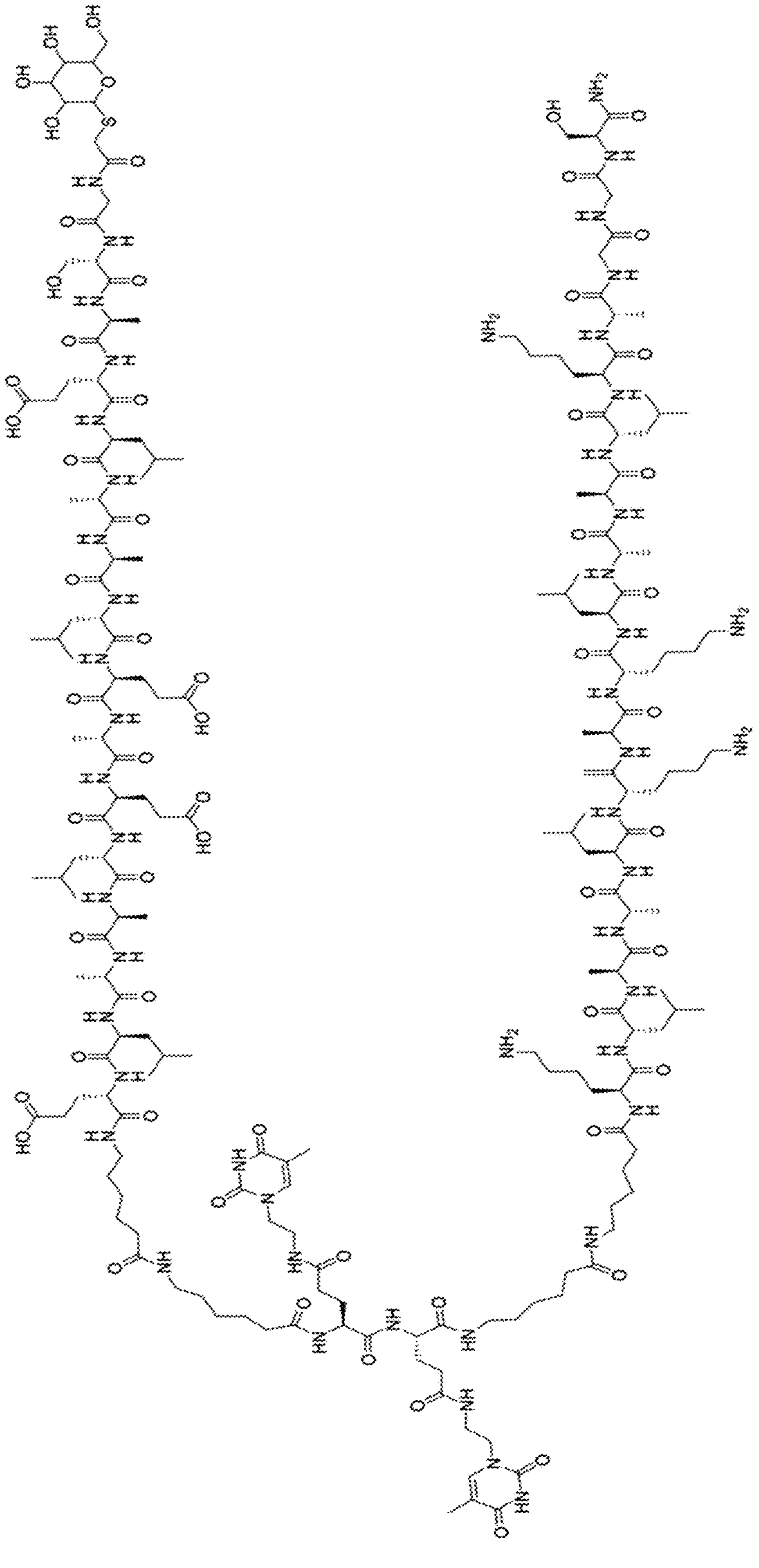
FIG. 36A shows the structure of a peptide-molecule conjugate of Example 14 ($Glc_1$-TT-U0)
Figure 36B:
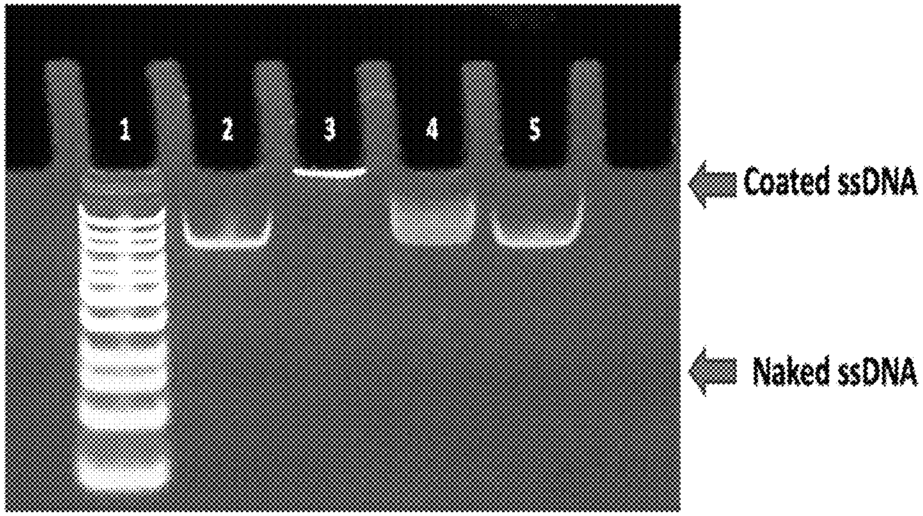
FIG. 36B shows an EMSA result for nanostructures prepared by mixing peptide-molecule conjugates of Examples 13 and 14 ($Glc_1$-AA-U0 and $Glc_1$-TT-U0) and ssDNA PolyT100 at a nucleobase ratio of 80.

FIG. 36A shows the structure of the peptide-molecule conjugate of Example 14 ($Glc_1$-TT-U0), and FIG. 36B shows an EMSA result for nanostructures prepared by mixing the peptide-molecule conjugates of Examples 13 and 14 ($Glc_1$-AA-U0 and $Glc_1$-TT-U0) and the ssDNA PolyT100 at a nucleobase ratio of 80.

2500 μM aqueous solutions were prepared by dispersing the peptide-molecule conjugates of Examples 13 and 14 ($Glc_1$-AA-U0, $Glc_1$-TT-U0) in distilled water. After preparing mixtures by mixing the peptide-molecule conjugates of Examples 13 and 14 ($Glc_1$-AA-U0, $Glc_1$-TT-U0) and the ssDNA PolyT100 (5 μL) at a nucleobase ratio 80, they were analyzed by EMSA.

As shown in FIG. 36, electrophoretic mobility was delayed completely for the peptide-molecule conjugate of Example 13 ($Glc_1$-AA-U0) and the ssDNA PolyT100, and no electrophoretic mobility was observed for the mixture of the peptide-molecule conjugate of Example 14 ($Glc_1$-TT-U0) and the ssDNA PolyT100. That is to say, it can be seen that hydrogen bonding interaction occurs selectively between the peptide-molecule conjugate of Example 13 ($Glc_1$-AA-U0) and the ssDNA PolyT100.

Figure 37A:
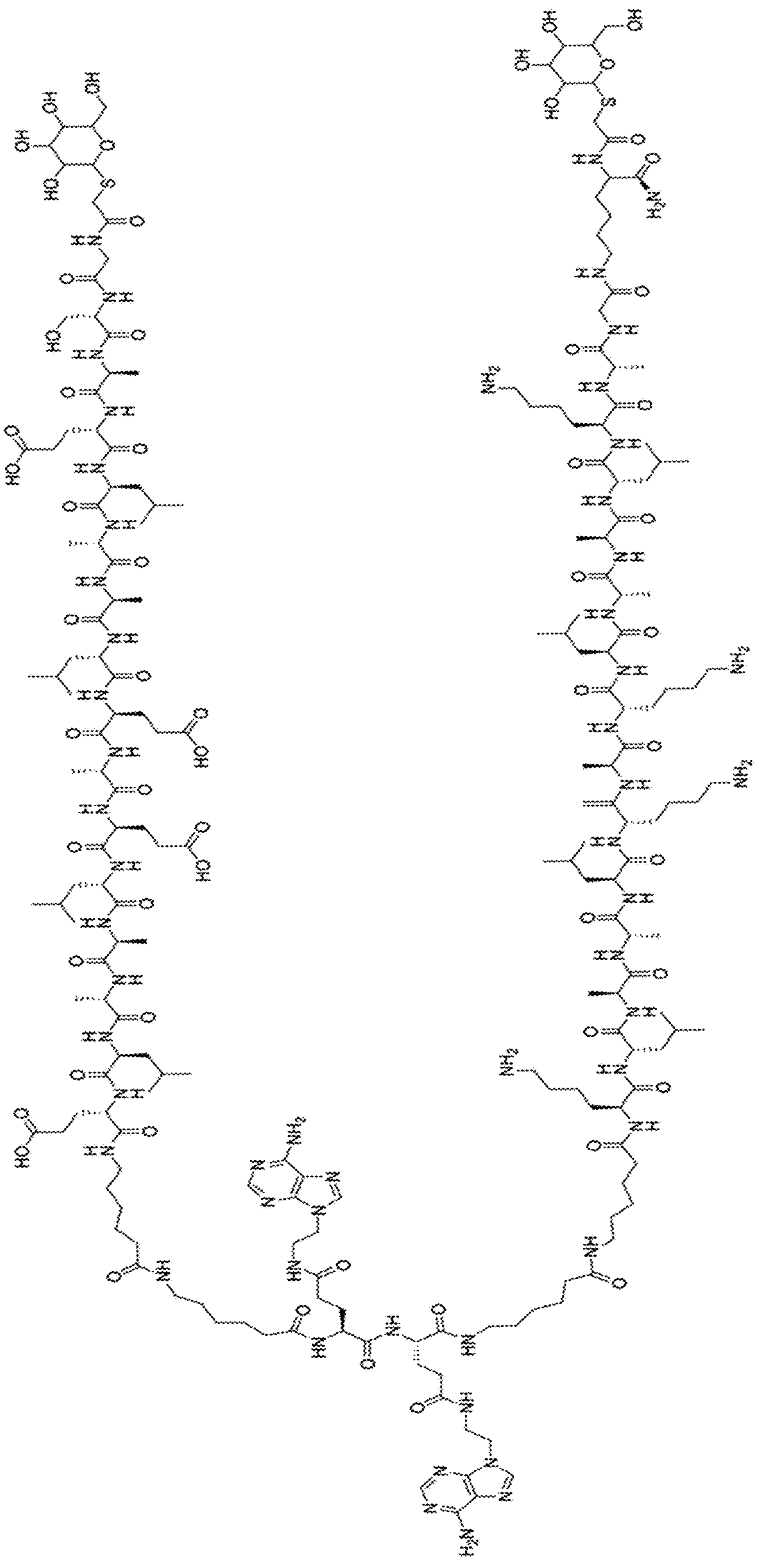
FIG. 37A shows the structure of a peptide-molecule conjugate of Example 15 ($Glc_2$-AA-U0)
Figure 37B:
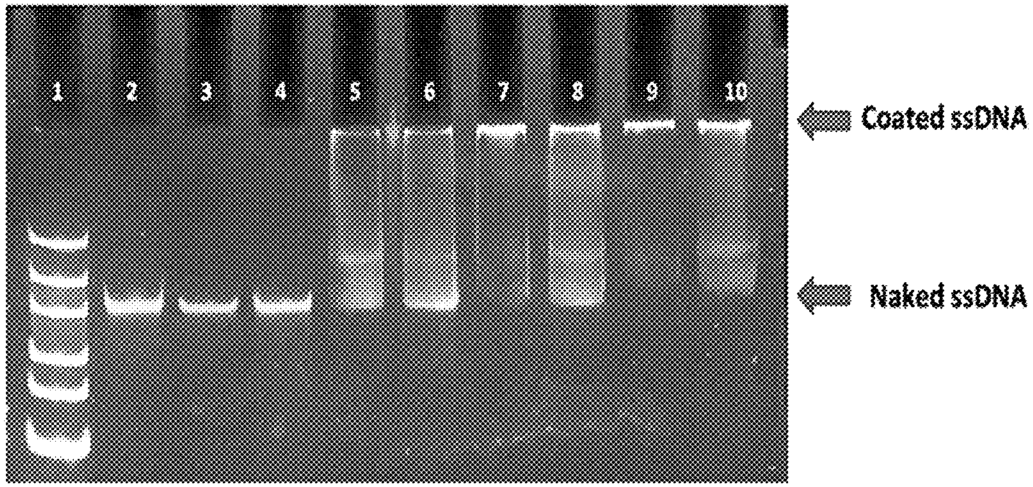
FIG. 37B shows an EMSA result for nanostructures prepared by mixing peptide-molecule conjugates of Examples 13 and 15 ($Glc_1$-AA-U0 and $Glc_2$-AA-U0) and ssDNA PolyT100 at different nucleobase ratios.

FIG. 37A shows the structure of the peptide-molecule conjugate of Example 15 ($Glc_2$-AA-U0), and FIG. 37B shows an EMSA result for nanostructures prepared by mixing the peptide-molecule conjugates of Examples 13 and 15 ($Glc_1$-AA-U0 and $Glc_2$-AA-U0) and ssDNA PolyT100 at different nucleobase ratios.

312.5 μM, 625 μM, 937.5 μM and 12500 μM aqueous solutions were prepared by dispersing the peptide-molecule conjugates of Examples 13 and 15 ($Glc_1$-AA-U0, $Glc_2$-AA-U0) in distilled water, respectively. After preparing mixtures by mixing the peptide-molecule conjugates of Examples 13 and 15 ($Glc_1$-AA-U0, $Glc_2$-AA-U0) with ssDNA PolyT100 (5 μL) at nucleobase ratios of 10, 20, 30 and 40, they were analyzed by EMSA.

As shown in FIG. 37, when the peptide-molecule conjugate of Example 13 ($Glc_1$-AA-U0) and the ssDNA PolyT100 were mixed at a nucleobase ratio of 40:1, electrophoretic mobility was delayed relatively more as compared to the peptide-molecule conjugate of Example 15 ($Glc_2$-AA-U0). Through this, it can be seen that hydrogen bonding interaction is stronger between the peptide-molecule conjugate of Example 13 ($Glc_1$-AA-U0) and the ssDNA PolyT100.

Figure 38A:
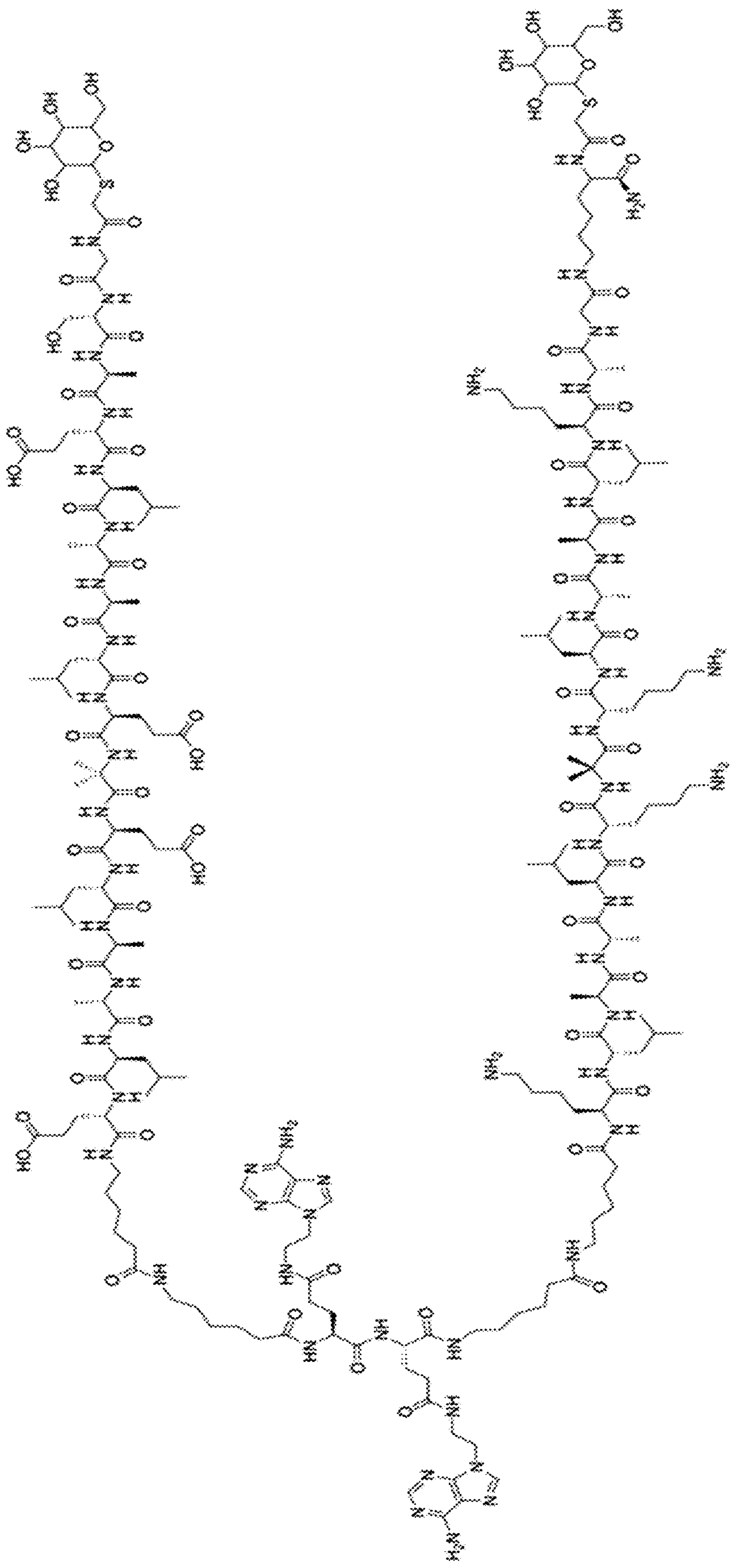
FIG. 38A shows the structure of a peptide-molecule conjugate of Example 16 ($Glc_2$-AA-U2)
Figure 38B:
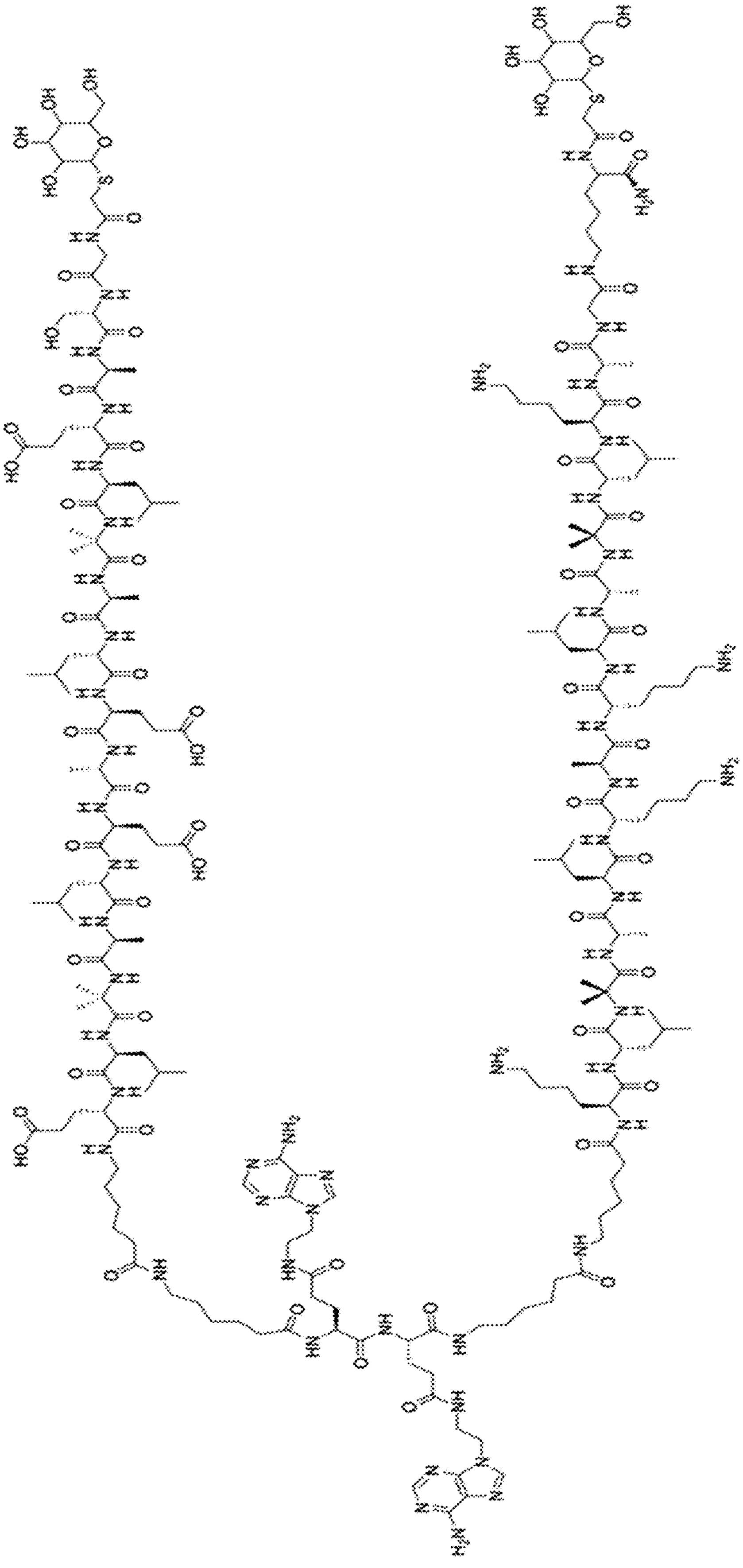
FIG. 38B shows the structure of a peptide-molecule conjugate of Example 17 ($Glc_2$-AA-U4)
Figure 38C:
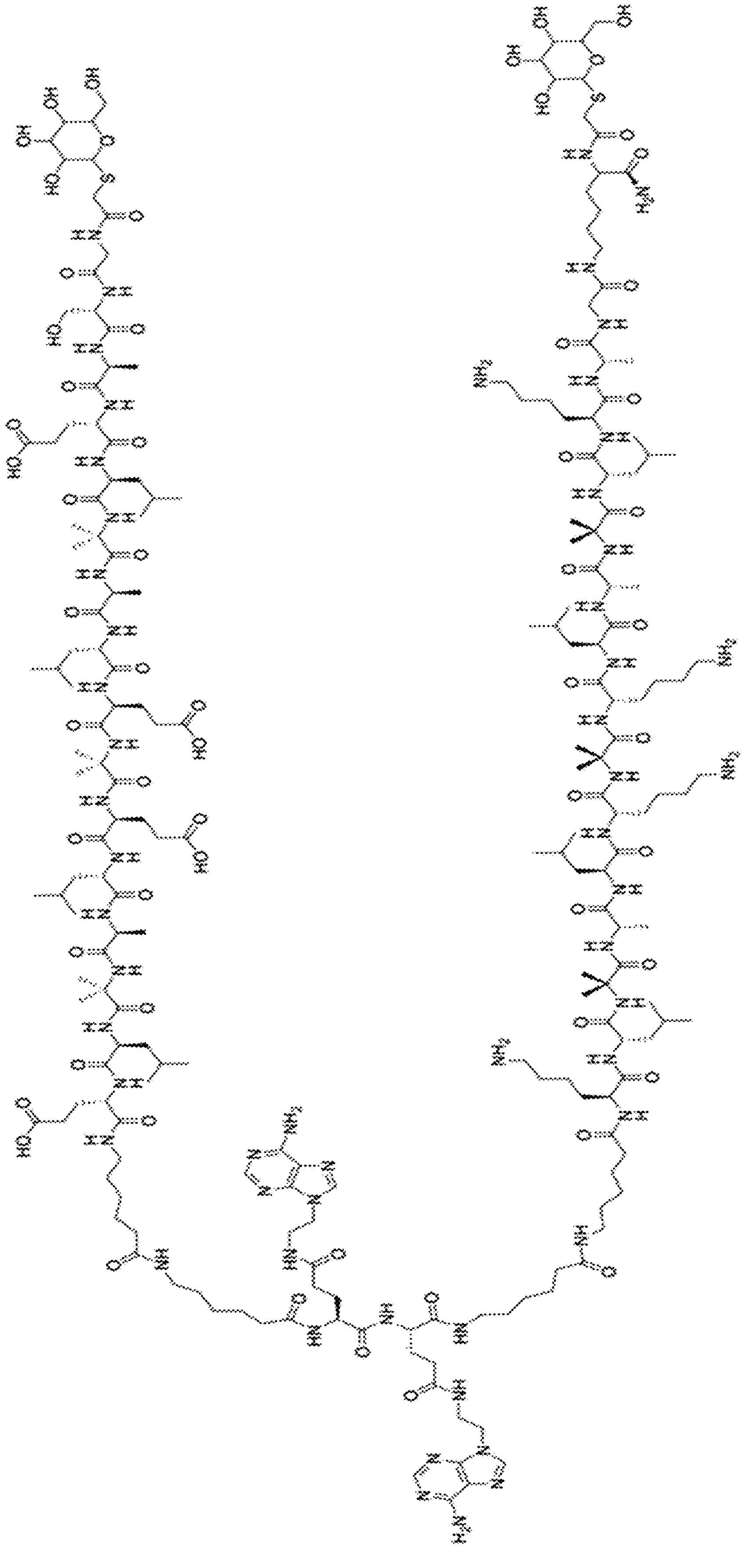
FIG. 38C shows the structure of a peptide-molecule conjugate of Example 18 ($Glc_2$-AA-U6).
Figure 38D:
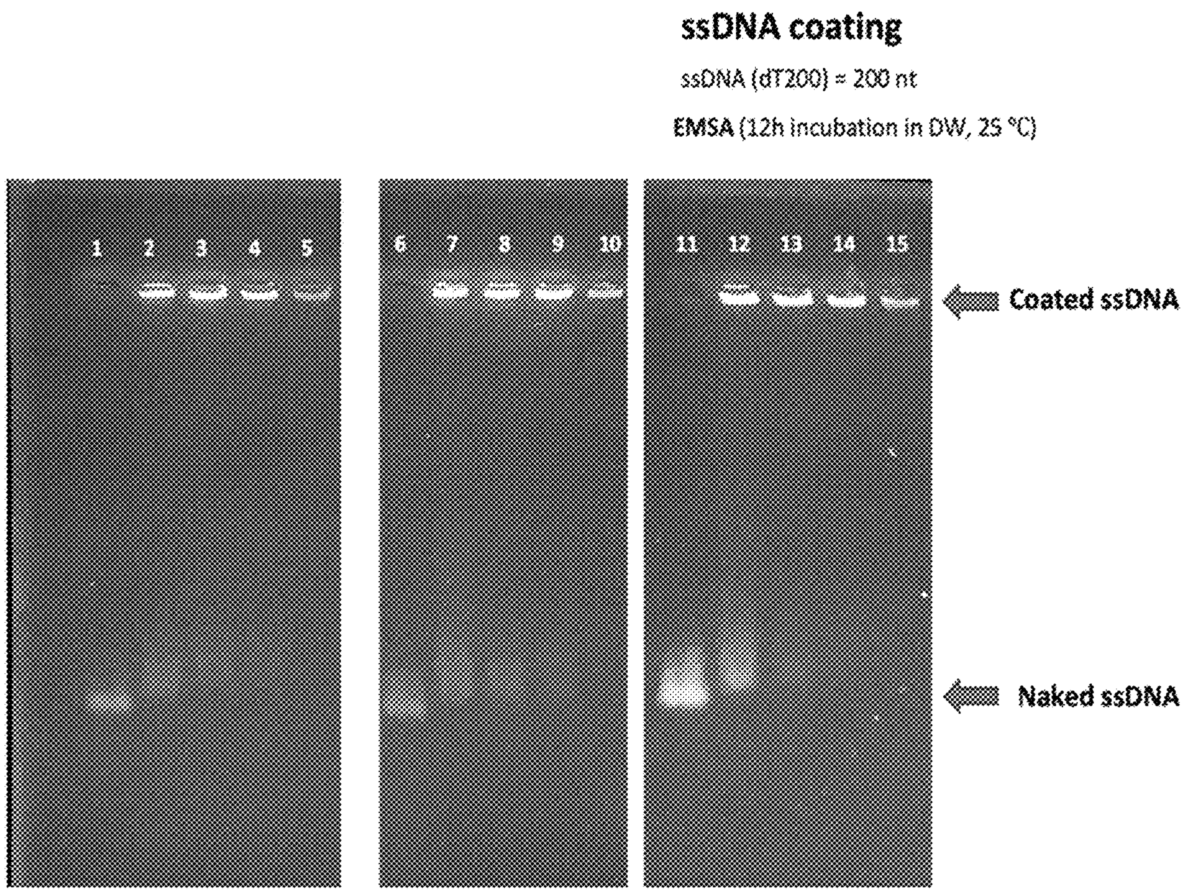
FIG. 38D shows an EMSA result for nanostructures prepared by mixing peptide-molecule conjugates of Examples 16, 17 and 18 ($Glc_2$-AA-U2, $Glc_2$-AA-U4 and $Glc_2$-AA-U6) and ssDNA PolyT200 at different nucleobase ratios.

FIG. 38A shows the structure of the peptide-molecule conjugate of Example 16 ($Glc_2$-AA-U2), FIG. 38B shows the structure of the peptide-molecule conjugate of Example 17 ($Glc_2$-AA-U4), and FIG. 38C shows the structure of the peptide-molecule conjugate of Example 18 ($Glc_2$-AA-U6). FIG. 38D shows an EMSA result for the nanostructures prepared by mixing peptide-molecule conjugates of Examples 16, 17 and 18 ($Glc_2$-AA-U2, $Glc_2$-AA-U4 and $Glc_2$-AA-U6) and the ssDNA PolyT200 at different nucleobase ratios.

The peptide-molecule conjugates of Examples 16, 17 and 18 ($Glc_2$-AA-U2, $Glc_2$-AA-U4, $Glc_2$-AA-U6) were dispersed in distilled water. 2500 μM, 3125 μM, 3750 μM and 4375 μM aqueous solutions (nucleobase ratio=40, 50, 60 or 70) of the peptide-molecule conjugate of Example 16 ($Glc_2$-AA-U2) 1875 μM, 2500 μM, 3125 μM and 3750 μM aqueous solutions (nucleobase ratio=30, 40, 50 or 60) of the peptide-molecule conjugate of Example 17 ($Glc_2$-AA-U4), and 1250 μM, 1875 μM, 2500 μM, 3125 μM aqueous solutions (nucleobase ratio=20, 30, 40 or 50) of the peptide-molecule conjugate of Example 18 ($Glc_2$-AA-U6) were prepared. After preparing the mixtures of the peptide-molecule conjugates of Examples 16, 17 and 18 ($Glc_2$-AA-U2, $Glc_2$-AA-U4, $Glc_2$-AA-U6) and the ssDNA PolyT200 (5 μL) at the nucleobase ratios described above, they were analyzed by EMSA.

As shown in FIG. 38, it was confirmed that $Glc_2$-AA-U2/PolyT200, $Glc_2$-AA-U4/PolyT200 and $Glc_2$-AA-U6/PolyT200 nanostructures were formed successfully from the peptide-molecule conjugates of Examples 16, 17 and 18 ($Glc_2$-AA-U2, $Glc_2$-AA-U4, $Glc_2$-AA-U6) and the ssDNA PolyT200.

Figure 39A:
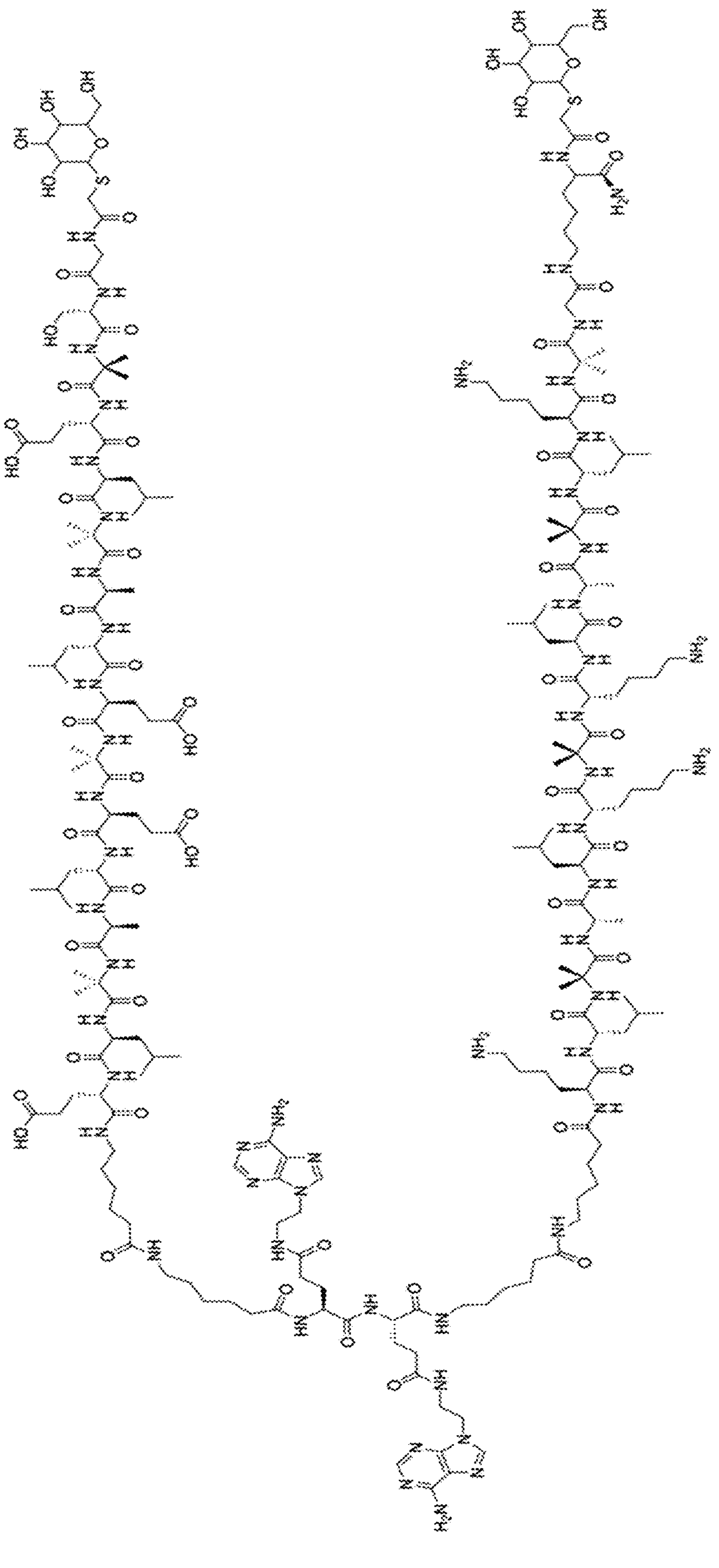
FIG. 39A shows the structure of a peptide-molecule conjugate of Example 19 ($Glc_2$-AA-U8)
Figure 39B:
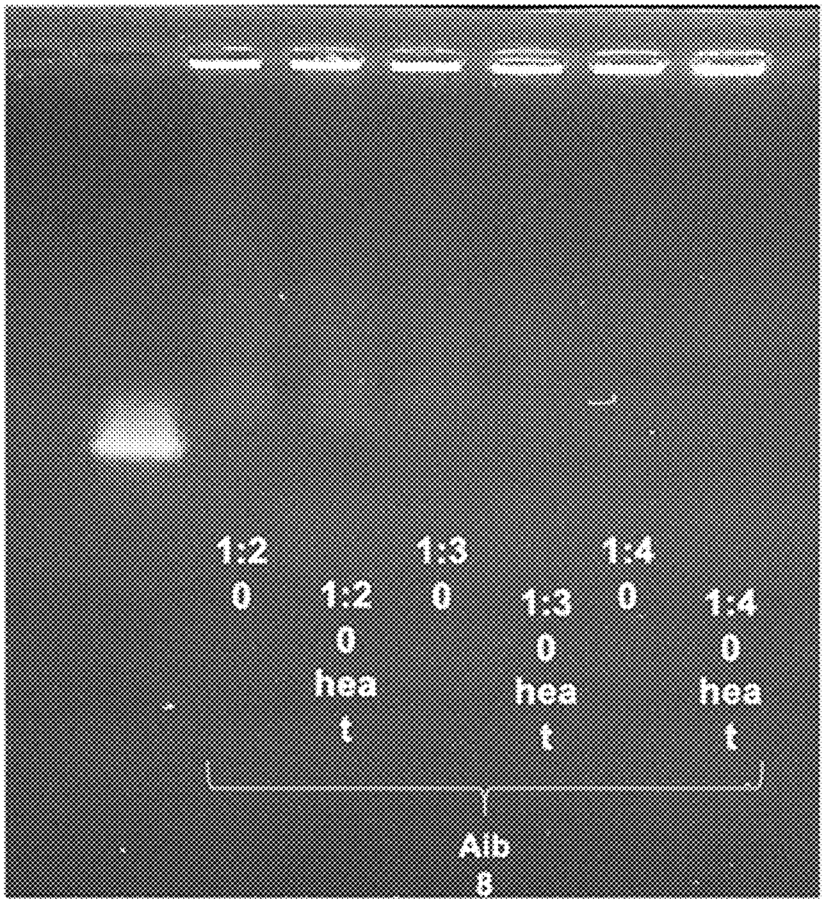
FIG. 39B shows an EMSA result for self-assembly nanostructures prepared by adding a peptide-molecule conjugate of Example 19 ($Glc_2$-AA-U8) and ssDNA polyT200 at different nucleobase ratios and applying ultrasonic waves and heat.

FIG. 39A shows the structure of the peptide-molecule conjugate of Example 19 ($Glc_2$-AA-U8), and FIG. 39B shows an EMSA result for self-assembly nanostructures prepared by adding the peptide-molecule conjugate of Example 19 ($Glc_2$-AA-U8) and ssDNA polyT200 at different nucleobase ratios and applying ultrasonic waves and heat.

1250 μM, 1875 μM and 2500 μM aqueous solutions were prepared by dispersing the peptide-molecule conjugate of Example 19 ($Glc_2$-AA-U8) in distilled water, respectively. The aqueous solution of the peptide-molecule conjugate of Example 19 ($Glc_2$-AA-U8) was sonicated for 5 minutes or heated at 90° C. for 5 minutes, respectively. The heated peptide-molecule conjugate was indicated by 'heat'.

The mixtures prepared by mixing the peptide-molecule conjugate of Example 19 ($Glc_2$-AA-U8) aqueous solution (sonicated or heated) and ssDNA PolyT200 (5 μL) at nucleobase ratios of 20, 30 or 40 were analyzed by EMSA.

As shown in FIGS. 39A and 39B, it was confirmed that the peptide-molecule conjugate ($Glc_2$-AA-U8) forms a $Glc_1$-AA-U8/ssDNAPolyT200 nanostructure by successfully binding to ssDNA PolyT200 when it is either sonicated or treated. This means that the peptide-molecule conjugate according to the present disclosure is strongly resistant to sonication and heating.

Figure 40A:
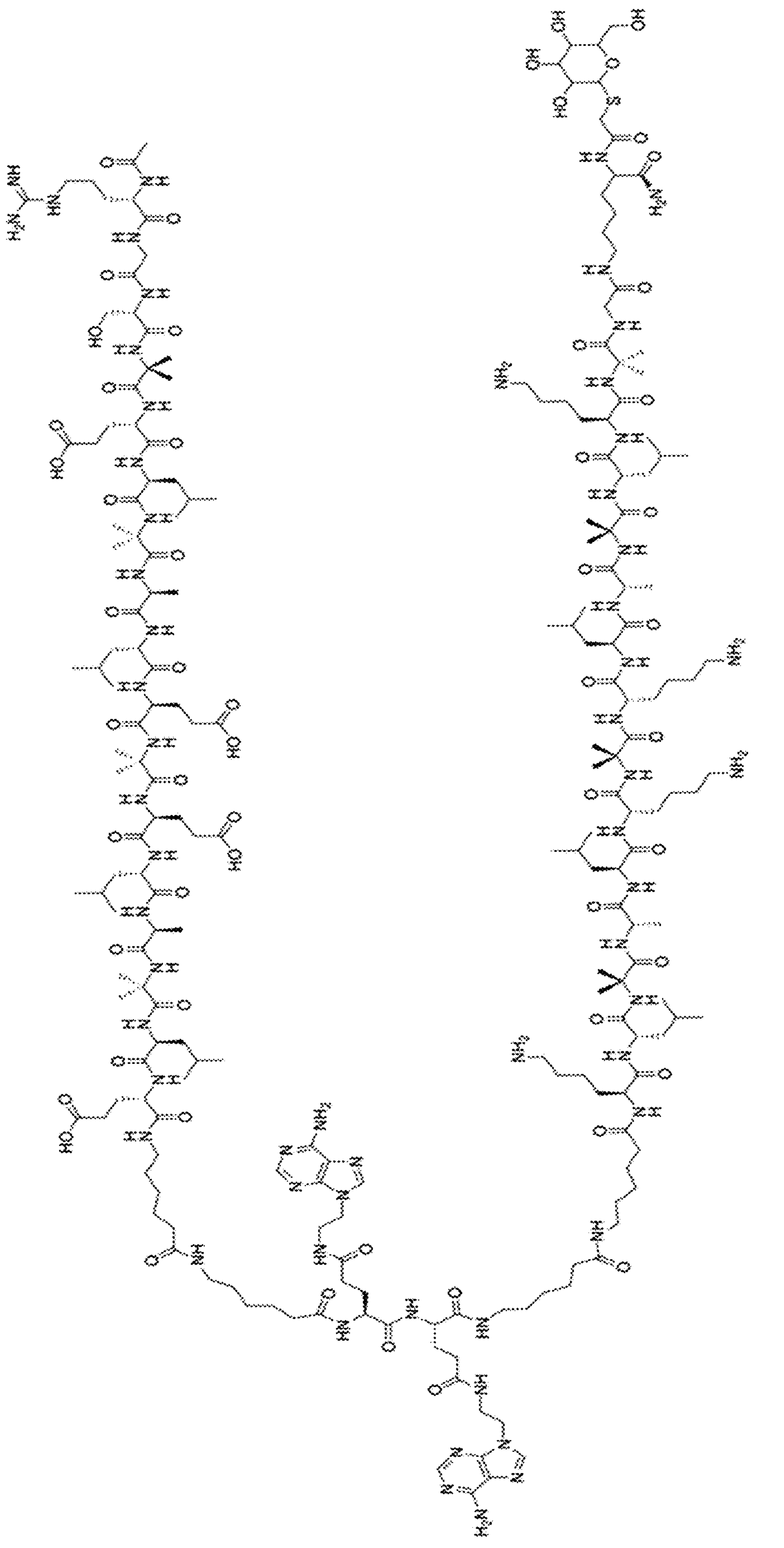
FIG. 40A shows the structure of a peptide-molecule conjugate of Example 20 (R-AA-Glc-U8)
Figure 40B:
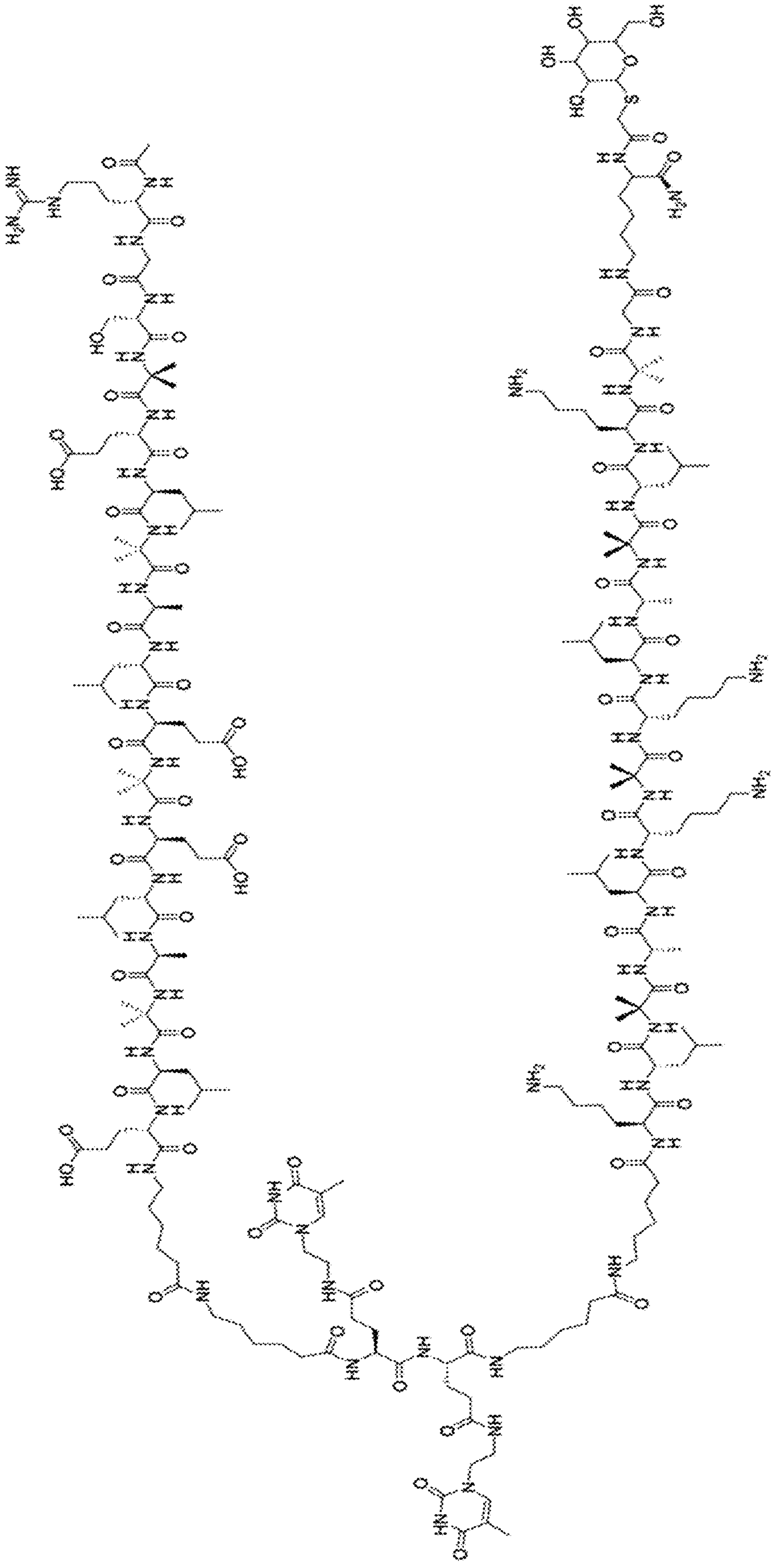
FIG. 40B shows the structure of a peptide-molecule conjugate of Example 21 (R-TT-Glc-U8)
Figure 40C:
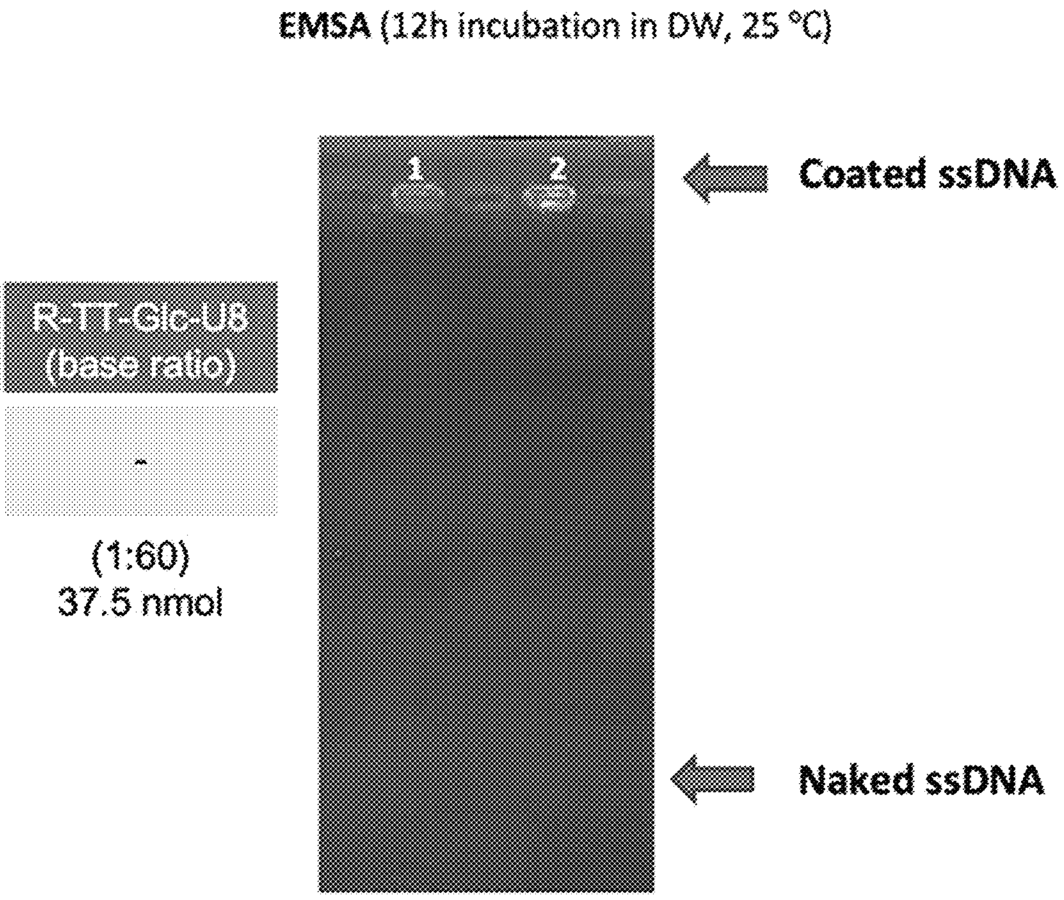
FIG. 40C shows an EMSA result for nanostructures prepared by mixing peptide-molecule conjugates of Examples 20 and 21 (R-AA-Glc-U8 and R-TT-Glc-U8) and ssDNA polyT200 at a nucleobase ratio of 60.

FIG. 40A shows the structure of the peptide-molecule conjugate of Example 20 (R-AA-Glc-U8), FIG. 40B shows the structure of the peptide-molecule conjugate of Example 21 (R-TT-Glc-U8), and FIG. 40C shows an EMSA result for the nanostructures prepared by mixing the peptide-molecule conjugates of Examples 20 and 21 (R-AA-Glc-U8 and R-TT-Glc-U8) and ssDNA polyT200 at a nucleobase ratio of 60.

1875 μM aqueous solutions were prepared by dispersing the peptide-molecule conjugates of Examples 20 and 21 (R-AA-Glc-U8, R-TT-Glc-U8) in distilled water, respectively. After preparing mixtures by mixing the peptide-molecule conjugates of Examples 20 and 21 (R-AA-Glc-U8, R-TT-Glc-U8) with ssDNA PolyT200 (5 μL) at a nucleobase ratio 60, they were analyzed by EMSA.

As shown in FIGS. 40A-40C, it was confirmed that the peptide-molecule conjugates of Examples 20 and 21 (R-AA-Glc-U8, R-TT-Glc-U8) successfully form R-AA-Glc-U8/ssDNA PolyT200 and R-TT-Glc-U8/ssDNA PolyT200 nanostructures by binding to ssDNA PolyT200.

Figure 41B:
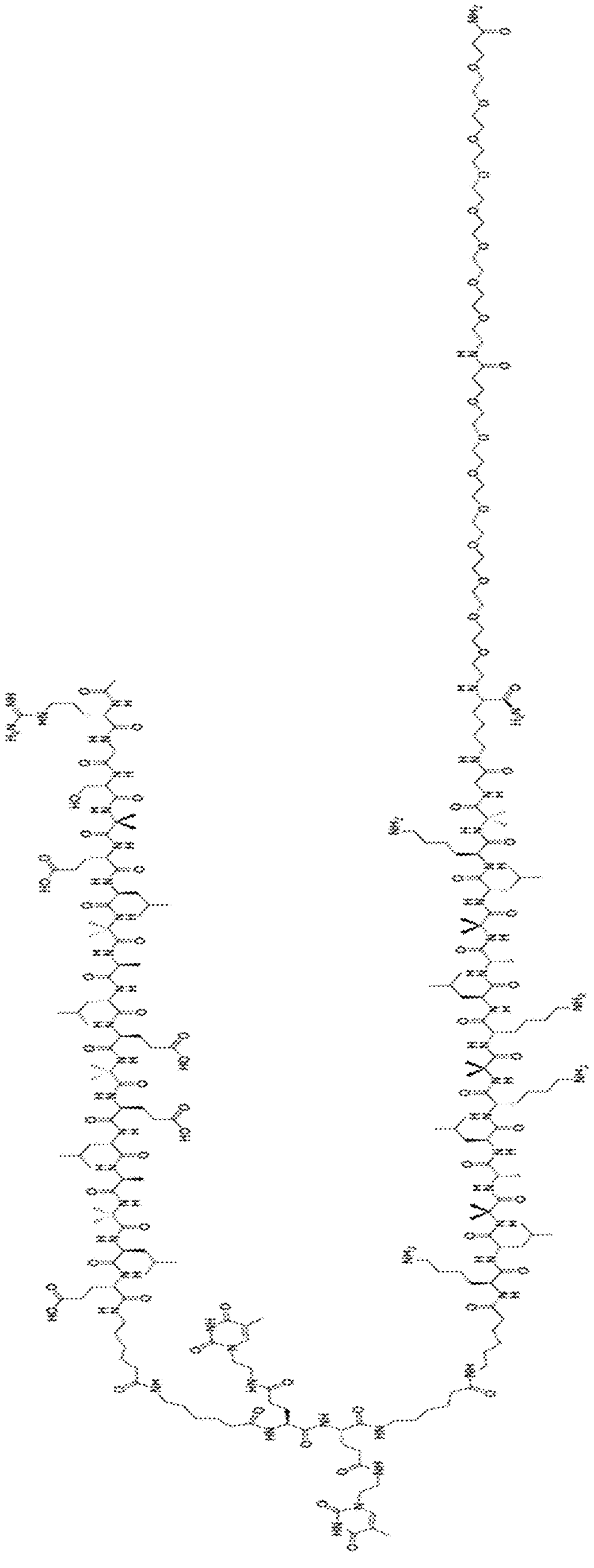
FIG. 41B shows the structure of a peptide-molecule conjugate of Example 23 (R-TT-PEG$8_2$-U8)
Figure 41C:
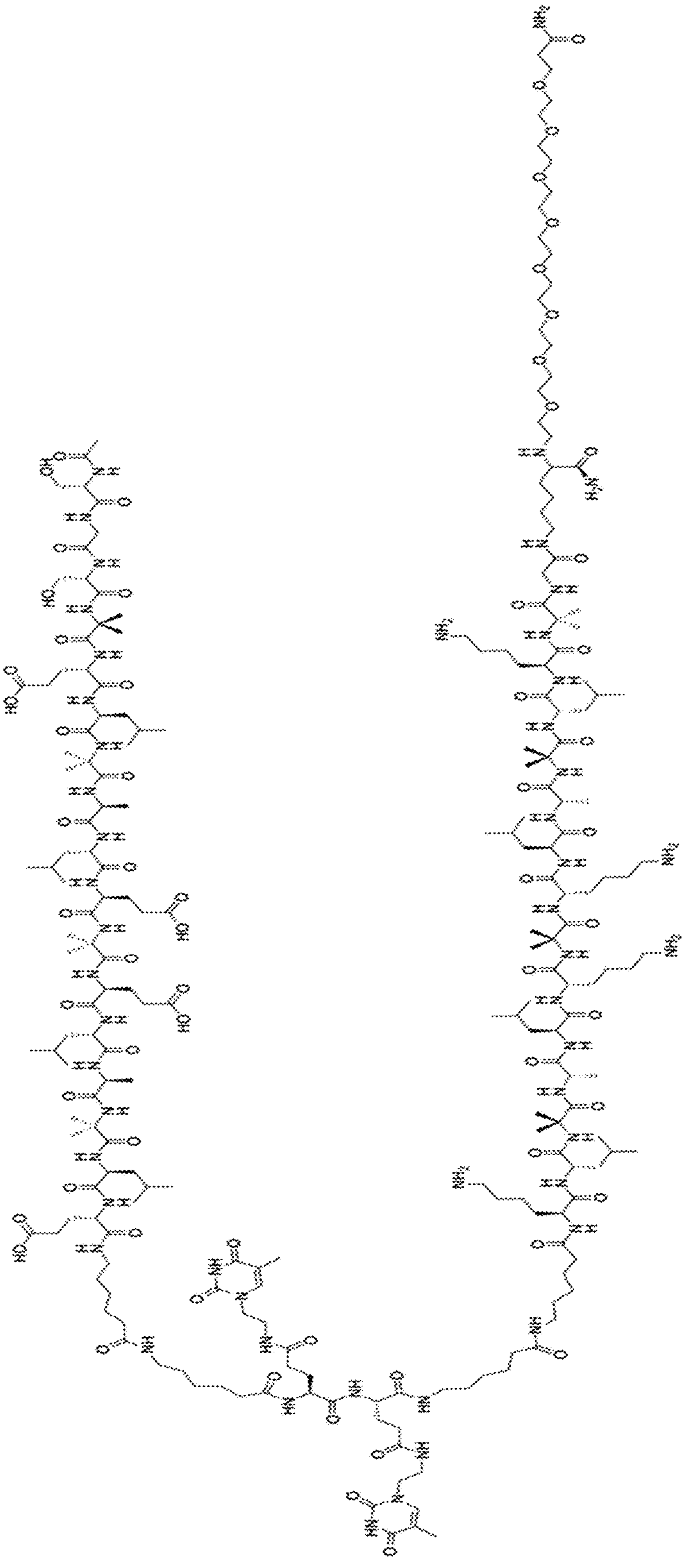
FIG. 41C shows the structure of a peptide-molecule conjugate of Example 24 (S-TT-PEG8-U8).
Figure 41D:
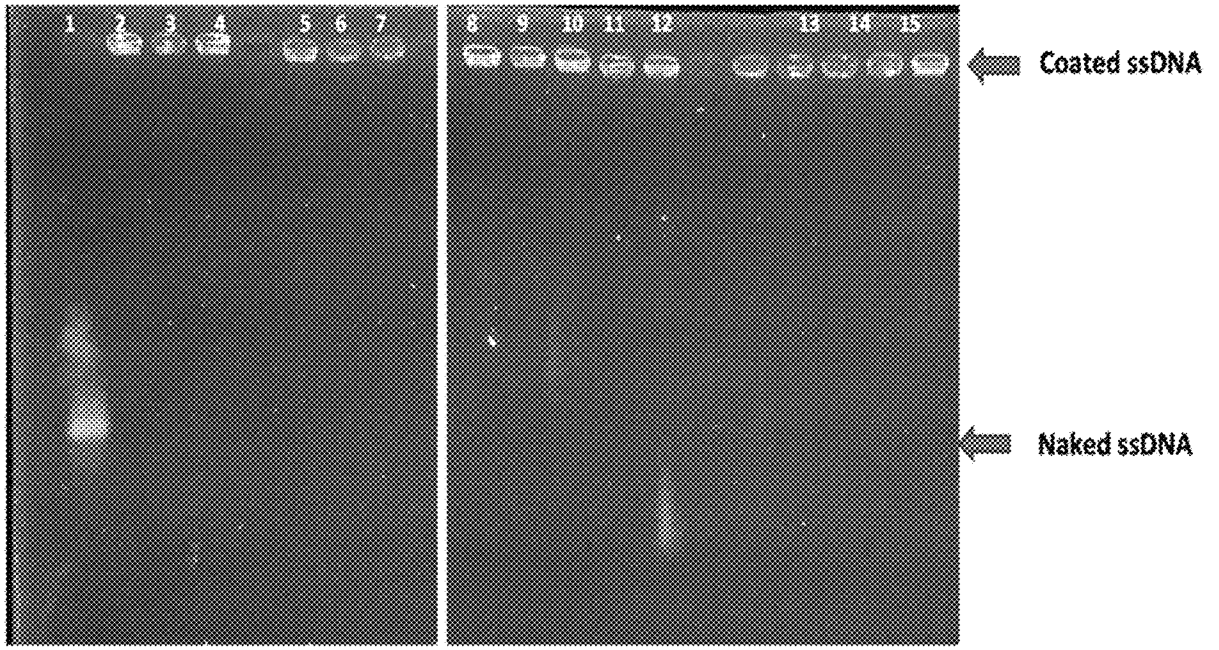
FIG. 41D shows an EMSA result for nanostructures prepared by mixing peptide-molecule conjugates of Examples 22, 23 and 24 (R-TT-PEG8-U8, R-TT-PEG$8_2$-U8, S-TT-PEG8-U8) and ssDNA polyT200 at different nucleobase ratios.

FIG. 41A shows the structure of the peptide-molecule conjugate of Example 22 (R-TT-PEG8-U8), FIG. 41B shows the structure of the peptide-molecule conjugate of Example 23 (R-TT-$PEG8_2$-U8), and FIG. 41C shows the structure of the peptide-molecule conjugate of Example 24 (S-TT-PEG8-U8). FIG. 41D shows an EMSA result for the nanostructures prepared by mixing the peptide-molecule conjugates of Examples 22, 23 and 24 (R-TT-PEG8-U8, R-TT-$PEG8_2$-U8, S-TT-PEG8-U8) and ssDNA polyT200 at different nucleobase ratios.

Aqueous solutions of the peptide-molecule conjugate of Example 22 (R-AA-PEG8-U8) at 2500 μM, 3125 μM or 3750 μM (nucleobase ratio=40, 50 or 60), the peptide-molecule conjugate of Example 23 (R-TT-$PEG8_2$-U8) at 1875 μM, 3125 μM or 3750 μM (nucleobase ratio=40, 50 or 60) and the peptide-molecule conjugate of Example 24 (S-TT-PEG8-U8) at 1875 μM, 3125 μM, 3750 μM or 6250 μM (nucleobase ratio=40, 50, 60 or 100) were prepared by dispersing the peptide-molecule conjugates of Examples 22, 23 and 24 (R-AA-PEG8-U8, R-TT-$PEG8_2$-U8, S-TT-PEG8-U8) in distilled water, respectively. After preparing mixtures by mixing the peptide-molecule conjugates of Examples 22, 23 and 24 (R-AA-PEG8-U8, R-TT-$PEG8_2$-U8, S-TT-PEG8-U8) and ssDNA PolyT200 (5 μL) at different nucleobase ratios, they were analyzed by EMSA.

As shown in FIG. 41, it was confirmed that the peptide-molecule conjugates of Examples 22, 23 and 24 (R-AA-PEG8-U8, R-TT-$PEG8_2$-U8, S-TT-PEG8-U8) successfully form R-AA-PEG8-U8/ssDNA PolyT200, R-TT-$PEG8_2$-U8/ssDNA PolyT200 and S-TT-PEG8-U8/ssDNA PolyT200 nanostructures by binding to ssDNA PolyT200.

Test Example 12. Intracellular Delivery Pathway of Nanostructure of Peptide-Molecule Conjugate and ssDNA 12-1. Preparation of Nanostructure of Peptide-Molecule Conjugate and ssDNA After preparing a nanostructure of the peptide-molecule conjugate and ssDNA, its intracellular delivery effect was evaluated. A control groups was treated with nothing (mock) and a comparison group was treated only with FAM-AS-PolyT180 (FAM-AS-PolyT180 only).

As the ssDNA, FAM-labeled ssDNA (hereinafter, referred to as 'FAM-AS-PolyT180') hybridized with an FAM-labeled oligonucleotide probe was used. Specifically, the FAM-AS-PolyT180 ssDNA was prepared using an FAM-labeled antisense oligonucleotide (FAM-AS: /56-FAM/GC GAG CTG CAC GCT GCC GTC; SEQ ID NO 18) and PolyT180 ((TTT) 60-GAC GGC AGC GTG CAG CTC GC; SEQ ID NO 19). First, after mixing FAM-AS and ssDNA of the same volumes and concentrations, the FAM-AS-PolyT180 was prepared by heating the mixture for 3 minutes at 94° C. and slowly cooling at room temperature.

The peptide-molecule conjugate prepared in Example 19 ($Glc_2$-AA-U8) and the FAM-AS-PolyT180 were mixed in distilled water at a charge ratio (+/− ratio) of 40:1. After incubation at room temperature overnight, a $Glc_2$-AA-U8/FAM-AS-PolyT180 nanostructure sample was prepared by diluting 5-fold with Opti-MEM. Immediately before the mixing, the peptide-molecule conjugate prepared in Example 19 ($Glc_2$-AA-U8) was sonicated for 5 minutes.

12-2. Iintracellular Delivery Efficiency

HeLa (ATCC CCL-2) cells were used. The Hela cells were cultured in DMEM (Dulbecco's modified Eagle's medium) containing 10% (v/v) FBS and penicillin-streptomycin.

After seeding $1\times10^4$ HeLa cells in each well of a 96-well cell culture plate (SPL, Pocheon, Korea) and culturing for 24 hours, the sample (200 μL) or the control substance (200 μL) was added to each well and the cells were cultured for 2 hours. The amount of ssDNA added to each well was 1 μg. The 96-well cell culture plate (SPL, Pocheon, Korea) and a Nunc™ Lab-Tek™ II chambered coverglass (Thermo Scientific, Waltham, USA) were used for flow cytometry and confocal microscopy. The procedures of the flow cytometry and confocal microscopy are described in detail above in the Experimental methods section.

Figure 42:
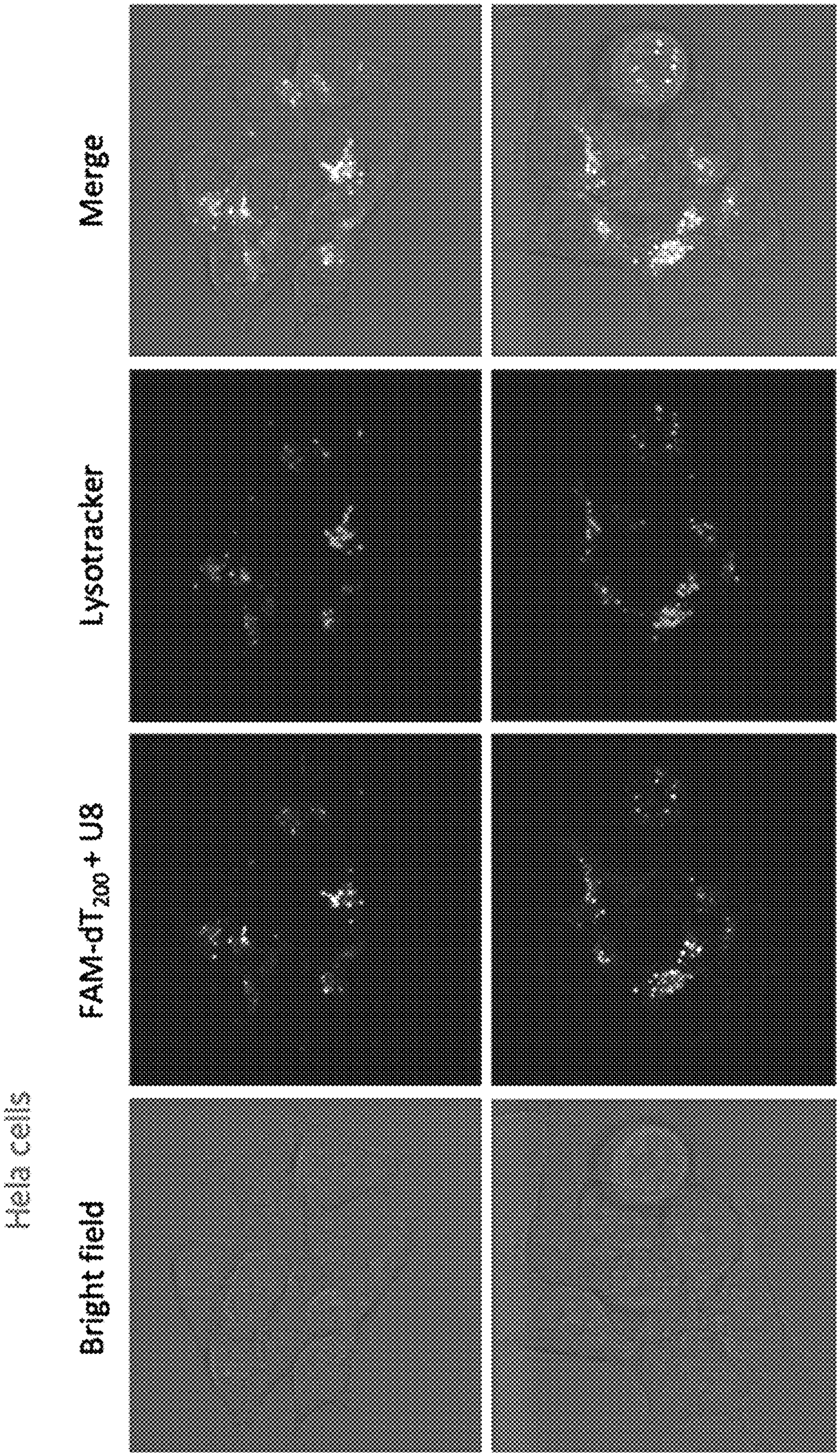
FIG. 42 shows CLSM (confocal laser scanning microscopy) images obtained by administering a $Glc_2$-AA-U8/FAM-AS-Poly180 nanostructure (nucleobase ratio=1:40) to Hela cells. FAM-AS-PolyT180 is shown in green color, LysoTracker in red, and colocalization in yellow.

FIG. 42 shows the CLSM (confocal laser scanning microscopy) images obtained by administering the $Glc_2$-AA-U8/FAM-AS-Poly180 nanostructure (nucleobase ratio=1:40) to Hela cells. FAM-AS-PolyT180 is shown in green color, LysoTracker in red, and colocalization in yellow. In FIG. 42, the top and bottom images show different regions of the same cells.

From FIG. 42, it can be seen that the $Glc_2$-AA-U8/FAM-AS-PolyT180 nanostructure can be effectively delivered into the cytoplasm of HeLa cells. That is to say, the $Glc_2$-AA-U8/FAM-AS-PolyT180 nanostructure is very useful as a gene carrier since it can stably deliver the nucleic acid to the cytoplasm.

In addition, the location of the $Glc_2$-AA-U8/FAM-AS-PolyT180 nanostructure corresponded in most cases to those of the LysoTracker-labeled acidic cell organelles. That is to say, it can be seen that the $Glc_2$-AA-U8/FAM-AS-PolyT180 nanostructure effectively delivers the nucleic acid material into the cytoplasm of cells via acidic cell organelles such as lysosomes.

12-3. Preparation of Nanostructure of Peptide-Molecule Conjugate and EGFP mRNA

Aqueous solutions were prepared by dispersing the peptide-molecule conjugates of Examples 19, 25, 26 and 27 ($Glc_2$-AA-U8, $Glc_2$-CC-U8, $Glc_2$-GG-U8, $Glc_2$-TT-U8) in distilled water. After sonicating the aqueous solution for 5 minutes and immediately mixing with an EGFP mRNA solution (5 μL) heated at 70° C. for 2 minutes, the mixture was heated further for 3 minutes and then snap-cooled on ice for 10 minutes. The EGFP mRNA was CleanCap® enhanced green fluorescent protein (EGFP) mRNA (5-methoxyuridine) (Catalog No.: L-7601) purchased from TriLink BioTechnologies (San Diego, USA).

The nanostructures of the peptide-molecule conjugates ($Glc_2$-AA-U8, $Glc_2$-CC-U8, $Glc_2$-GG-U8, $Glc_2$-TT-U8) and the EGFP mRNA were prepared through the procedures described above. The concentration of the EGFP mRNA was fixed while the concentration of the peptide-molecule conjugates ($Glc_2$-AA-U8, $Glc_2$-CC-U8, $Glc_2$-GG-U8, $Glc_2$-TT-U8) was varied by concentration or dilution. The EGFP mRNA and the peptide-molecule conjugates ($Glc_2$-AA-U8, $Glc_2$-CC-U8, $Glc_2$-GG-U8, $Glc_2$-TT-U8) were mixed at a nucleobase ratio of 1:1-1:15. Because the peptide-molecule conjugate ($Glc_2$-AA-U8, $Glc_2$-CC-U8, $Glc_2$-GG-U8, $Glc_2$-TT-U8) has two nucleobases in the head domain and the EGFP mRNA has 204 nucleobase pairs (AA: 47% of 95 nucleobase pairs, CC: 26% of 54 nucleobase pairs, GG: 21% of 43 nucleobase pairs, UU: 6% of 12 nucleobase pairs), the addition amount of the peptide was calculated based thereon ($Glc_2$-AA-U8: 6%, $Glc_2$-CC-U8: 21%, $Glc_2$-GG-U8: 26%, $Glc_2$-TT-U8: 47%). After incubating the mixture solution overnight, it was analyzed by EMSA.

Figure 43A:
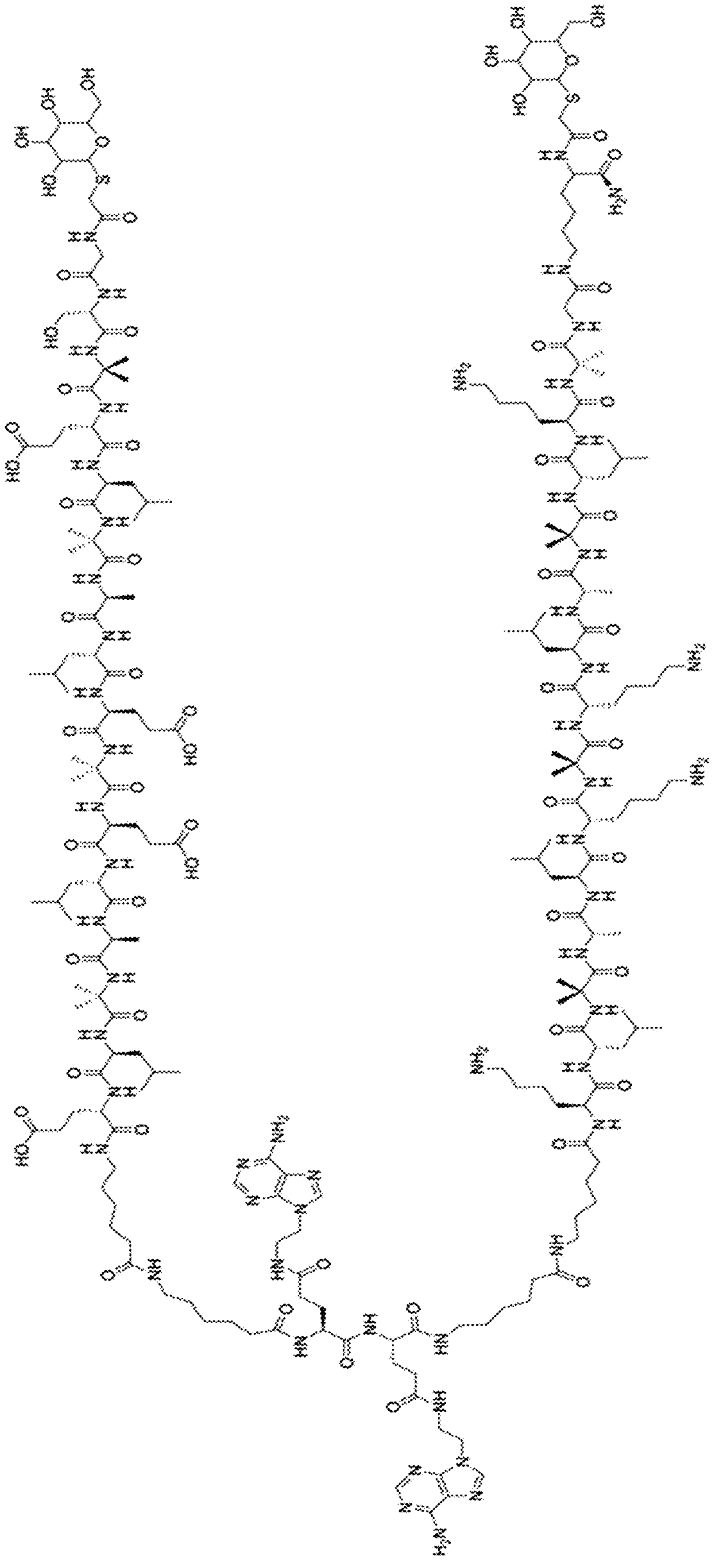
FIG. 43A shows the structure of a peptide-molecule conjugate of Example 19 ($Glc_2$-AA-U8)
Figure 43B:
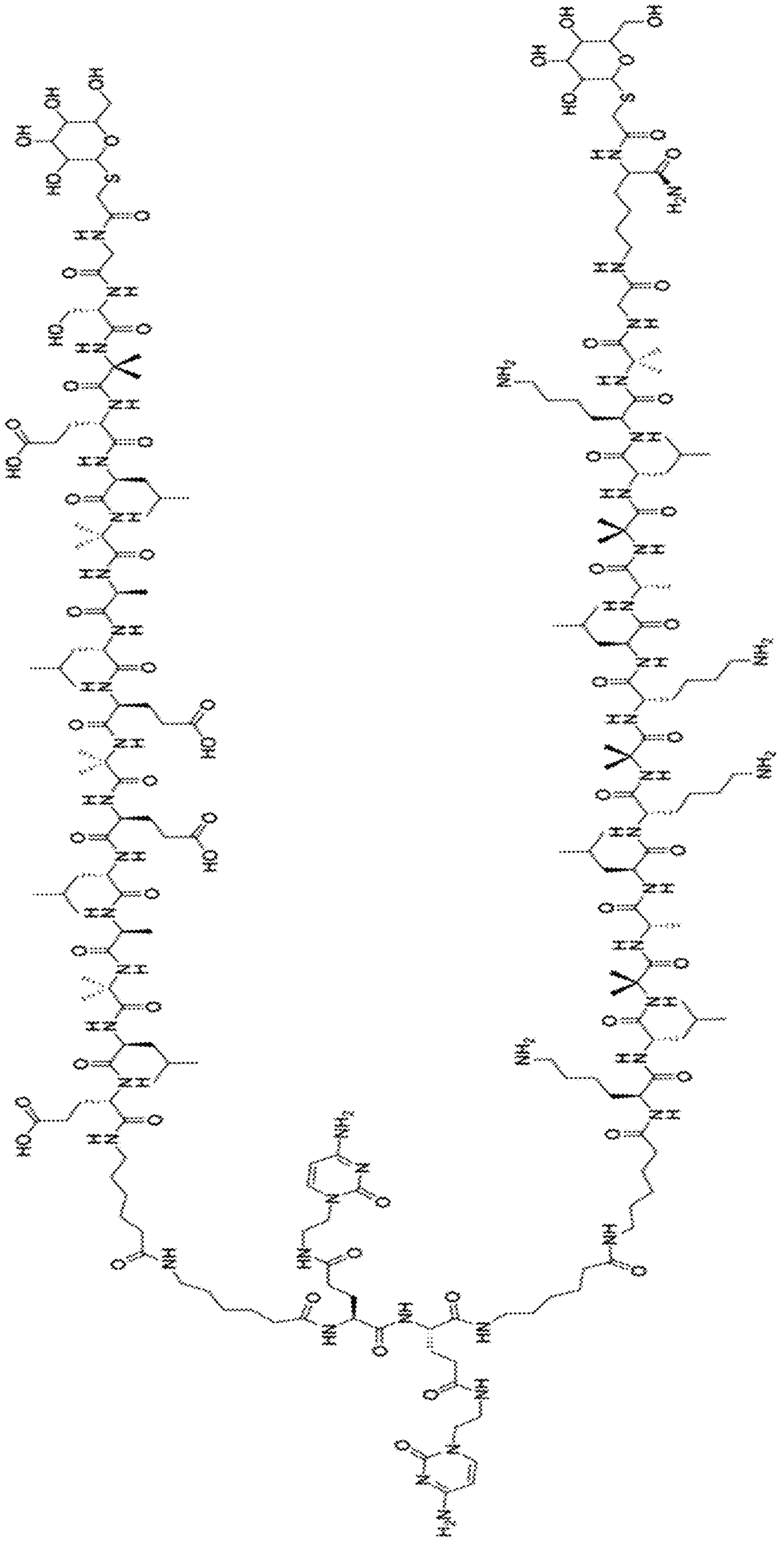
FIG. 43B shows the structure of a peptide-molecule conjugate of Example 25 ($Glc_2$-CC-U8)
Figure 43C:
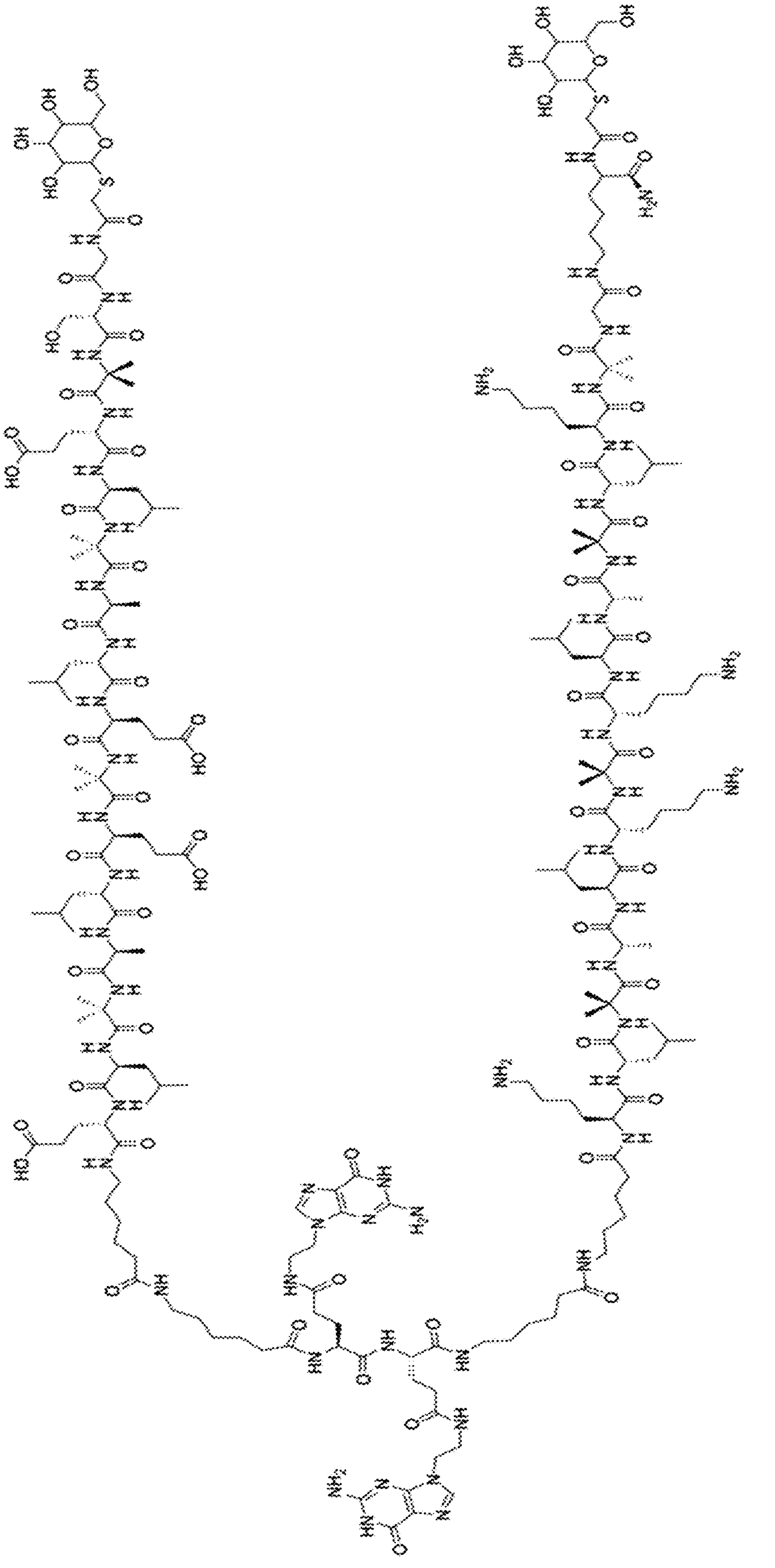
FIG. 43C shows the structure of a peptide-molecule conjugate of Example 26 ($Glc_2$-GG-U8)
Figure 43D:
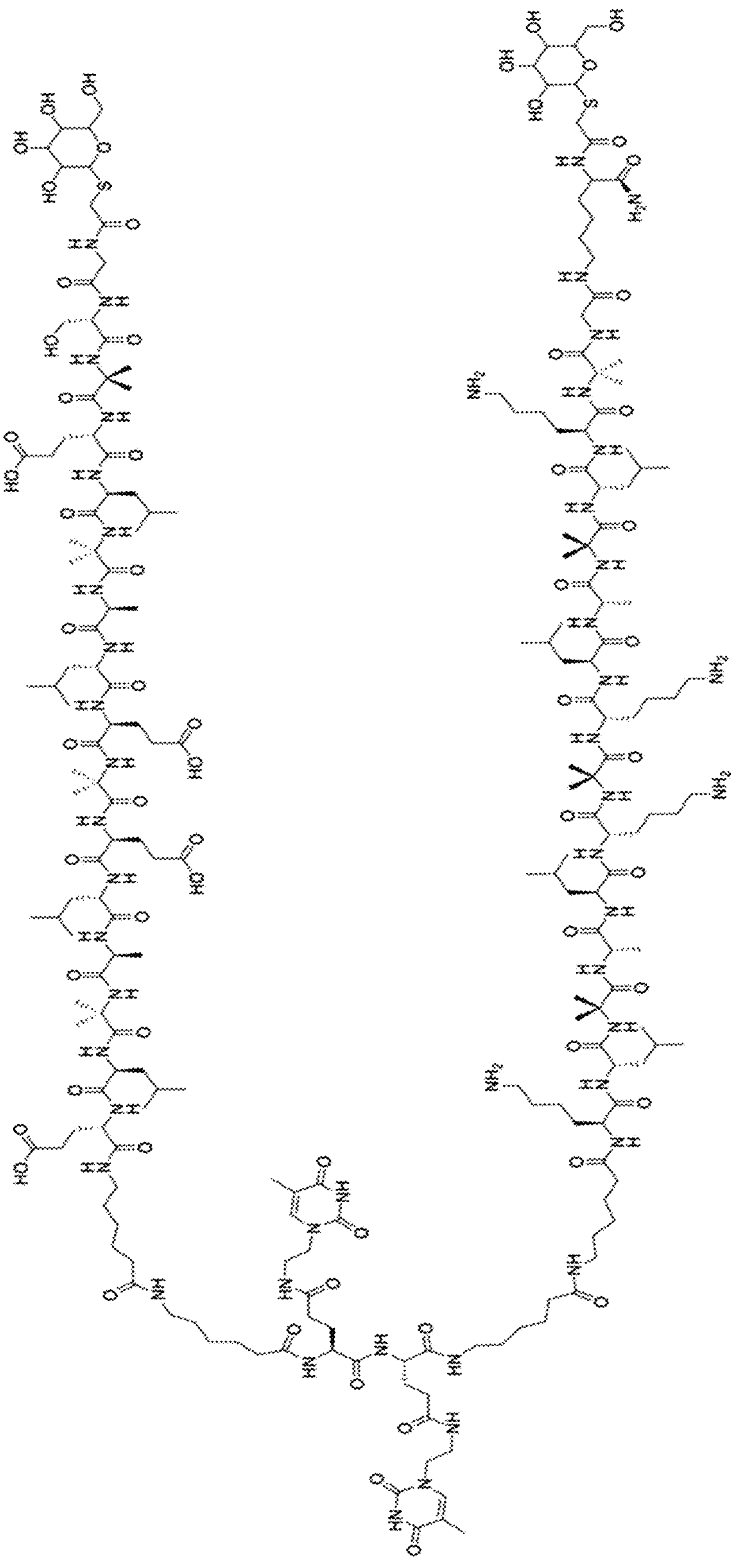
FIG. 43D shows the structure of a peptide-molecule conjugate of Example 27 ($Glc_2$-TT-U8).
Figure 43E:
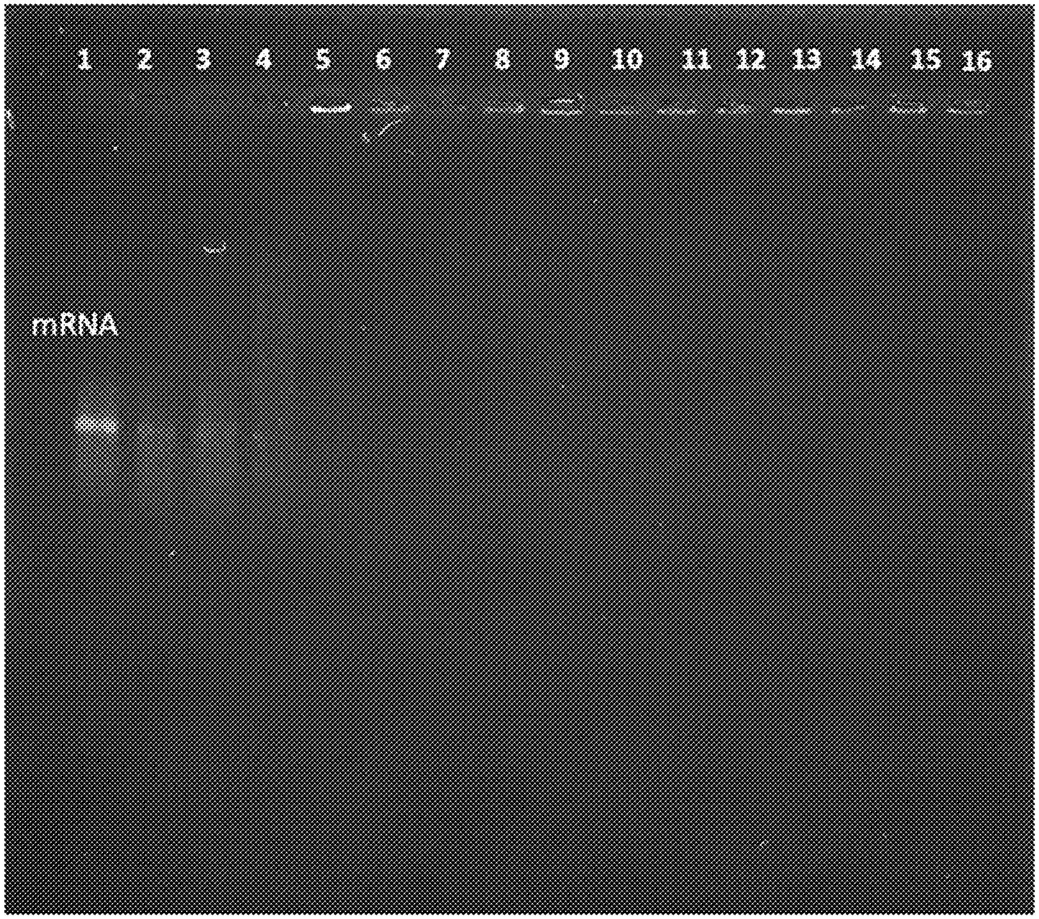
FIG. 43E shows an EMSA result for nanostructures prepared by mixing peptide-molecule conjugates of Examples 19, 25, 26 and 27 ($Glc_2$-AA-U8, $Glc_2$-CC-U8, $Glc_2$-GG-U8 and $Glc_2$-TT-U8) and EGFP mRNA at different nucleobase ratios.

FIG. 43A shows the structure of the peptide-molecule conjugate of Example 19 ($Glc_2$-AA-U8), FIG. 43B shows the structure of the peptide-molecule conjugate of Example 25 ($Glc_2$-CC-U8), FIG. 43C shows the structure of the peptide-molecule conjugate of Example 26 ($Glc_2$-GG-U8), and FIG. 43D shows the structure of the peptide-molecule conjugate of Example 27 ($Glc_2$-TT-U8). FIG. 43E shows an EMSA result for the nanostructures prepared by mixing the peptide-molecule conjugates of Examples 19, 25, 26 and 27 ($Glc_2$-AA-U8, $Glc_2$-CC-U8, $Glc_2$-GG-U8 and $Glc_2$-TT-U8) and EGFP mRNA at different nucleobase ratios.

From FIG. 43, it can be seen that the EGFP mRNA and the peptide-molecule conjugate ($Glc_2$-AA-U8, $Glc_2$-CC-U8, $Glc_2$-GG-U8, $Glc_2$-TT-U8) successfully forms the nanostructure through self-assembly.

Figure 44:
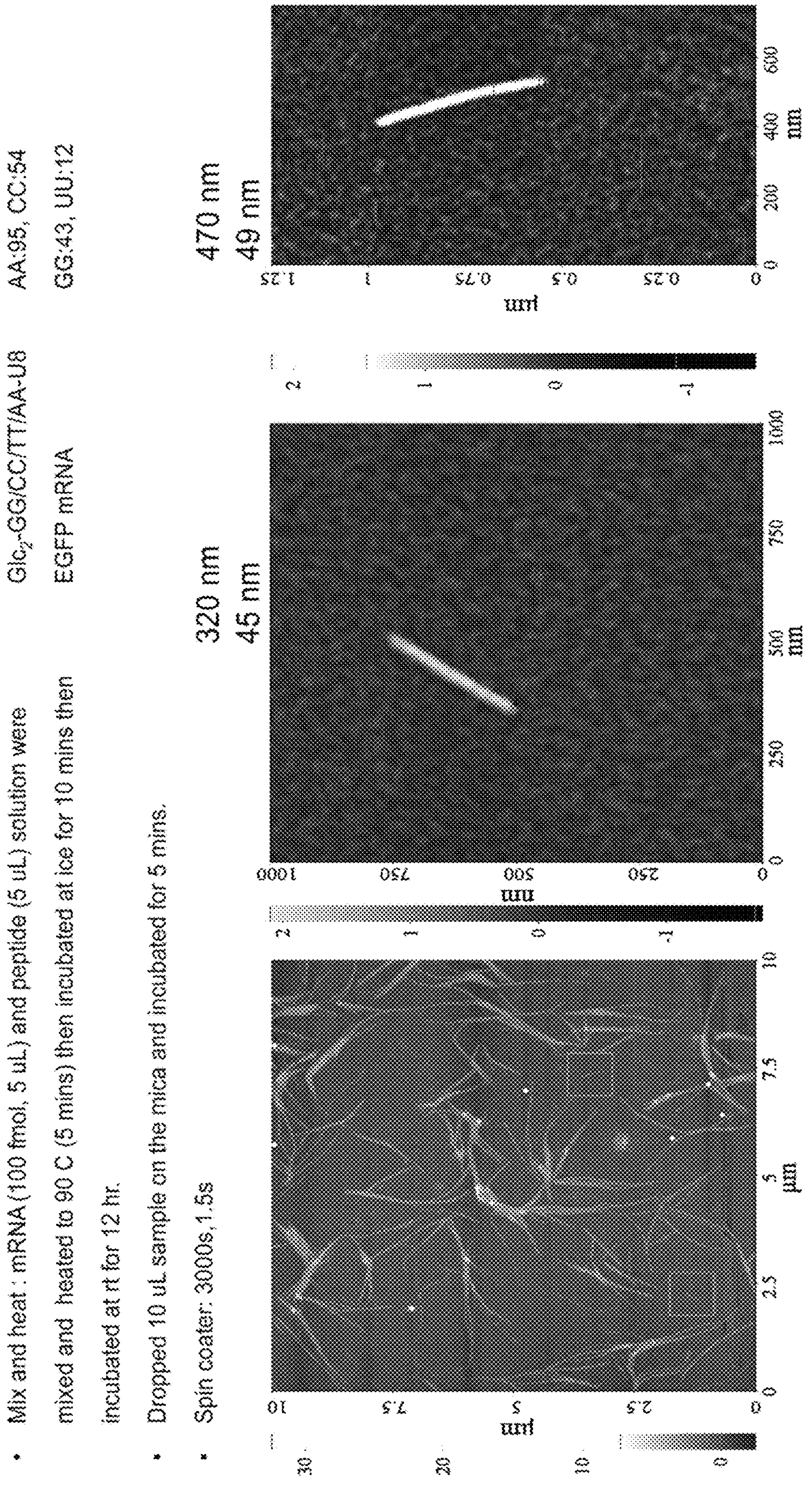
FIG. 44 shows the AFM images of nanostructures prepared by mixing peptide-molecule conjugates of Examples 19, 25, 26 and 27 ($Glc_2$-AA-U8, $Glc_2$-CC-U8, $Glc_2$-GG-U8 and $Glc_2$-TT-U8) and EGP mRNA at a nucleobase ratio of 4:1.
Figure 45:
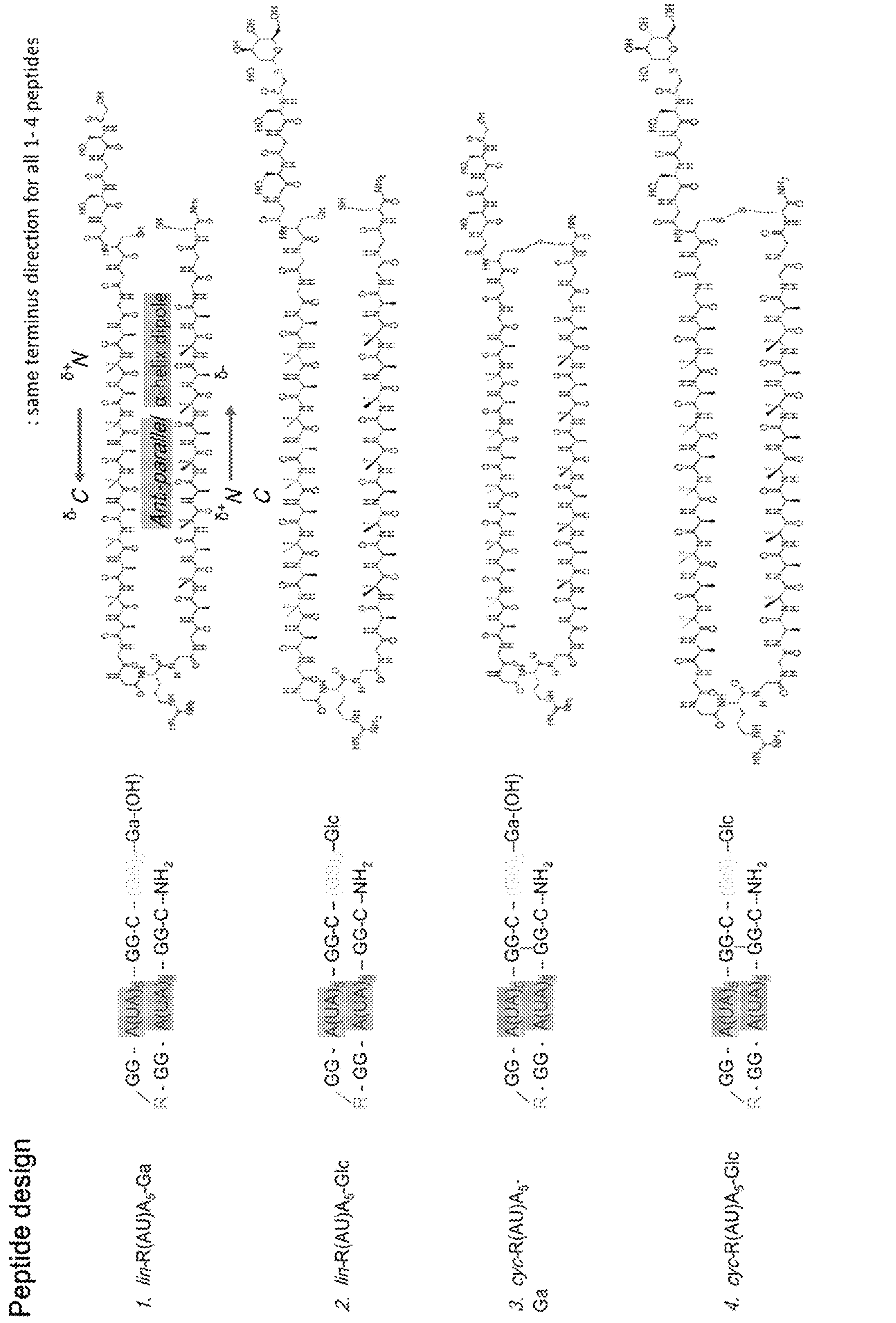
FIG. 45 shows the chemical structure of peptide-molecule conjugates prepared in Examples 28, 29, 30 and 31 (lin-R(AU)$A_5$-Ga, cyc-R(AU)$A_5$-Ga, lin-R(AU)$A_5$-Glc and cyc-R(AU)$A_5$-Glc).

FIG. 44 shows the AFM images of the nanostructures prepared by mixing the peptide-molecule conjugates of Examples 19, 25, 26 and 27 ($Glc_2$-AA-U8, $Glc_2$-CC-U8, $Glc_2$-GG-U8 and $Glc_2$-TT-U8) and EGP mRNA at a nucleobase ratio of 4:1.

From FIG. 44, it can be seen that the nanostructure of the peptide-molecule conjugates of Examples 19, 25, 26 and 27 ($Glc_2$-AA-U8, $Glc_2$-CC-U8, $Glc_2$-GG-U8, $Glc_2$-TT-U8) and EGFP mRNA is in the form of a nanotube with an average diameter of 45 nm.

Test Example 13. Preparation and Analysis of Nanostructure of Linear and Cyclic Peptide-Molecule Conjugate (SAB) and Gene Linear peptide-molecule conjugates (SAB) of Examples 28 and 30 were prepared. Cyclic peptide-molecule conjugates of Examples 29 and 31 (SAB) were prepared by inducing disulfide bond between cysteines (C) in the linear peptide-molecule conjugates of Examples 28 and 30 (SAB). In the peptide-molecule conjugates of Example 30 and Example 31, glucose is bound to the hydrophilic terminal of the tail domain so as to provide cell-targeting function. The structure of the four peptide-molecule conjugates (SAB) is shown specifically in FIG. 45. In the figure, lin indicates linear and cyc indicates cyclic. U indicates 2-aminoisobutyric acid (Aib), Ga indicates glycolic acid, and Glc indicates glucose.

Figure 46:
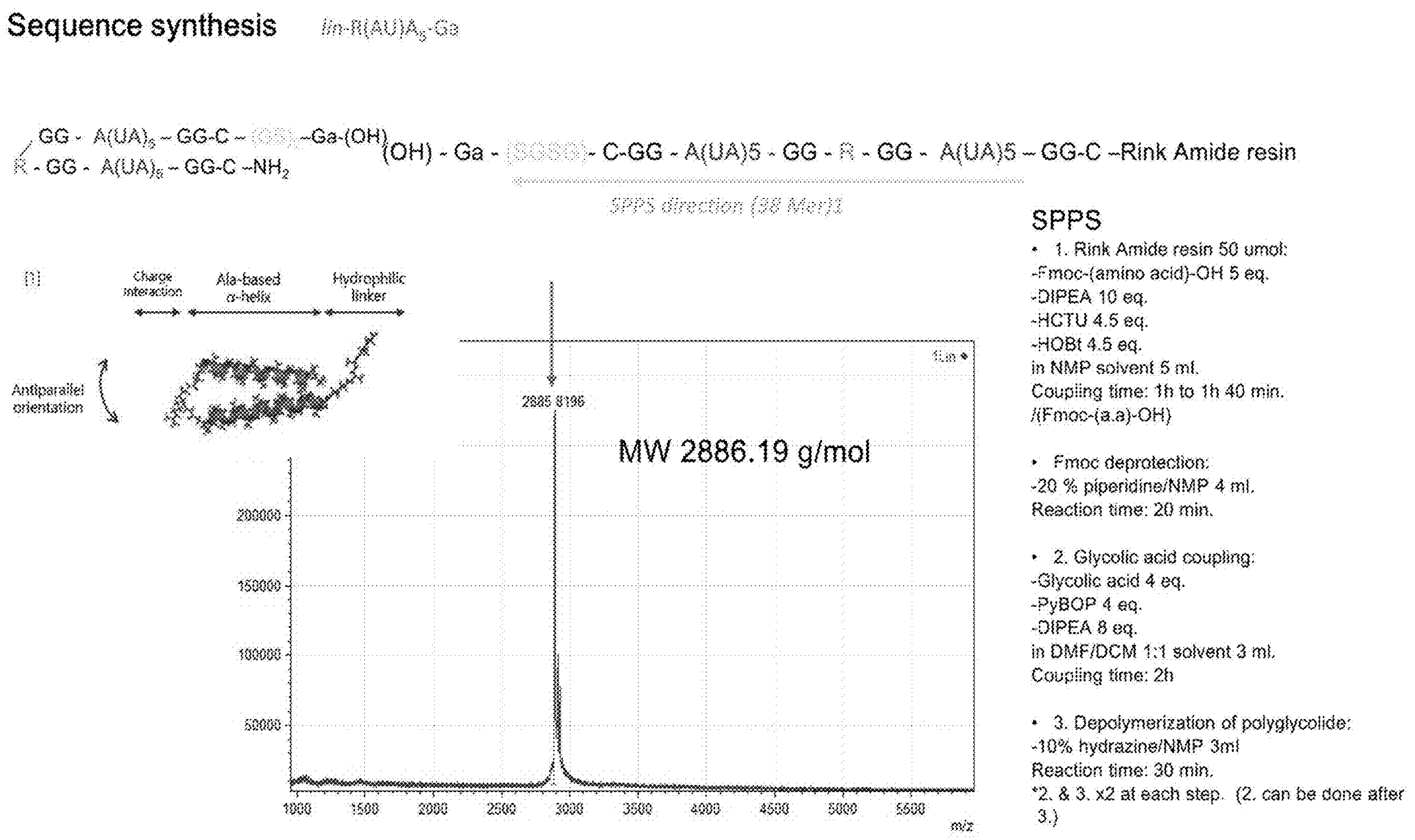
FIG. 46 shows the MALDI-TOF MS analysis result and synthesis condition for a linear peptide-molecule conjugate (SAB #28).
Figure 47:
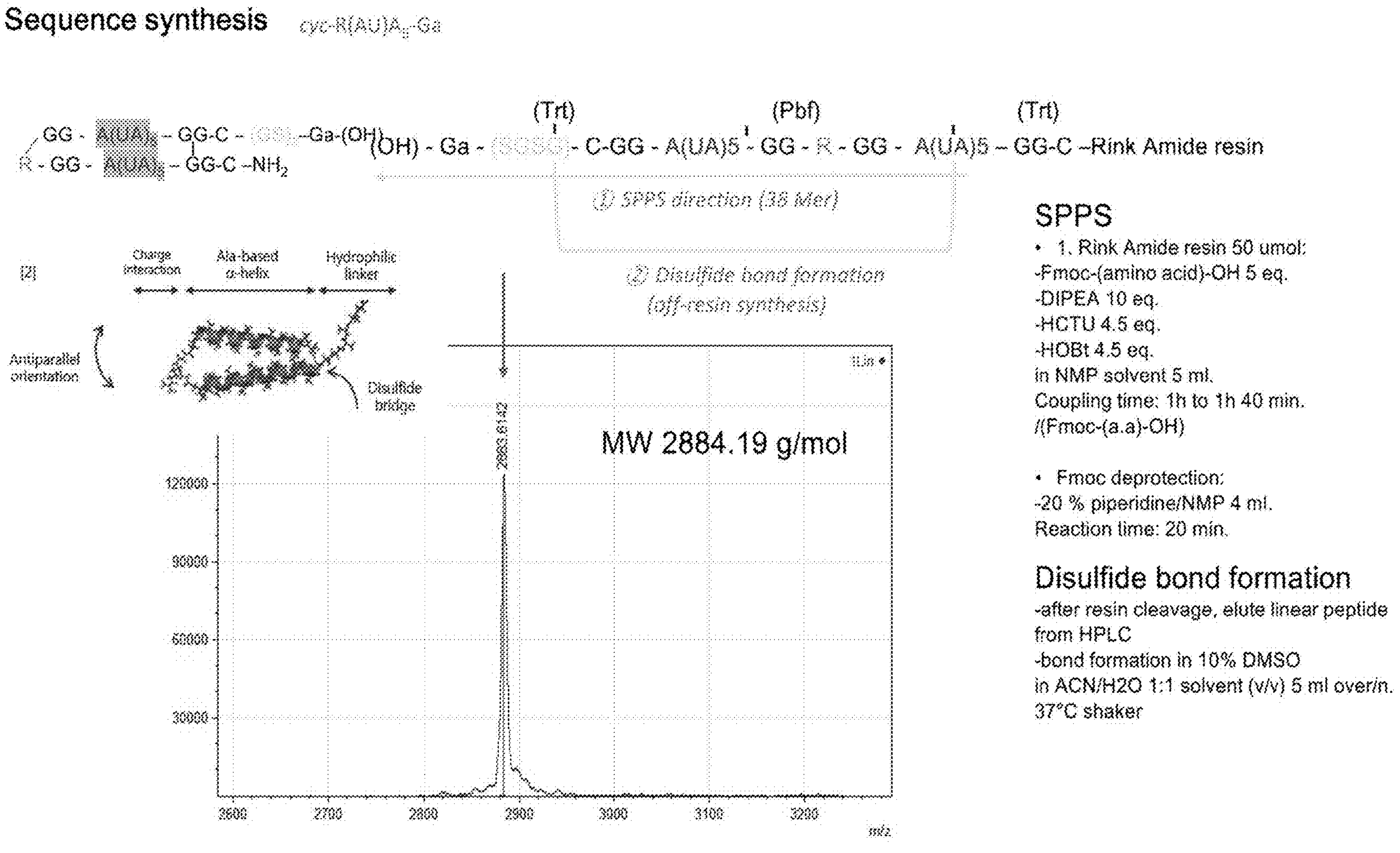
FIG. 47 shows the MALDI-TOF MS analysis result and synthesis condition for a cyclic peptide-molecule conjugate (SAB #29).

FIG. 46 shows the MALDI-TOF MS analysis result and synthesis condition for the linear peptide-molecule conjugate (SAB #28). FIG. 47 shows the MALDI-TOF MS analysis result and synthesis condition for the cyclic peptide-molecule conjugate (SAB #29).

As a result of incubating the purified linear peptide-molecule conjugate overnight in a solvent (DMSO:ACN:$H_2O$=0.1:0.45:0.45) at 37° C. to form the cyclic peptide-molecule conjugate, it was confirmed that the cyclic peptide-molecule conjugate was prepared as the thiol groups of wo cysteine (C) residues in the molecule were oxidized to form a disulfide bond, as shown in FIG. 46 and FIG. 47.

12-2. Analysis of Helicity of Linear and Cyclic Peptide-Molecule Conjugates (SAB)

The helicity of the linear and cyclic peptide-molecule conjugates prepared in Examples 28-31 were analyzed. For this, the CD spectra of the linear peptide-molecule conjugate of Example 28 (SAB #28) and the cyclic peptide-molecule conjugate of Example 29 (SAB #29) were analyzed. The CD spectra were analyzed after preparing each peptide-molecule conjugate in distilled water two concentrations of 5 μM and 50 μM and dispersing by sonicating for 20 minutes.

Figure 48:
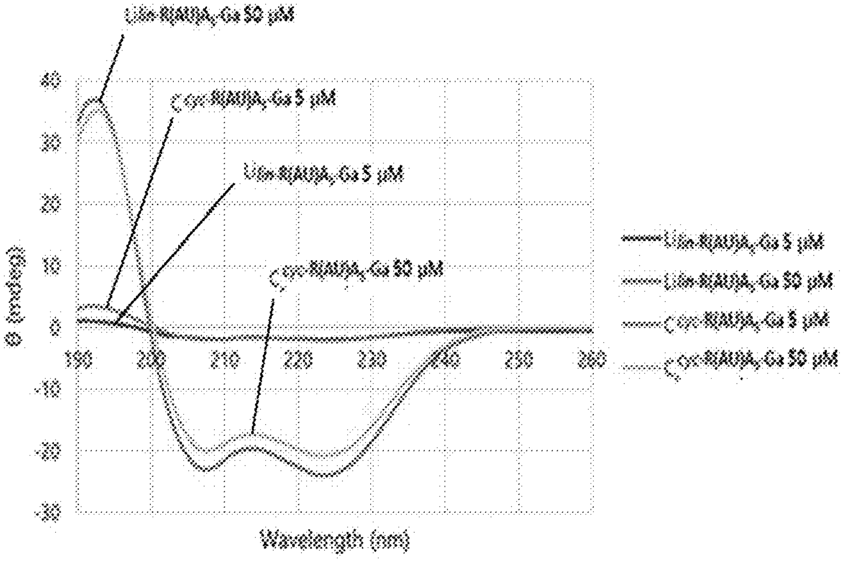
FIG. 48 shows the CD spectra of peptide-molecule conjugates of Examples 28 and 29 (lin-R(AU)A5-Ga and cyc-R(AU)A5-Ga) in an aqueous solution at 20° C.
Figure 48:
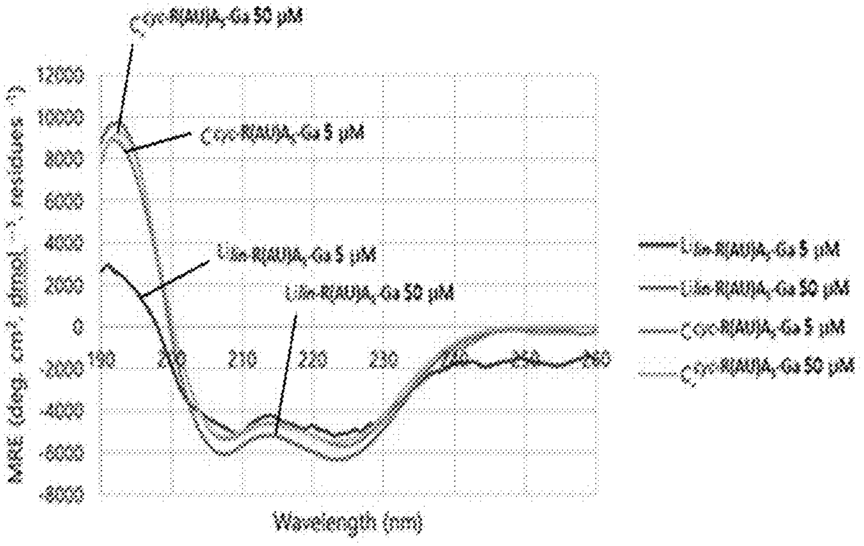

FIG. 48 shows the CD spectra of the peptide-molecule conjugates of Examples 28 and 29 (lin-R(AU)A5-Ga and cyc-R(AU)A5-Ga) in an aqueous solution at 20° C.

In FIG. 48, the graph on the left side shows raw data, and the graph on the right side shows normalized data for comparison with the effect of the concentration eliminated. Both the linear and cyclic peptide-molecule conjugates showed enough helicity ($[\theta]_{222}/[\theta 9_{208}$ ratio) of 1.0 or higher regardless of the concentration, suggesting that the peptide-molecule conjugates of Example 28 and 29 (lin-R(AU)A5-Ga, cyc-R(AU)A5-Ga) have stable α-helical structures.

12-3. Formation of Nanostructures Using Linear and Cyclic Peptide-Molecule Conjugates (SAB #28, #29) and EGFP mRNA For formation of nanostructures with EGFP mRNA, the aqueous solutions of the linear peptide-molecule conjugate of Example 28 and Example 29 were dispersed by sonicating for 5 minutes and then mixed with a 20 nM EGFP mRNA aqueous solution. After heating the mixed solution for 10 minutes at 70° C., it was immediately snap-cooled on ice. RiboRuler Low Range RNA Ladder and RiboRuler High Range RNA Ladder (Thermo Scientific, Waltham, USA) were used on the two lanes on the left side of agarose gel in order to identify the relative locations of the EGFP mRNA bands. The bands of the RiboRuler Low Range RNA Ladder correspond to 1000, 800, 600, 400, 300, 200 and 100 bases, from top to bottom, and the bands of the RiboRuler High Range RNA Ladder correspond to 6000, 4000, 3000, 2000, 1500, 1000, 500 and 200 bases, from top to bottom. Then, the mixtures with charge ratios (+/−) of 0, 0.031, 0.063, 0.125, 0.25, 0.5, 1, 2, 4, 8 and 16 were loaded in sequence.

Figure 49:
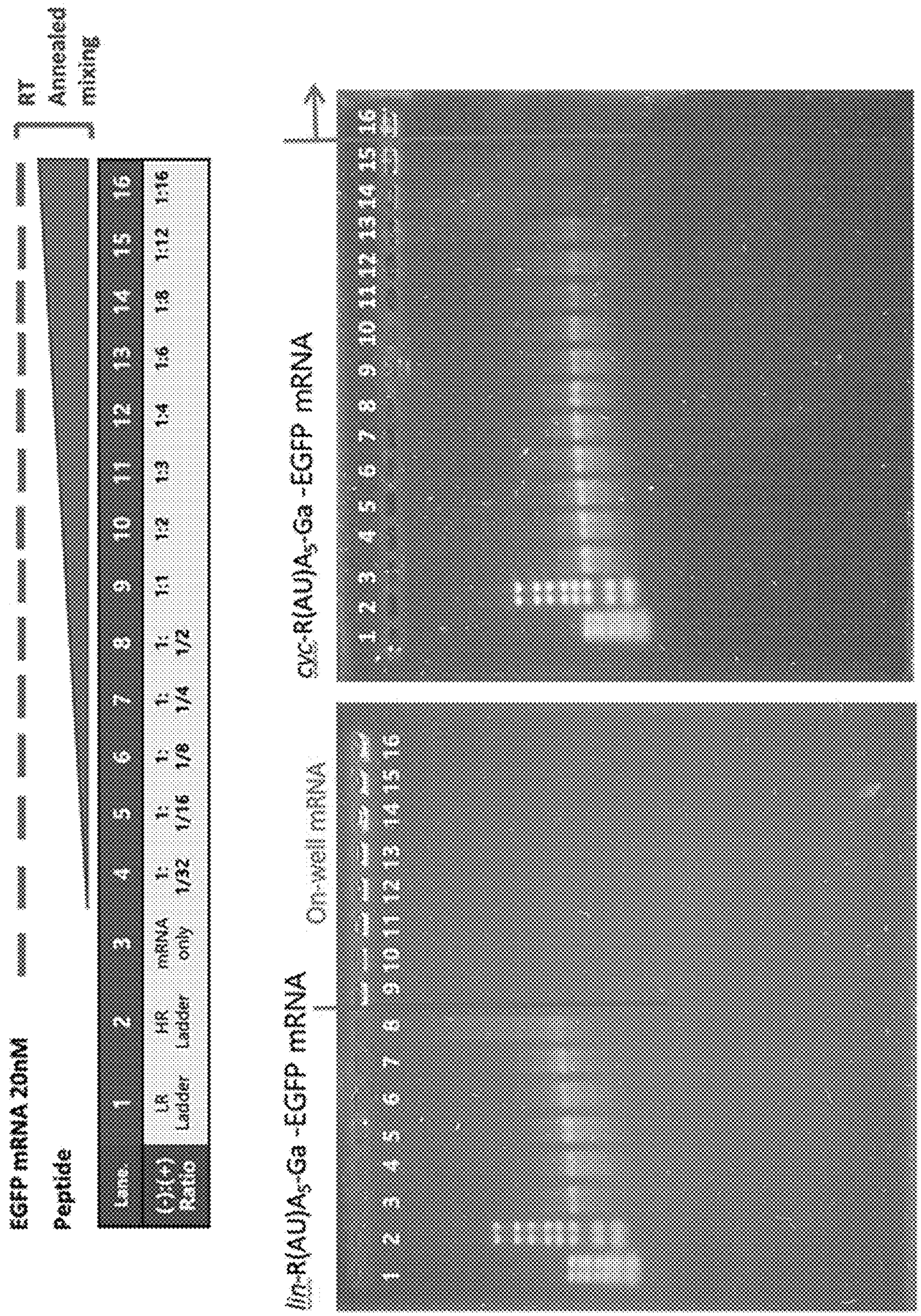
FIG. 49 shows an EMSA result for mixtures prepared by linear and cyclic peptide-molecule conjugates of Example 28 and Example 29 (SAB #28 and SAB #29) and EGFP mRNA at different charge ratios (+/−).

FIG. 49 shows an EMSA result for the mixtures prepared from the linear and cyclic peptide-molecule conjugates of Example 28 and Example 29 (SAB #28 and SAB #29) and EGFP mRNA at different charge ratios (+/−).

As seen from FIG. 49, the linear peptide-molecule conjugate (#28) formed a complete nanostructure at a charge ratio (+/−) of 1.0 or higher (left side in FIG. 49), and the cyclic peptide-molecule conjugate (#29) formed a complete nanostructure at a charge ratio (+/−) of 16 (right side in FIG. 49).

12-4. Formation of Nanostructures of Linear and Cyclic Peptide-Molecule Conjugates (SAB #30, #31) and EGFP mRNA with Glucose Bound For formation of nanostructures with EGFP mRNA, the aqueous solutions of the linear peptide-molecule conjugate of Example 30 and Example 31 were dispersed by sonicating for 5 minutes and then mixed with a 20 nM EGFP mRNA aqueous solution. After heating the mixed solution for 10 minutes at 70° C., it was immediately snap-cooled on ice. RiboRuler High Range RNA Ladder (Thermo Scientific, Waltham, USA) was used on the left side of agarose gel in order to identify the relative locations of the EGFP mRNA bands. The bands of the RiboRuler High Range RNA Ladder correspond to 6000, 4000, 3000, 2000, 1500, 1000, 500 and 200 bases, from top to bottom. Then, the samples were loaded with charge ratios (+/−) of 00, 0.063, 0.125, 0.25, 0.5, 1, 2, 4, 8, 16 and 32 in sequence.

Figure 50:
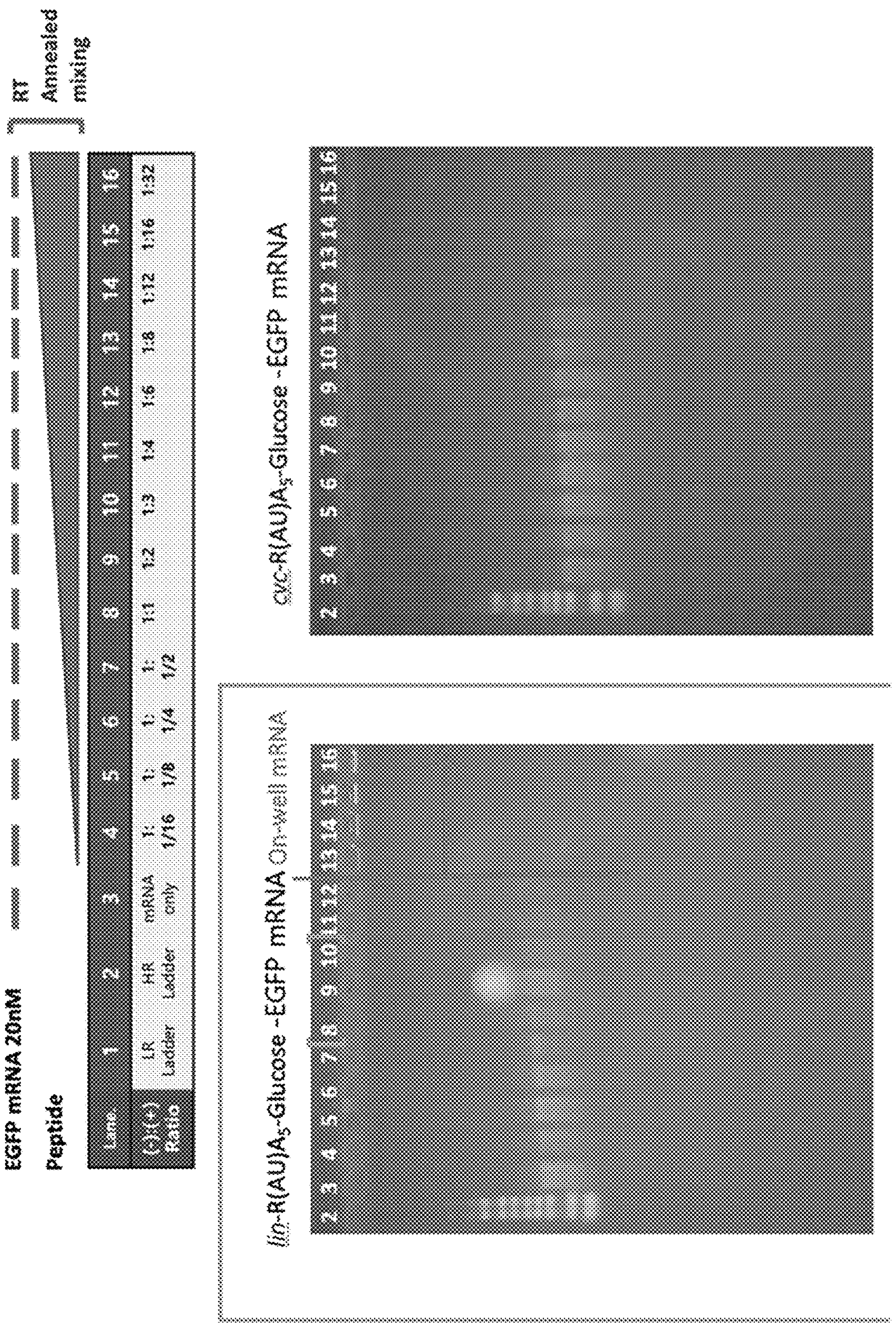
FIG. 50 shows an EMSA result for mixtures prepared by linear and cyclic peptide-molecule conjugates of Example 30 and Example 31 (SAB #30 and SAB #31) and EGFP mRNA at different charge ratios (+/−).

FIG. 50 shows an EMSA result for the mixtures prepared from the linear and cyclic peptide-molecule conjugates of Example 30 and Example 31 (SAB #30 and SAB #31) and EGFP mRNA at different charge ratios (+/−).

As shown in FIG. 50, the linear peptide-molecule conjugate (#30) formed a complete nanostructure at a charge ratio (+/−) of 8 or higher (left side in FIG. 50). The result for the cyclic peptide-molecule conjugate (SAB #31) is shown in the right side of FIG. 50. From the fact that the bands of the EGFP mRNA weaken gradually with the increase of charge ratio, it can be seen that denser nanostructures are formed as the addition amount of the peptide-molecule conjugate is increased.

To conclude, it can be seen that the peptide-molecule conjugate according to the present disclosure (SAB) has a thermodynamically very stable nanostructure and can be usefully utilized as a new carrier of nucleic acid materials. The peptide-molecule conjugate (SAB) forms an SAB/mRNA nanostructure through self-assembly with mRNA. It forms a very stable nanotube by coating the mRNA without harming its nanofiber structure, similarly to that of tobacco mosaic virus (TMV). However, the peptide-molecule conjugate (SAB) is an artificial mRNA-based self-assembled structure which competes with the RNA virus in terms of structural integrity. The mRNA coated with the peptide-molecule conjugate (SAB) is more stable than TMV. Furthermore, it is advantageous in that the stability can be controlled with the charge ratio of the peptide-molecule conjugate (SAB) and the mRNA. In addition, the peptide-molecule conjugate according to the present disclosure (SAB) may be prepared to have specificity for a desired target by binding a hydrophilic molecule, and has superior specificity and intracellular delivery efficiency. Furthermore, because the peptide-molecule conjugate (SAB) coats the nucleic acid material in the form of filament as it is, it can maintain the nucleic acid material for a long time in vivo without inactivation or denaturation.

What is claimed is:

1. A peptide-molecule conjugate comprising:

i) a fusion peptide; and ii) a hydrophilic molecule bound to at least one or both of the terminals of the first peptide and the second peptide of the fusion peptide, wherein the fusion peptide consists of:

(a) a first peptide represented by any sequence selected from SEQ ID NO: 1 and SEQ ID NOS: 3-8;

(b) a gene-binding region consisting of a 1-4 residue peptide containing a lysine (K) residue, an arginine (R) residue or a glutamic acid (E) residue;

(c) a second peptide represented by any sequence selected from SEQ ID NO: 2 and SEQ ID NOS: 3-8;

(d) a first linker bound between the first peptide and the gene-binding region; and (e) a second linker bound between the gene-binding region and the second peptide:

[SEQ ID NO: 1]
$X_1$-E-L-$X_2$-$X_3$-L-E-$X_4$-E-L-$X_5$-$X_6$-L-E

[SEQ ID NO: 2]
K-L-$X_7$-$X_8$-L-K-$X_9$-K-L-$X_{10}$-$X_{11}$-L-K-$X_{12}$

[SEQ ID NO: 3]
AUAUAUAU

[SEQ ID NO: 4]
AUAUAUAUA

[SEQ ID NO: 5]
AUAUAUAUAU

[SEQ ID NO: 6]
AUAUAUAUAUA

-continued

[SEQ ID NO: 7]
AUAUAUAUAUAU

[SEQ ID NO: 8]
AUAUAUAUAUAUA wherein each of $X_1$ to $X_{12}$ is independently selected from the group consisting of alanine (A), Aib (2-aminoisobutyric acid) and leucine (L), wherein the peptide-molecule conjugate has a molecular length of 5-6 nm.

2. The peptide-molecule conjugate according to claim 1, wherein the hydrophilic molecules bound to the first peptide and the second peptide are identical or different from each other, the hydrophilic molecule is a hydrophilic polymer or a hydrophilic targeting ligand, the hydrophilic polymer is any one selected from a group consisting of polyethylene glycol, Pluronic, pullulan, hyaluronic acid, glycol chitosan, heparin, chondroitin sulfate, fucoidan, dextran and a derivative thereof, and the hydrophilic targeting ligand is one or more selected from a group consisting of a carbohydrate, an aptamer, a vitamin, folic acid, a hexosamine and a peptide.

3. The peptide-molecule conjugate according to claim 1, wherein the peptide-molecule conjugate has a helicity of 0.8-0.9.

4. The peptide-molecule conjugate according to claim 1, wherein the peptide-molecule conjugate forms a self-assembled monolayer that surrounds a nucleic acid material through non-covalent bond with the nucleic acid material.

5. A composition for nucleic acid delivery, comprising the peptide-molecule conjugate according to claim 1 as an active ingredient.

6. The composition for nucleic acid delivery according to claim 5, wherein the nucleic acid is a DNA or an RNA.

7. The composition for nucleic acid delivery according to claim 5, wherein the composition further comprises one or more selected from a group consisting of amantadine, ammonium chloride, polyethylenimine and chloroquine.

8. The composition for nucleic acid delivery according to claim 5, wherein a mixing ratio of the peptide-molecule conjugate and the nucleic acid is 0.1-10:1 based on charge (+/− ratio).

9. The composition for nucleic acid delivery according to claim 5, wherein the peptide-molecule conjugate and the nucleic acid form, through self-assembly, a nanostructure consisting of: a core comprising the nucleic acid; and a self-assembled monolayer of the peptide-molecule conjugate surrounding the core.

10. The composition for nucleic acid delivery according to claim 9, wherein the nanostructure is a nanotube.

11. The composition for nucleic acid delivery according to claim 9, wherein the monolayer has an average thickness of 5-7 nm.

12. The peptide-molecule conjugate according to claim 1, wherein the first peptide and the second peptide have an α-helical secondary structure and are arranged side by side with the gene-binding region at the center.

13. The peptide-molecule conjugate according to claim 1, wherein the peptide-molecule conjugate is configured to rearrange and self-adjust its structure and volume fraction to correspond to a structure and volume fraction of a target.

14. The peptide-molecule conjugate according to claim 1, wherein each of the first linker and the second linker is independently selected from the group consisting of GG, GGG, Ahx (6-aminohexanoic acid), Ahx2, Ado (12-aminododecanoic acid), and 8Ado (8-amino-3,6-dioxaoctanoic acid).

15. The peptide-molecule conjugate according to claim 1, wherein electrostatic interaction is formed between all glutamic acids (E) of the first peptide and all lysines (K) of the second peptide, and hydrophobic interaction is formed between the leucine (L) of the first peptide and the second peptide.

16. The peptide-molecule conjugate according to claim 1, wherein one or more nucleobase selected from adenine, cytosine, guanine, thymine and uracil is covalently bonded to a peptide side chain of the gene-binding region (b).

17. The peptide-molecule conjugate according to claim 1, wherein, when the first peptide is a sequence represented by SEQ ID NO: 1, the second peptide is a sequence represented by SEQ ID NO: 2, and the fusion peptide has a hairpin structure.

18. The peptide-molecule conjugate according to claim 1, wherein, when the first peptide is any sequence of SEQ ID NOS: 3-8, the second peptide is any sequence selected from SEQ ID NOS: 3-8, and the fusion peptide has a linear or cyclic structure.

19. The peptide-molecule conjugate according to claim 1, wherein the gene-binding region (b) binds to a negatively charged target through interaction.

20. The peptide-molecule conjugate according to claim 16, wherein the nucleobase binds to a nucleic acid through base-pairing interaction.

* * * * *

SEQUENCE LISTING

```
Sequence total quantity: 19
SEQ ID NO: 1            moltype = AA  length = 14
FEATURE                 Location/Qualifiers
source                  1..14
                        mol_type = protein
                        organism = synthetic construct
VARIANT                 4
                        note = X can be A or L or 2-Aminoisobutyric acid
VARIANT                 1
                        note = X can be A or L or 2-Aminoisobutyric acid
VARIANT                 5
                        note = X can be A or L or 2-Aminoisobutyric acid
VARIANT                 8
                        note = X can be A or L or 2-Aminoisobutyric acid
VARIANT                 11
                        note = X can be A or L or 2-Aminoisobutyric acid
VARIANT                 12
                        note = X can be A or L or 2-Aminoisobutyric acid
SEQUENCE: 1
XELXXLEXEL XXLE                                                           14

SEQ ID NO: 2            moltype = AA  length = 14
FEATURE                 Location/Qualifiers
source                  1..14
                        mol_type = protein
                        organism = synthetic construct
VARIANT                 3
                        note = X can be A or L or 2-Aminoisobutyric acid
VARIANT                 4
                        note = X can be A or L or 2-Aminoisobutyric acid
VARIANT                 7
                        note = X can be A or L or 2-Aminoisobutyric acid
VARIANT                 10
                        note = X can be A or L or 2-Aminoisobutyric acid
VARIANT                 11
                        note = X can be A or L or 2-Aminoisobutyric acid
VARIANT                 14
                        note = X can be A or L or 2-Aminoisobutyric acid
SEQUENCE: 2
KLXXLKXKLX XLKX                                                           14

SEQ ID NO: 3            moltype = AA  length = 8
FEATURE                 Location/Qualifiers
source                  1..8
                        mol_type = protein
                        organism = synthetic construct
SEQUENCE: 3
AUAUAUAU                                                                  8

SEQ ID NO: 4            moltype = AA  length = 9
FEATURE                 Location/Qualifiers
source                  1..9
                        mol_type = protein
                        organism = synthetic construct
SEQUENCE: 4
AUAUAUAUA                                                                 9

SEQ ID NO: 5            moltype = AA  length = 10
FEATURE                 Location/Qualifiers
source                  1..10
                        mol_type = protein
                        organism = synthetic construct
SEQUENCE: 5
AUAUAUAUAU                                                                10

SEQ ID NO: 6            moltype = AA  length = 11
FEATURE                 Location/Qualifiers
```

```
source                1..11
                      mol_type = protein
                      organism = synthetic construct
SEQUENCE: 6
AUAUAUAUAU A                                                                11

SEQ ID NO: 7          moltype = AA  length = 12
FEATURE               Location/Qualifiers
source                1..12
                      mol_type = protein
                      organism = synthetic construct
SEQUENCE: 7
AUAUAUAUAU AU                                                               12

SEQ ID NO: 8          moltype = AA  length = 13
FEATURE               Location/Qualifiers
source                1..13
                      mol_type = protein
                      organism = synthetic construct
SEQUENCE: 8
AUAUAUAUAU AUA                                                              13

SEQ ID NO: 9          moltype = AA  length = 14
FEATURE               Location/Qualifiers
source                1..14
                      mol_type = protein
                      organism = synthetic construct
SEQUENCE: 9
AELAALEAEL AALE                                                             14

SEQ ID NO: 10         moltype = AA  length = 14
FEATURE               Location/Qualifiers
source                1..14
                      mol_type = protein
                      organism = synthetic construct
SEQUENCE: 10
AELUALEAEL AULE                                                             14

SEQ ID NO: 11         moltype = AA  length = 14
FEATURE               Location/Qualifiers
source                1..14
                      mol_type = protein
                      organism = synthetic construct
SEQUENCE: 11
AELUALEAEL AULE                                                             14

SEQ ID NO: 12         moltype = AA  length = 14
FEATURE               Location/Qualifiers
source                1..14
                      mol_type = protein
                      organism = synthetic construct
SEQUENCE: 12
AELUALEUEL AULE                                                             14

SEQ ID NO: 13         moltype = AA  length = 14
FEATURE               Location/Qualifiers
source                1..14
                      mol_type = protein
                      organism = synthetic construct
SEQUENCE: 13
UELUALEUEL AULE                                                             14

SEQ ID NO: 14         moltype = AA  length = 14
FEATURE               Location/Qualifiers
source                1..14
                      mol_type = protein
                      organism = synthetic construct
SEQUENCE: 14
KLAALKAKLA ALKA                                                             14

SEQ ID NO: 15         moltype = AA  length = 14
FEATURE               Location/Qualifiers
source                1..14
                      mol_type = protein
                      organism = synthetic construct
```

-continued

```
SEQUENCE: 15
KLUALKAKLA ULKA                                                    14

SEQ ID NO: 16           moltype = AA  length = 14
FEATURE                 Location/Qualifiers
source                  1..14
                        mol_type = protein
                        organism = synthetic construct
SEQUENCE: 16
KLUALKUKLA ULKA                                                    14

SEQ ID NO: 17           moltype = AA  length = 14
FEATURE                 Location/Qualifiers
source                  1..14
                        mol_type = protein
                        organism = synthetic construct
SEQUENCE: 17
KLUALKUKLA ULKU                                                    14

SEQ ID NO: 18           moltype = DNA  length = 20
FEATURE                 Location/Qualifiers
source                  1..20
                        mol_type = other DNA
                        organism = synthetic construct
SEQUENCE: 18
gcgagctgca cgctgccgtc                                              20

SEQ ID NO: 19           moltype = DNA  length = 20
FEATURE                 Location/Qualifiers
source                  1..20
                        mol_type = other DNA
                        organism = synthetic construct
SEQUENCE: 19
gacggcagcg tgcagctcgc                                              20
```